US012595287B2

(12) United States Patent
Vinetz et al.

(10) Patent No.: US 12,595,287 B2
(45) Date of Patent: Apr. 7, 2026

(54) LEPTOSPIRAL PROTEINS AND USES THEREOF

(71) Applicant: YALE UNIVERSITY, New Haven, CT (US)

(72) Inventors: Joseph Vinetz, New Haven, CT (US); Michael Matthias, New Haven, CT (US)

(73) Assignee: Yale University, New Haven, CT (US)

( * ) Notice: Subject to any disclaimer, the term of this patent is extended or adjusted under 35 U.S.C. 154(b) by 524 days.

(21) Appl. No.: 17/760,134

(22) PCT Filed: Feb. 4, 2021

(86) PCT No.: PCT/US2021/016564
§ 371 (c)(1),
(2) Date: Aug. 4, 2022

(87) PCT Pub. No.: WO2021/158755
PCT Pub. Date: Aug. 12, 2021

(65) Prior Publication Data
US 2023/0151064 A1      May 18, 2023

Related U.S. Application Data

(60) Provisional application No. 62/971,434, filed on Feb. 7, 2020.

(51) Int. Cl.
*A61K 39/02*          (2006.01)
*C07K 14/20*          (2006.01)
*A61K 39/00*          (2006.01)

(52) U.S. Cl.
CPC .............. *C07K 14/20* (2013.01); *A61K 39/00* (2013.01); *C07K 2319/21* (2013.01)

(58) Field of Classification Search
None
See application file for complete search history.

(56) References Cited

U.S. PATENT DOCUMENTS 10,525,117 B2 *   1/2020   Bomchil ............ A61K 39/0208
2008/0193440 A1    8/2008   Jensen
2017/0021004 A1    1/2017   Bomchil

FOREIGN PATENT DOCUMENTS

WO      2019060384      3/2019
WO      2021158755      8/2021

OTHER PUBLICATIONS

Cosate et al (Genome Announc. 2015. 3:e01302-15; "Whole-Genome Sequence of Leptospira interrogans Serovar Hardjo Subtype Hardjoprajitno Strain Norma, Isolated from Cattle in a Leptospirosis Outbreak in Brazil.").*

Mikayama et al. (Nov. 1993. Proc. Natl.Acad.Sci. USA, vol. 90 : 10056-10060).*
Witkowski et al., (Biochemistry 38:11643-11650, 1999).*
Kisselev L., (Structure, 2002, vol. 10: 8-9).*
Whisstock et al., (Quarterly Reviews of Biophysics 2003, vol. 36 (3): 307-340; abstract at this time).*
Anonymous , "Leptospira interrogans serovar Lai str. 56601 chromosome I, complete sequence", Nucleotide, (Jan. 30, 2014), Database accession No. AE010300, URL: NCBI, XP055864939 [Y] 8, 11, 13, 14/(8,11,13) * especially nts 625563-623743 *.
Anonymous , "Q8F8D7 (Q8F8D7_LEPIN)", Uniprotkb, (Mar. 1, 2003), Database accession No. Q8F8D7, URL: UNIPROT, XP055864934 [Y] 1, 4, 5, 14/(1,4,5) * especially full sequence *.
Anonymous, 2003, "Q8F8D7 (Q8F8D7_LEPIN)", Database UNIPROTKB, Mar. 1, 2023.
Chaurasia et al., 2022, "Pathogenic Leptospira Evolved a Unique Gene Family Comprised of Ricin B-Like Lectin Domain-Containing Cytotoxins", Front Microbiol, 13:859680.
Conrad et al., 2017, "LigB subunit vaccine confers sterile immunity against challenge in the hamster model of leptospirosis", PLoS Negl Trop Dis, 11(3):e0005441.
Coutinho et al., 2011, "A LigA Three-Domain Region Protects Hamsters from Lethal Infection by Leptospira interrogans", PLoS Negl Trop Dis, 5(12):e1422.
De Oliveira et al., 2021, "Protective efficacy of whole-cell inactivated Leptospira vaccines made using virulent or avirulent strains in a hamster model", Vaccine, 39(39):5626-34.
Fouts et al, 2016, "What Makes a Bacterial Species Pathogenic?: Comparative Genomic Analysis of the Genus Leptospira", PLoS Negl Trop Dis. 10(2): e0004403.
Govindan et al., 2021, "Expression and preliminary characterization of the potential vaccine candidate LipL32 of leptospirosis", Appl Nanosci, 1-15.
Haake et al., 1999, "Leptospiral Outer Membrane Proteins OmpL1 and LipL41 Exhibit Synergistic Immunoprotection", 1999, Infect Immun, 67(12):6572-8223.
Haake et al., 2021, "Leptospiral Immunoglobulin-Like Domain Proteins: Roles in Virulence and Immunity", Front Immunol, 11:579907.
Harrington et al., 2017, "Experimental confirmation of unique, functional ricin-b like lectin domains in pathogenic leptospira", ASTMH, Annual Meeting, Abstract Book, pp. 1-674, XP0931336600, URL: https://www.astmh.org/ASTMH/media/2017-Annual-Meeting/ASTMH-2017-Abstract-Book.pdf.
Lauretti-Ferreira Fabiana, Teixeira André Azevedo Reis, Giordano Ricardo José, Da Silva Josefa Bezerra, Abreu Patricia Antonia Estima, Barbosa Angela Silva, Akamatsu Milena Apetito, Ho Paulo Lee, "Characterization of a virulence-modifying protein of Leptospira interrogans identified by shotgun phage display", Frontiers in Microbiology, vol. 13, doi:10.3389/fmicb.2022.1051698, XP093034018.
Lehmann Jason S., Fouts Derrick E., Haft Daniel H., Cannella Anthony P., Ricaldi Jessica N., Brinkac Lauren, Harkins Derek, Durkin Scott, Sanka Ravi, Sutton Granger, Moreno Angelo, Vinetz Joseph M., Matthias Michael A., "Pathogenomic Inference of Virulence-Associated Genes in Leptospira interrogans", PLoS Neglected Tropical Diseases, (Oct. 1, 2013), vol. 7, No. 10, doi:10.1371/journal.pntd.0002468, p. e2468, XP093034010.

(Continued)

*Primary Examiner* — Jennifer E Graser
(74) *Attorney, Agent, or Firm* — Riverside Law LLP

(57)          ABSTRACT

The invention provides compositions and methods for using Leptospiral virulence modifying (VM) proteins or fragments or fusions thereof, as vaccines and as therapeutic agents for the treatment of cancer.

10 Claims, 34 Drawing Sheets

Specification includes a Sequence Listing.

(56)            References Cited

OTHER PUBLICATIONS

Lessa-Aquino, 2017, "" Distinct antibody responses of patients with mild and severe leptospirosis determined by whole proteome microarray analysis, PLoS Negl Trop Dis, 11(1):e0005349.

Levett, 2001, "Leptospirosis", Clin Microbiol Rev, 14(2):296-326.

Marcsisin et al., 2013, "Use of a high-throughput screen to identify Leptospira mutants unable to colonize the carrier host or cause disease in the acute model of infection", J Med Microbiol, 62(Pt 10):1601-1608.

Matsunaga et al, 2007, "Response of Leptospira interrogans to Physiologic Osmolarity: Relevance in Signaling the Environment-to-Host Transition", Infect Immun, 75(6): 2864-2874.

Matsunaga et al., 2005, "Osmolarity, a key environmental signal controlling expression of leptospiral proteins LigA and LigB and the extracellular release of LigA", Infect Immun, 73(1):70-8.

Murray et al., 2009, "Genome-Wide Transposon Mutagenesis in Pathogenic Leptospira Species", Infect. Immun, 77:810-816.

Phoka et al., 2021, "Identification of in vivo expressed proteins in live attenuated lipopolysaccharide mutant that mediates heterologous protection against *Leptospira* spp", Vet Microbiol, 262:109220.

Ren et al., 2003, "Unique physiological and pathogeni features of Leptospira interrogans revealed by whole-genome sequencing", Nature, vol. 422, No. 6934, pp. 888-893, Nature, vol. 422, No. 6934, pp. 888-893.

Techawiwattanaboon et al., 2019, "Reduced Renal Colonization and Enhanced Protection by Leptospiral Factor H Binding Proteins as a Multisubunit Vaccine against Leptospirosis in Hamsters", Vaccines (Basel), 7(3).

Teixeira et al., 2020, "Immunoprotective Activity Induced by Leptospiral Outer Membrane Proteins in Hamster Model of Acute Leptospirosis", Front Immunol, 11:568694.

Viriyakosol et al., 2006, "Toll-like receptor 4 protects against lethal Leptospira interrogans serovar icterohaemorrhagiae infection and contributes to in vivo control of leptospiral burden", Infect Immun. 74(2):887-95.

Wunder et al., 2021, "A live attenuated-vaccine model confers cross-protective immunity against different species of the Leptospira genus", Elife, 10:e64166. doi: 10.7554/eLife.64166. PMID: 33496263; PMCID: PMC7837694.

* cited by examiner

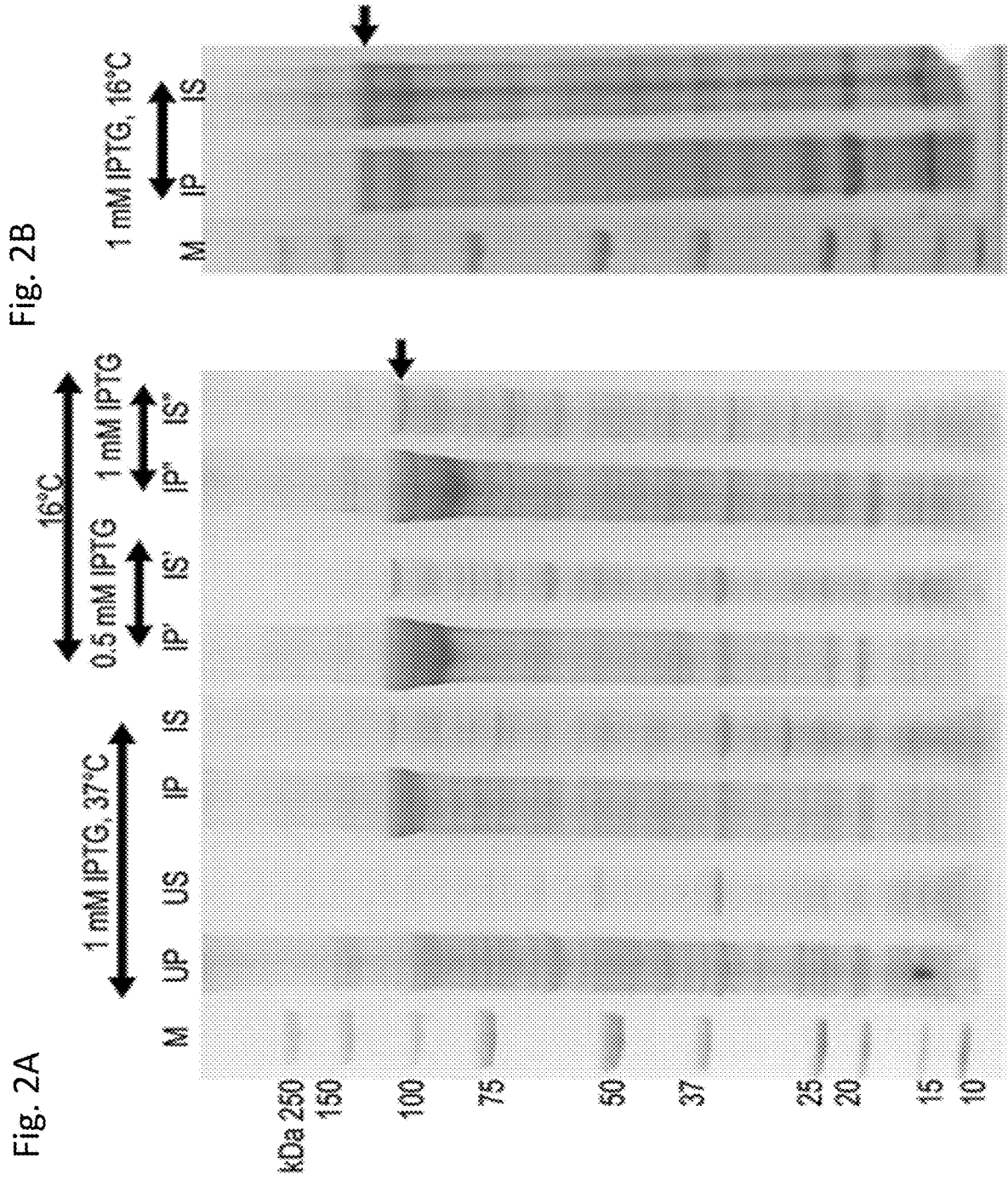

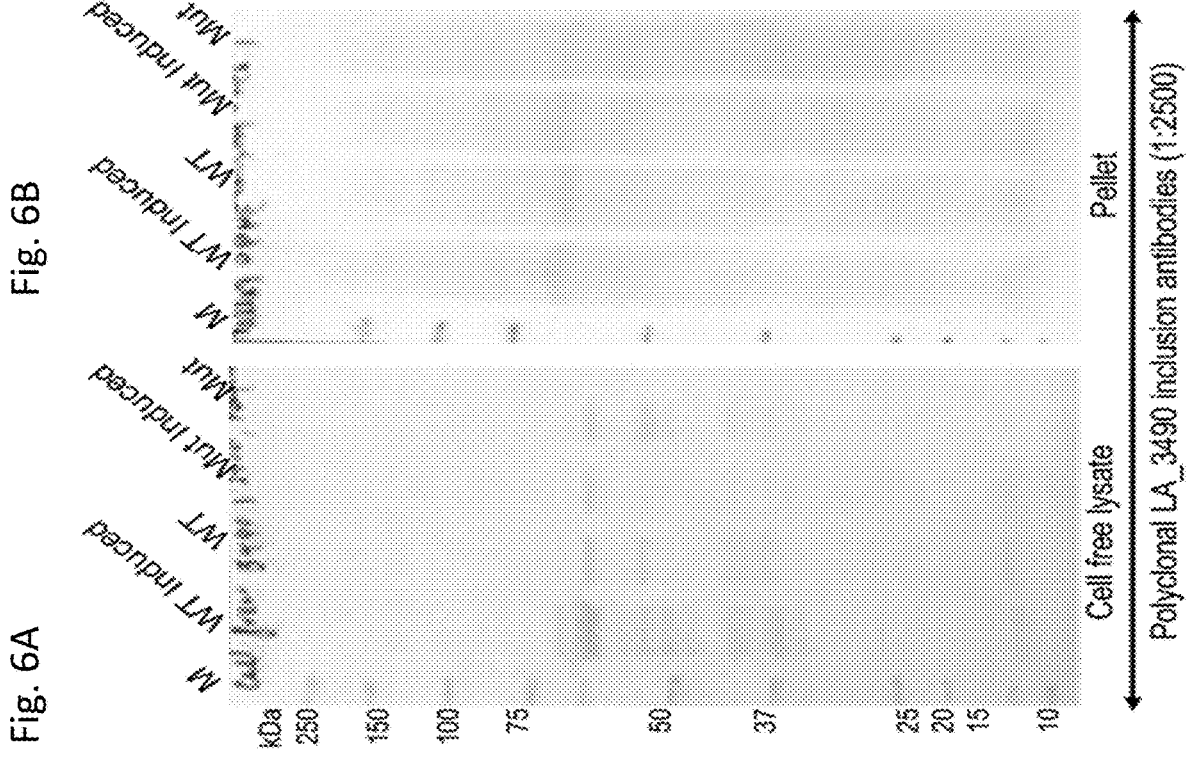

LEPTOSPIRAL PROTEINS AND USES THEREOF

CROSS-REFERENCE TO RELATED APPLICATIONS

This application is the U.S. national phase application filed under 35 U.S.C. § 371 claiming benefit to International Patent Application No. PCT/US21/16564, filed on Feb. 4, 2021, which claims priority to U.S. Provisional Application No. 62/971,434, filed Feb. 7, 2020, each of which is hereby incorporated by reference herein in its entirety.

STATEMENT REGARDING FEDERALLY SPONSORED RESEARCH OR DEVELOPMENT

This invention was made with government support under AI115658 awarded by National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "047162-5283-00US_SequenceListing.txt"; created on Jan. 25, 2023, and 34,360 bytes in size, is hereby incorporated by reference.

BACKGROUND OF THE INVENTION

The PF07598 gene family was identified as belonging solely to pathogenic *Leptospira* (Fouts et al, 2016, PLoS Negl Trop Dis. 10(2): e0004403; Lehmann et al, 2013, PLoS Negl Trop Dis, 7(10): e2468.) Members of this gene family previously known to be upregulated by osmolarity but the gene function is currently not known (Matsunaga et al, 2007; Infect Immun, 75(6): 2864-2874). In vivo upregulation of PF07598 gene family members has been reported in a hamster model (Lehmann et al, 2013; PLoS Negl Trop Dis, 7(10): e2468), and a human antibody response to one member of this gene family has been reported in vivo (Lessa-Aquino, 2017, PLoS Negl Trop Dis, 11(1): e0005349). Further, random transposon mutagenesis of *Leptospira interrogans* serovar Manilae has been reported (Marcsisin et al, 2013, J Med Microbiol, 62(Pt 10):1601-1608), yet the function remains unknown.

Human leptospirosis is common in developing countries, and there is an increased incidence in industrialized countries. Only limited progress has been made towards implementing effective public health responses, and no vaccine is registered for humans.

There remains a need in the art for novel compositions that have vaccine potential against pathogenic *Leptospira*. The current invention satisfies this unmet need.

SUMMARY OF THE INVENTION

In one embodiment, the invention relates to a composition comprising a Leptospiral virulence modifying (VM) protein, a fragment thereof, or a variant thereof. In one embodiment, the Leptospiral VM protein is LA_0620 or LA_3490, or a fragment thereof, or a variant thereof.

In one embodiment, the composition is a fusion protein comprising a Leptospiral VM domain and a targeting domain specific for binding to an antigen.

In one embodiment, the antigen is a bacterial antigen, viral antigen, parasitic antigen, cancer antigen, tumor-associated antigen, or tumor-specific antigen.

In one embodiment, the composition comprises a full length Leptospiral VM protein. In one embodiment, the Leptospiral VM protein comprises an amino acid sequence of SEQ ID NO:1, SEQ ID NO:2, SEQ ID NO:7 or SEQ ID NO:8.

In one embodiment, the composition comprises a fragment comprising the ricin B domain of the full length Leptospiral VM protein. In one embodiment, the ricin B domain comprises an amino acid sequence of SEQ ID NO:3 or SEQ ID NO:4.

In one embodiment, the invention relates to a composition comprising a nucleic acid molecule encoding a Leptospiral virulence modifying (VM) protein. In one embodiment the Leptospiral VM protein is LA_0620 or LA_3490, or a fragment thereof, or a variant thereof.

In one embodiment, the nucleic acid molecule encodes a fusion protein comprising a Leptospiral VM domain and a targeting domain specific for binding to an antigen.

In one embodiment, the antigen is a bacterial antigen, viral antigen, parasitic antigen, cancer antigen, tumor-associated antigen, or a tumor-specific antigen.

In one embodiment, the nucleic acid molecule encodes a full length Leptospiral VM protein. In one embodiment, the nucleic acid molecule encodes an amino acid sequence of SEQ ID NO:1, SEQ ID NO:2, SEQ ID NO:7 or SEQ ID NO:8. In one embodiment, the nucleic acid molecule comprises a nucleotide sequence of SEQ ID NO:8 or SEQ ID NO:9.

In one embodiment, the nucleic acid molecule encodes a fragment comprising the ricin B domain of the full length Leptospiral VM protein. In one embodiment, the nucleic acid molecule encodes an amino acid sequence of SEQ ID NO:3 or SEQ ID NO:4. In one embodiment, the nucleic acid molecule comprises a nucleotide sequence of SEQ ID NO:10 or SEQ ID NO:11.

In one embodiment, the composition comprises a vaccine.

In one embodiment, the invention relates to a method of inducing an immune response in a subject, the method comprising administering a composition comprising a nucleic acid molecule encoding a Leptospiral virulence modifying (VM) protein to the subject.

In one embodiment, the subject is currently infected with *Leptospira* sp and the composition induces an immune response against *Leptospira* sp.

In one embodiment, the subject is not currently infected with *Leptospira* sp and the composition induces an immune response against *Leptospira* sp.

In one embodiment, the invention relates to a method of treating or preventing a disease or disorder in a subject, comprising administering a composition comprising a nucleic acid molecule encoding a Leptospiral virulence modifying (VM) protein to the subject.

In one embodiment, the disease or disorder is cancer, a bacterial infection, a viral infection, or a parasitic infection.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the

US 12,595,287 B2

Figure 1:
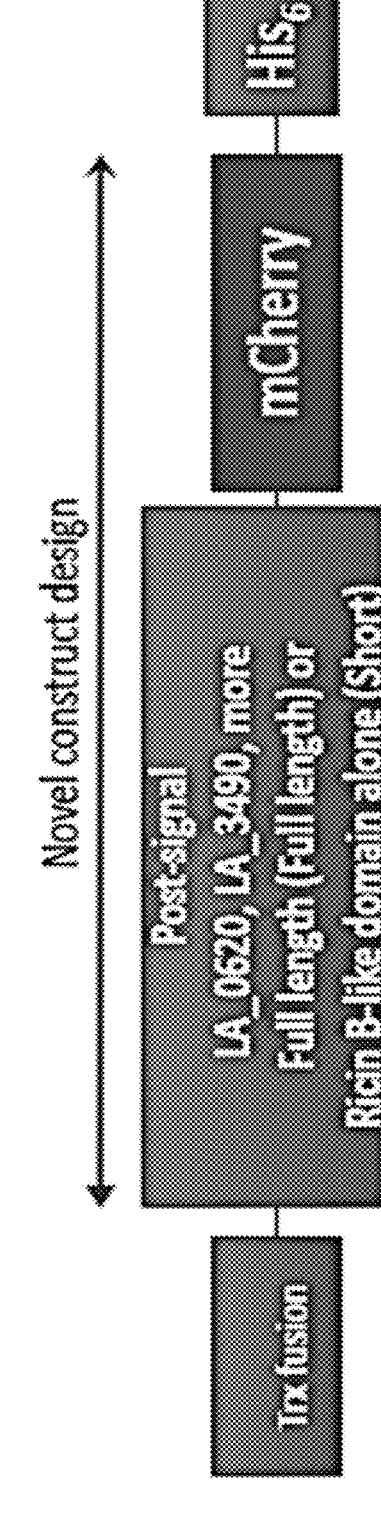
Figure 2C:
Figure 2D:
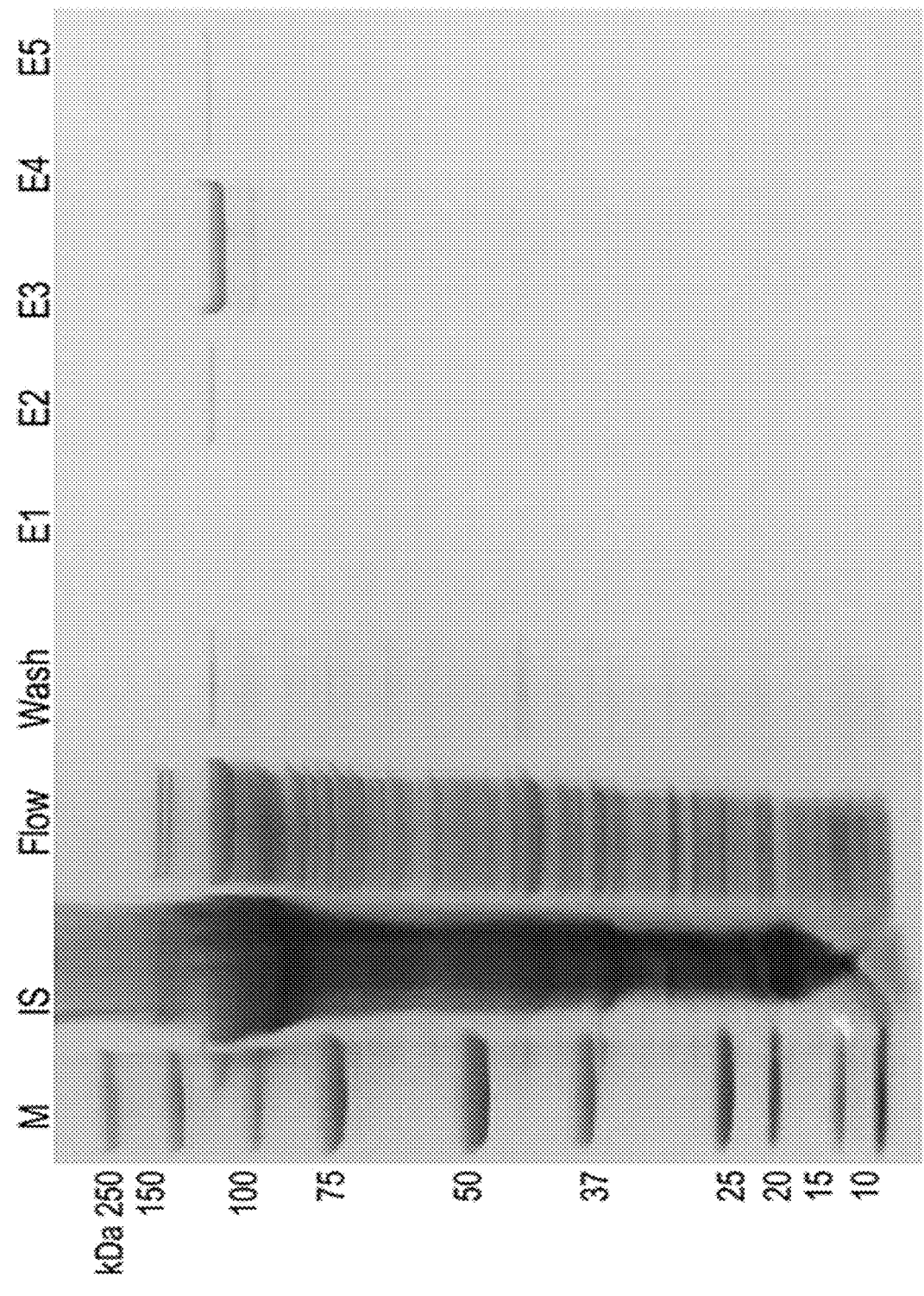
Figure 2E:
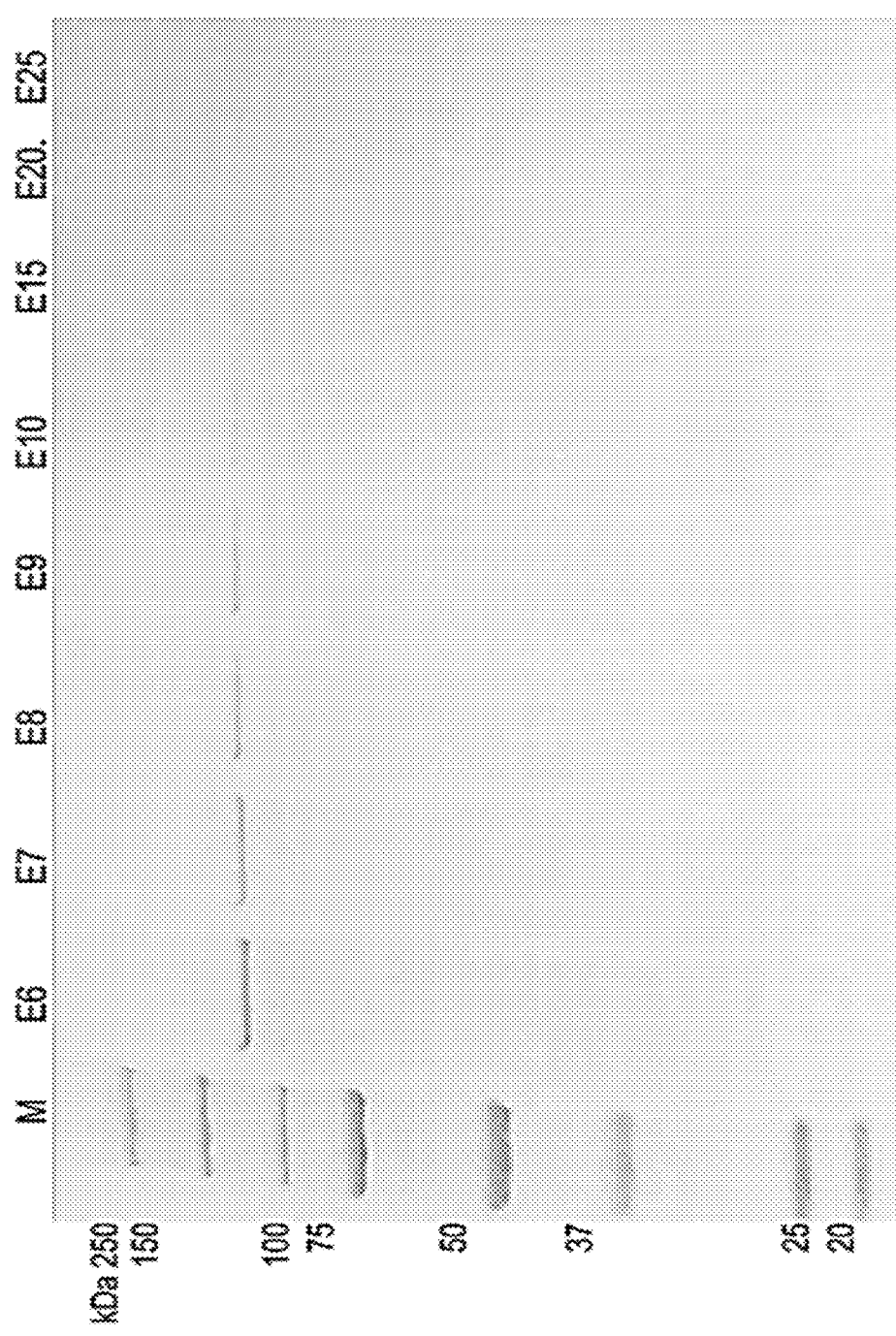

3 precise arrangements and instrumentalities of the embodiments shown in the drawings.

FIG. 1 depicts a schematic diagram of the synthetic gene construct.

FIG. 2A through FIG. 2E depict the optimization (FIG. 2A and FIG. 2B), expression (FIG. 2D and FIG. 2E) and purification (FIG. 2C) of soluble rLA_3490_Full.

Figure 3A:
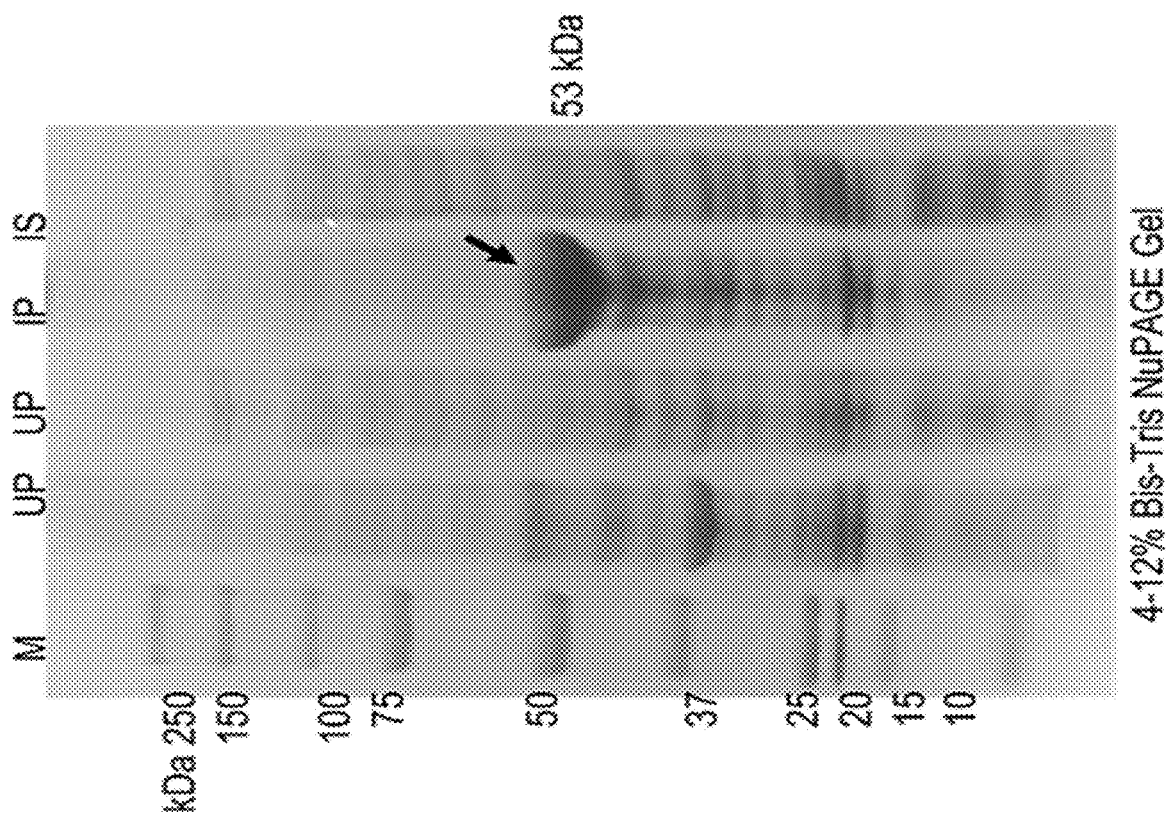
Figure 3B:
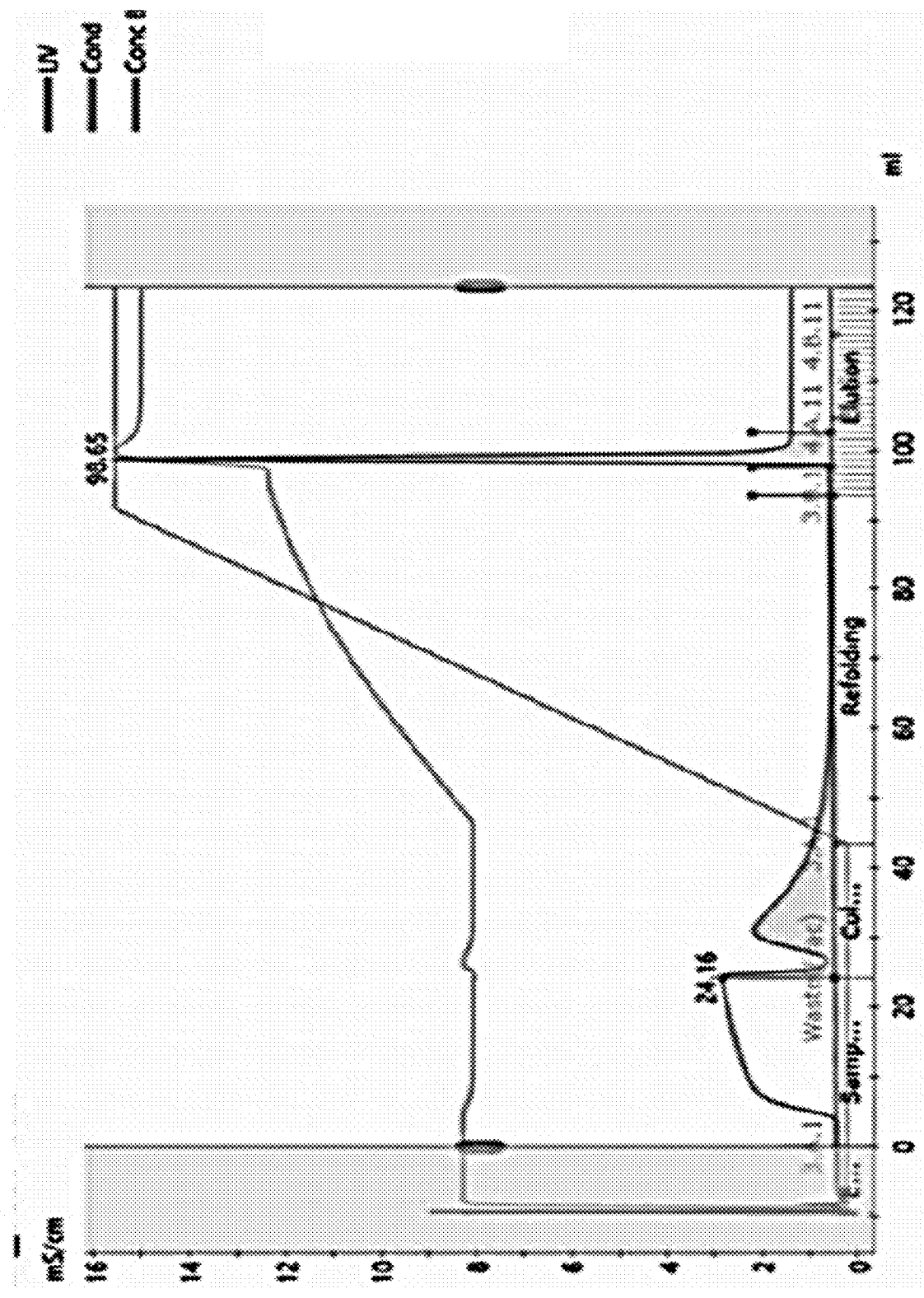
Figure 3C:
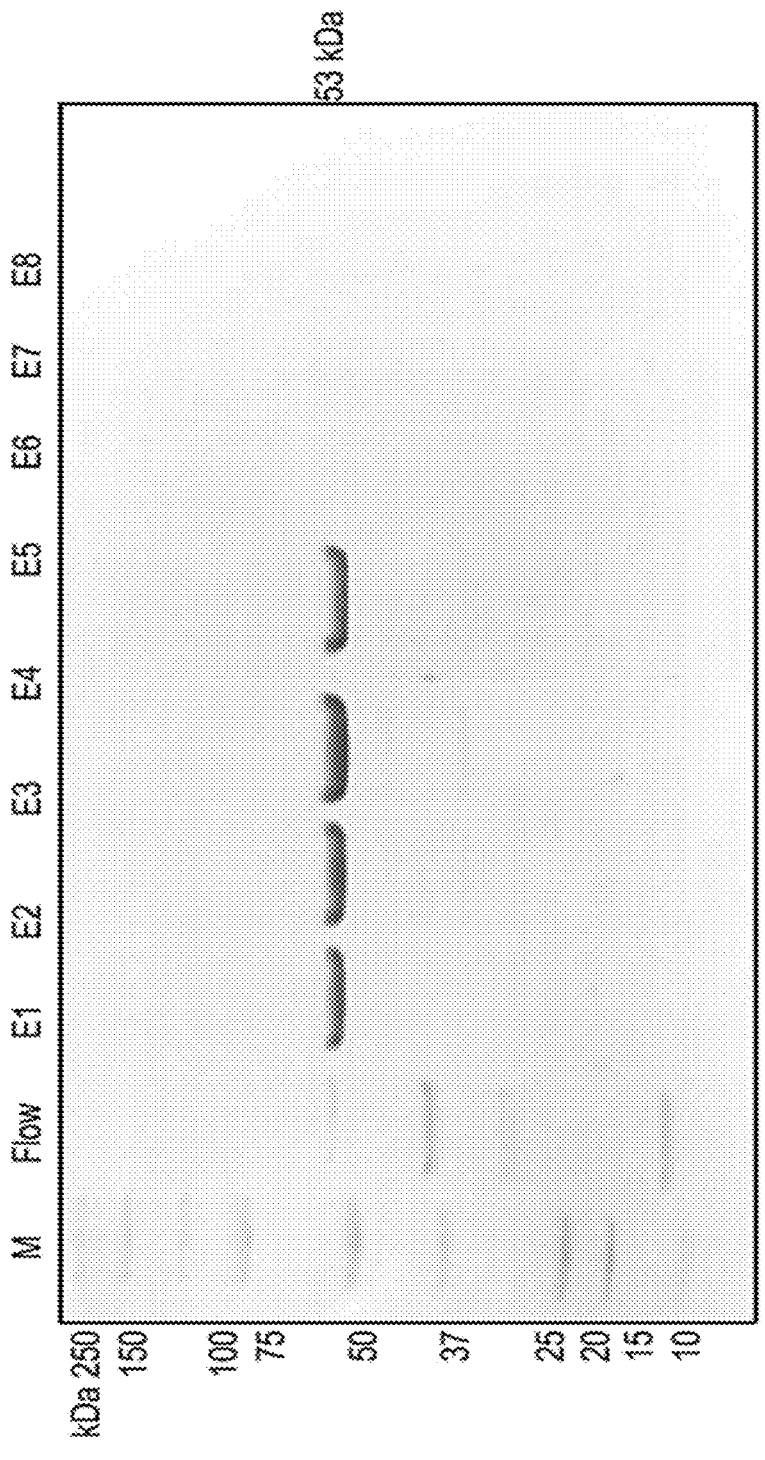

FIG. 3A through FIG. 3C depict the expression (FIG. 3C), on column refolding (FIG. 3A) and purification (FIG. 3B) of rLA_0620_Short.

Figure 4:
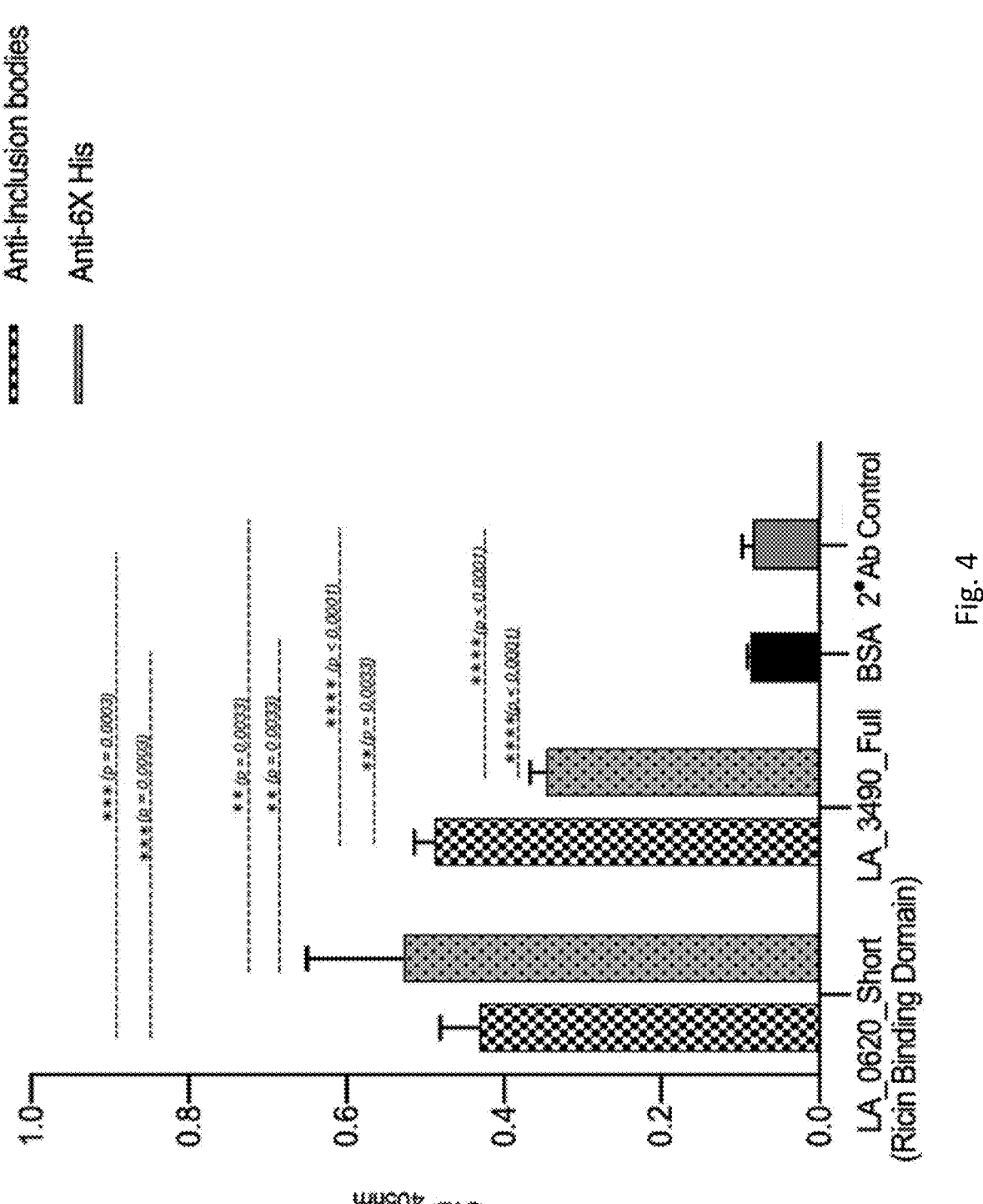

FIG. 4 depicts exemplary experimental data demonstrating that recombinant VM proteins, like Ricin B, binds to Asialofetuin (terminal galactose-containing glycoprotein).

Figures 5A, 5B:
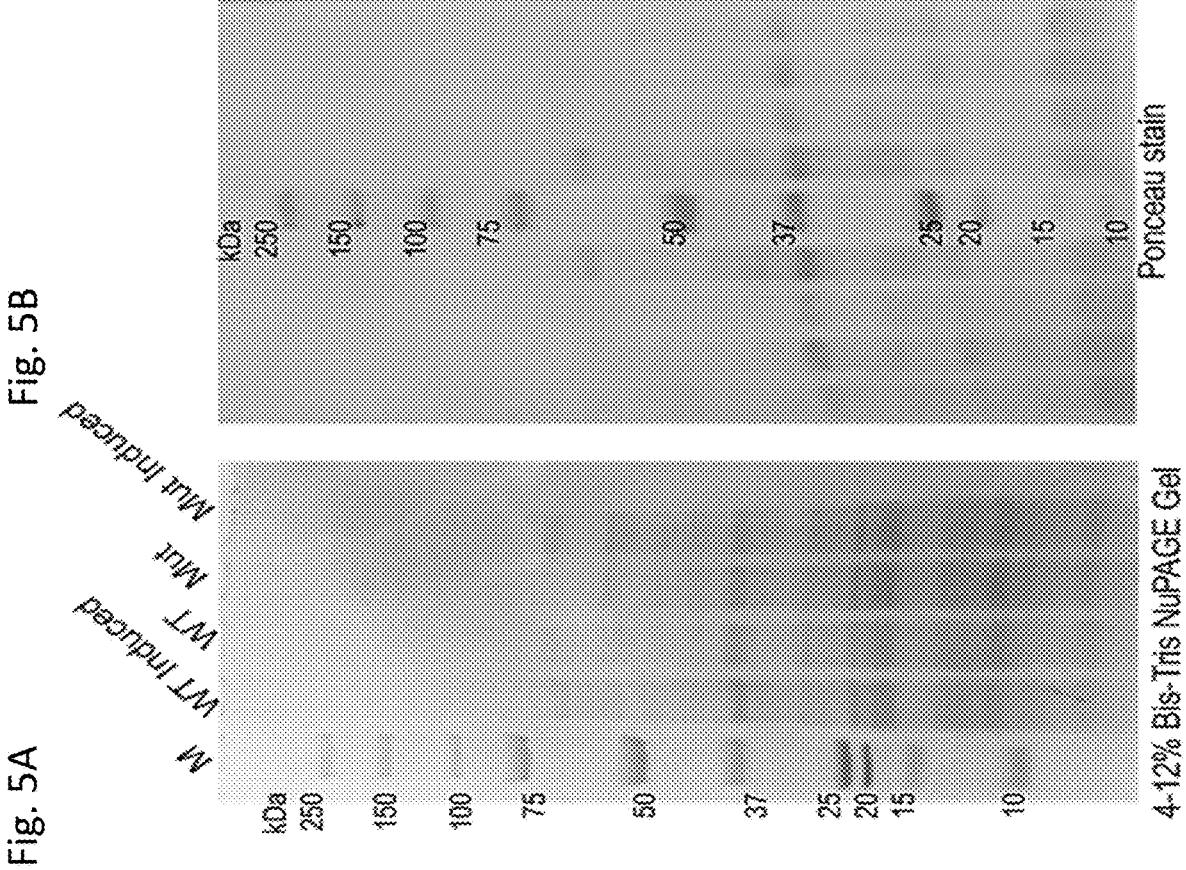
Figure 5C:
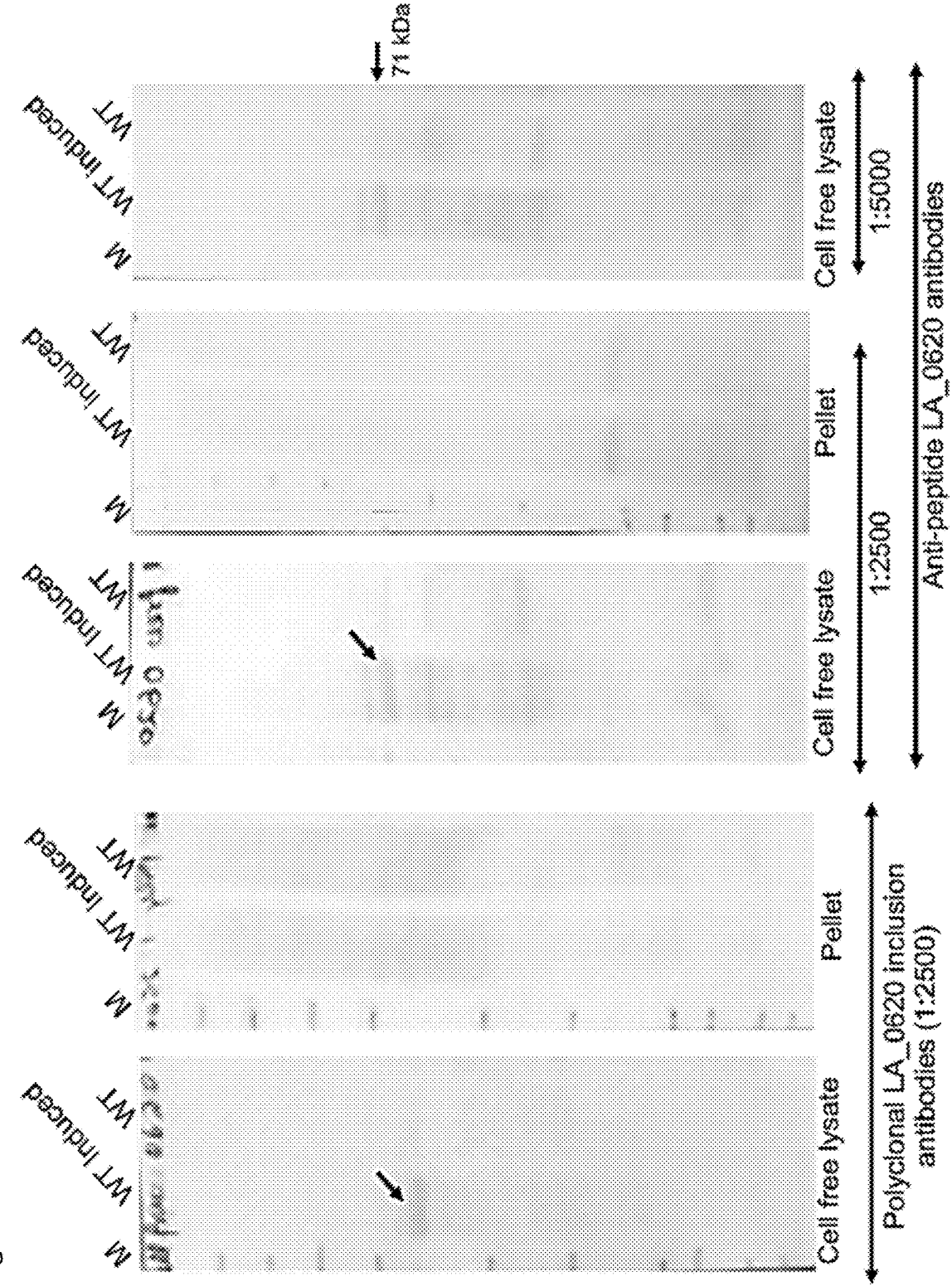

FIG. 5A through FIG. 5C depict expression of a LA_0620 VM paralog in pathogenic *Leptospira interrogans* serovar Manilae under in vitro. Conditions mimicking in vivo conditions. FIGS. 5A and 5B depict analysis of proteins expressed by *Leptospira interrogans* serovar Manilae wild type (WT) incubated in EMJH culture medium with or without 120 mM NaCl and 10% rat serum (mimicking in vivo conditions, induced), or in the presence of a mutant lacking the expression of the LA_3490 ortholog (mutant). FIG. 5A depicts Coomassie Blue staining of SDS-PAGE gel. FIG. 5B depicts Ponceau S staining of electroblot of SDS-PAGE under conditions identical to 5A to nitrocellulose membrane. FIG. 5C is an immunoblot, using a mouse antiserum raised against recombinant LA_0620 or a specific LA_0620 peptide that demonstrates the in vitro induction of LA_0620 orthology protein expression by. *L. interrogans* serovar Manilae under in vitro conditions (120 mM NaCl, 10% rat serum) that mimic in vivo conditions. This is the first time that this protein has been visualized.

Figure 6C:
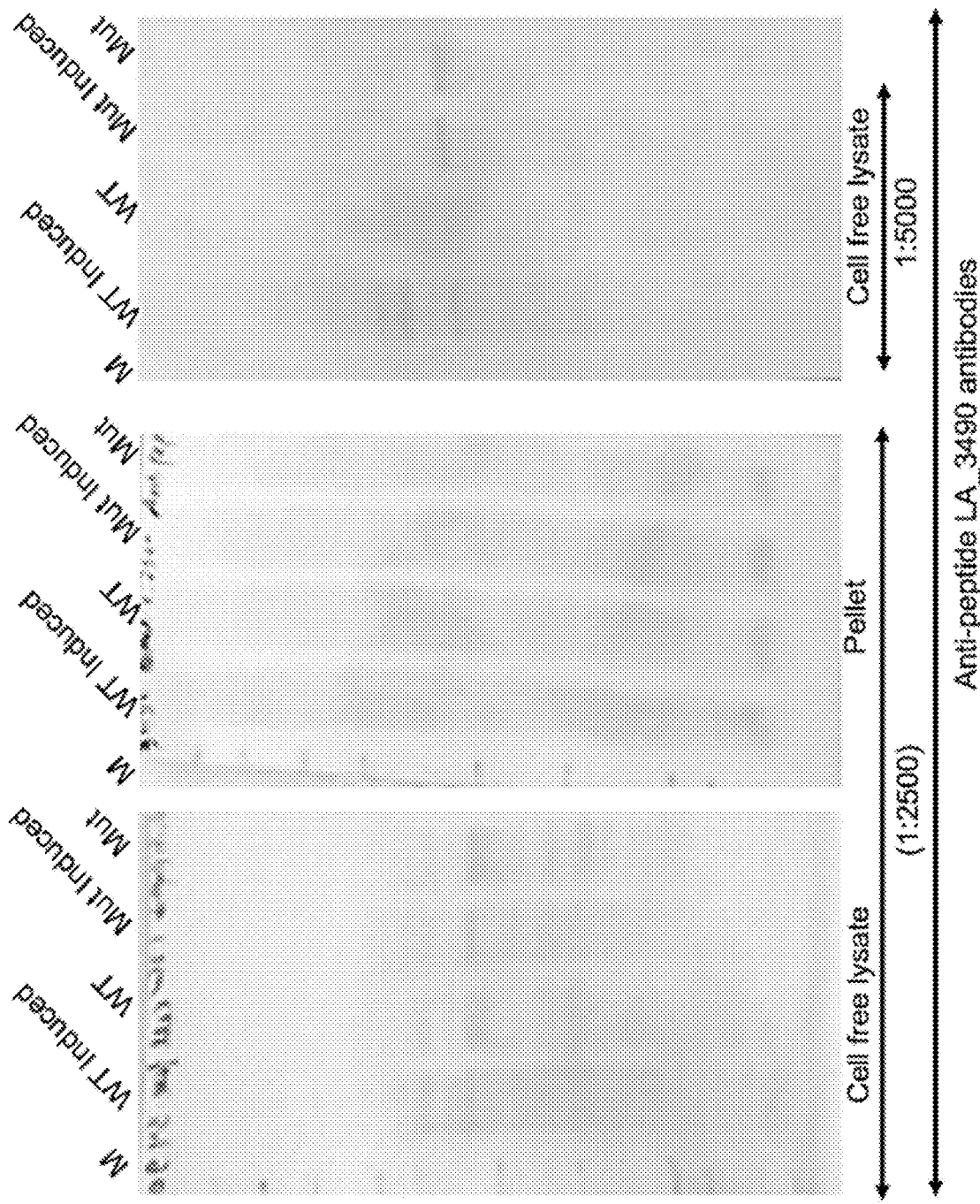

FIG. 6A through FIG. 6C depict western blot detection of LA_3490 VM paralog in Pathogenic *Leptospira* serovar Manilae. FIG. 6A through FIG. 6C depict expression of the LA-3490 VM paralog in pathogenic *Leptospira interrogans* serovar Manilae under in vitro conditions mimicking in vivo conditions. FIGS. 6A and 6B depict analysis of proteins expressed by *Leptospira interrogans* serovar Manilae wild type (WT) incubated in EMJH culture medium with or without 120 mM NaCl and 10% rat serum (mimicking in vivo conditions, induced), or in the presence of a mutant lacking the expression of the LA_3490 ortholog (mutant). FIG. 6A depicts Coomassie Blue staining of SDS-PAGE gel. FIG. 6B depicts Ponceau S staining of electroblot of SDS-PAGE under conditions identical to 5A to nitrocellulose membrane. FIG. 6C is an immunoblot, using a mouse antiserum raised against recombinant LA_3490 that demonstrates the in vitro induction of LA_3490 orthology protein expression by. *L. interrogans* serovar Manilae under in vitro conditions (120 mM NaCl, 10% rat serum) that mimic in vivo conditions. This is the first time that this protein has been visualized.

Figure 7:
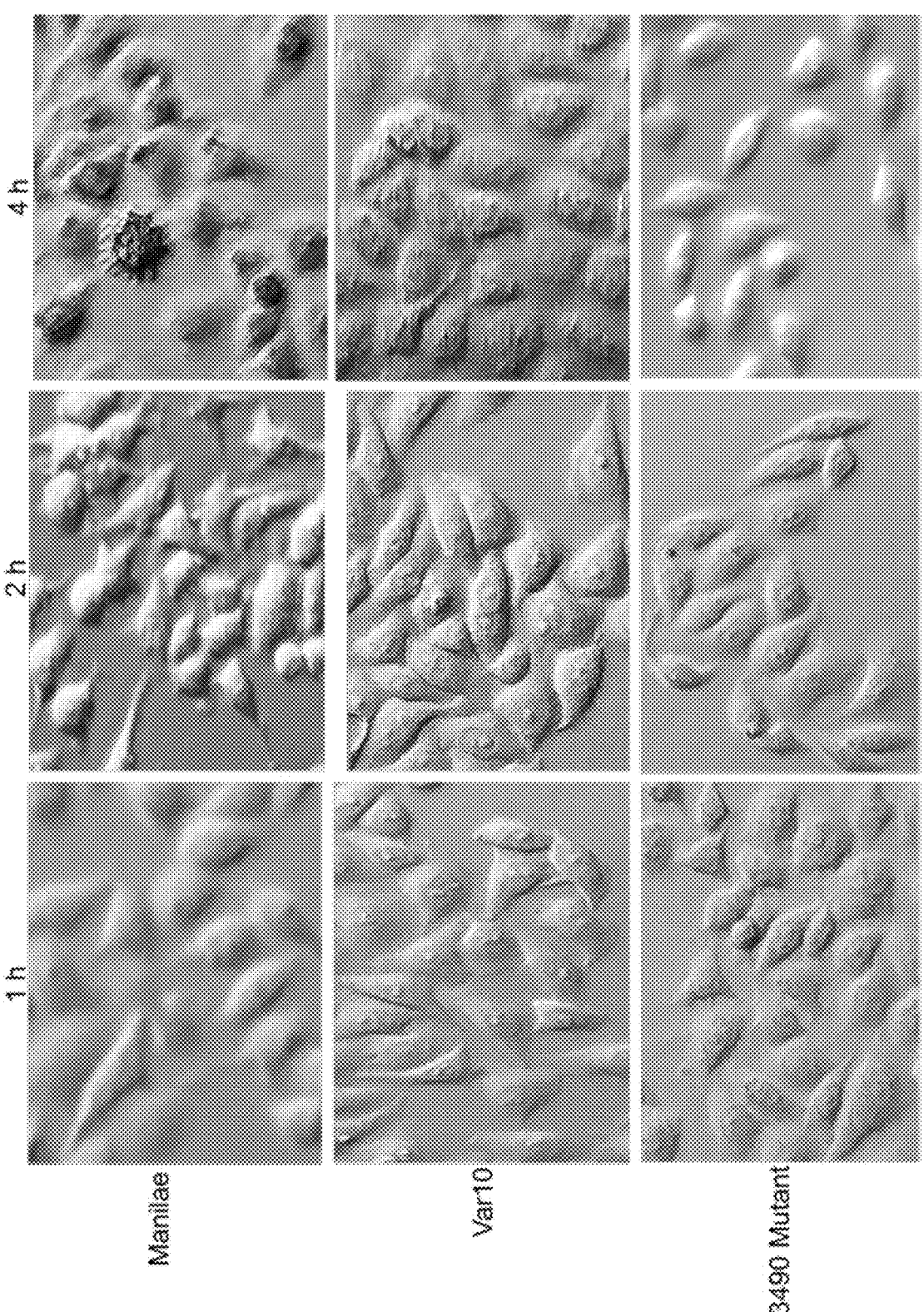

FIG. 7 depicts exemplary images demonstrating the cytopathic effect of in vivo-mimicked (Rat serum, NaCl) *Leptospira* on HeLa cells.

Figure 8:
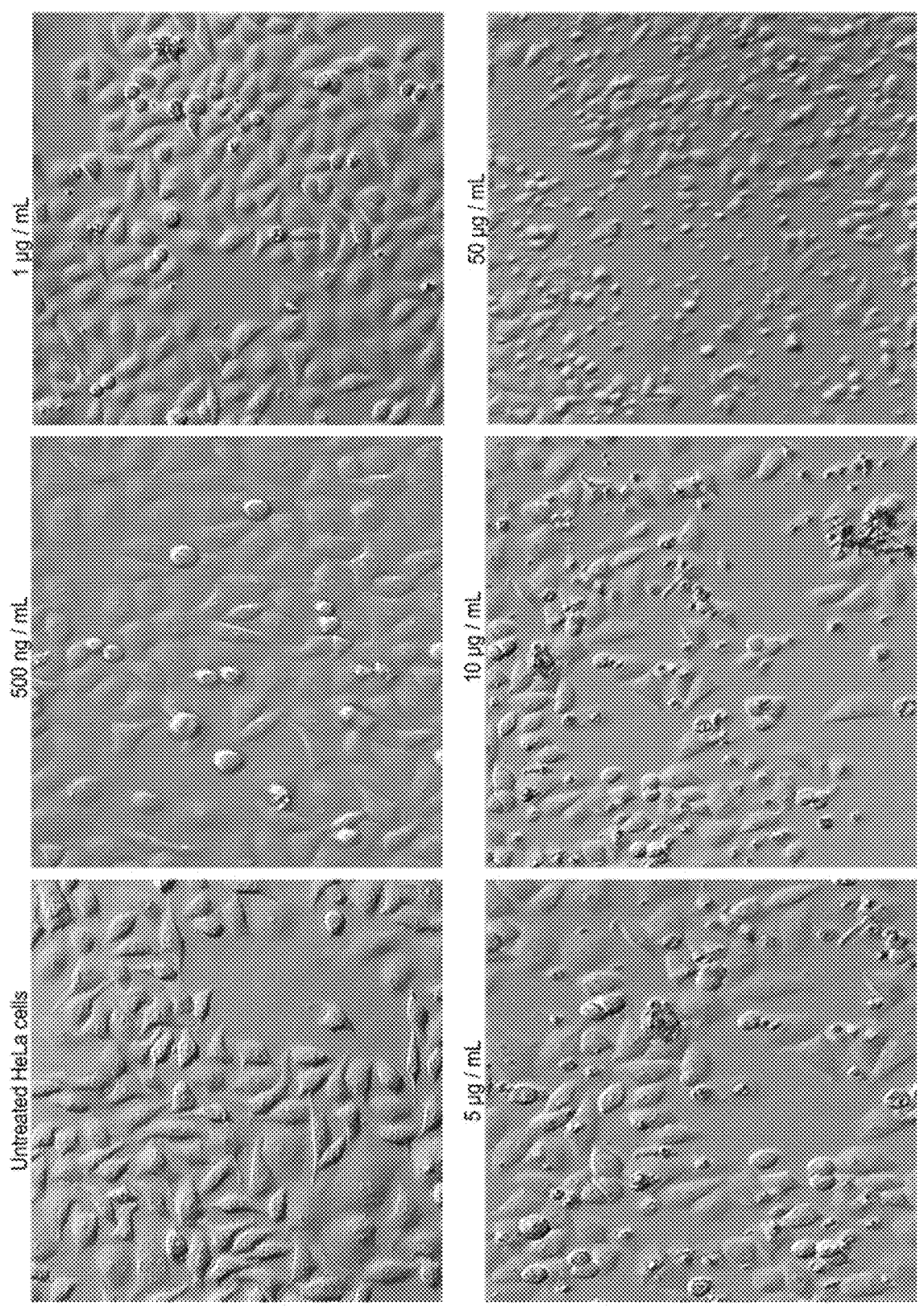

FIG. 8 depicts exemplary images demonstrating that treatment of HeLa cells with soluble rLA_3490_Full reproduces effect of Induced *Leptospira*. 1×10⁶ cells were seeded in 6 wells plate. Images were captured at 4 hours of treatment.

Figure 9:
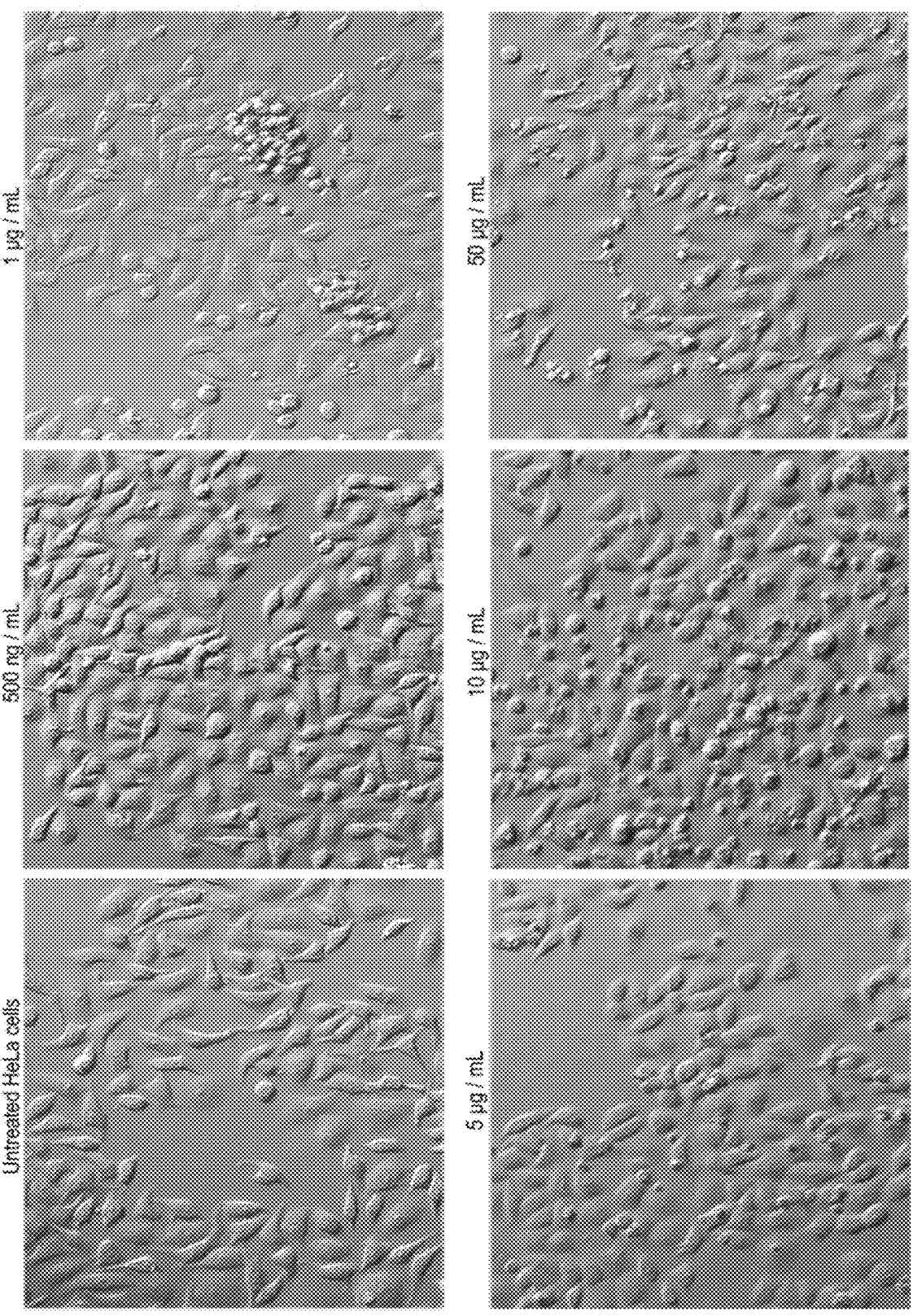

FIG. 9 depicts exemplary images demonstrating the treatment of HeLa cells with soluble rLA_0620_Short.

Figure 10:
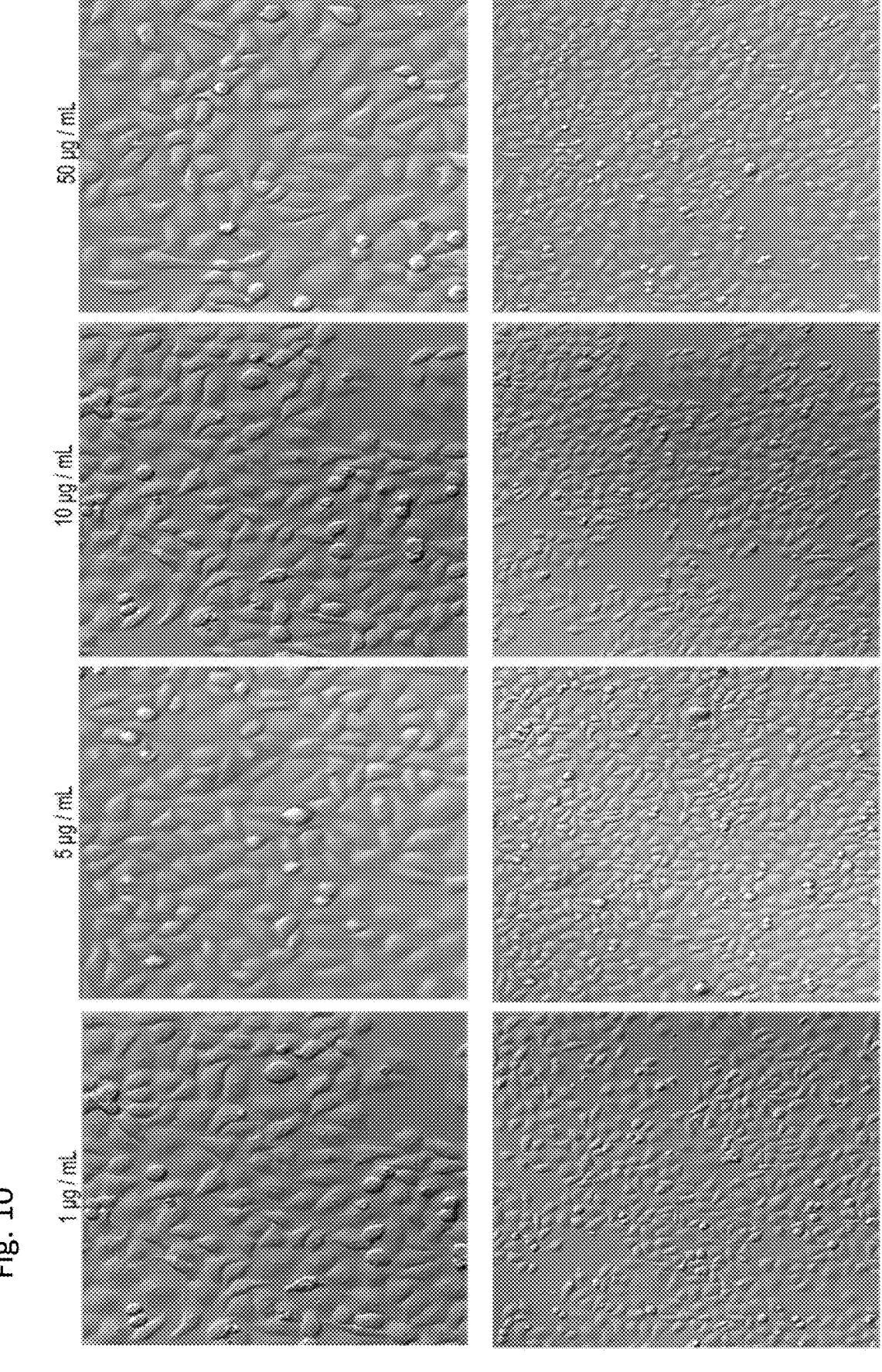

FIG. 10 depicts exemplary images demonstrating the treatment of HeLa cells with BSA as negative control (for endotoxin).

4

Figure 11:
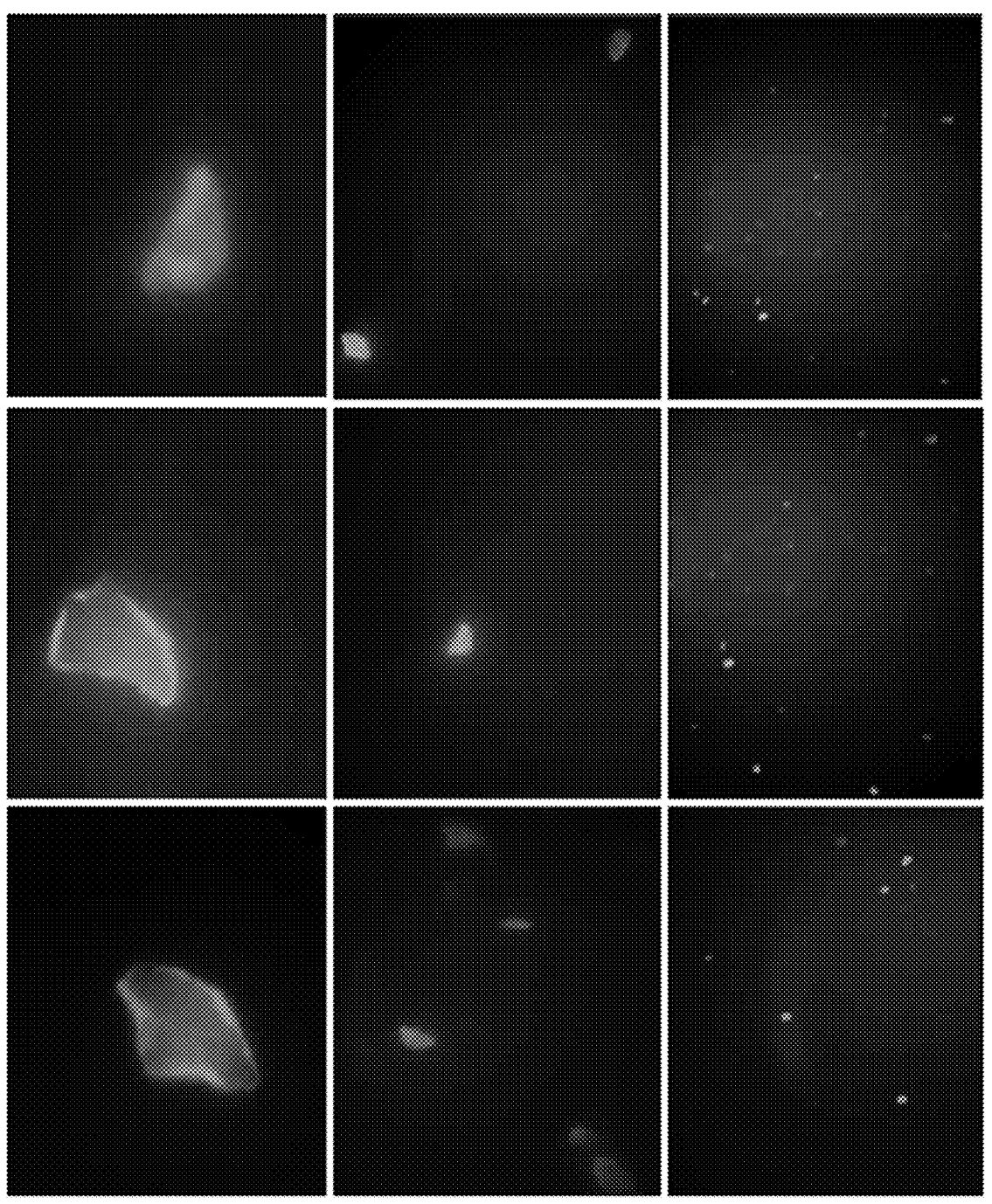

FIG. 11 depicts the binding of recombinant LA_0620 short-mCherry fusion (Ricin B domain alone) to HeLa cells.

Figure 12:
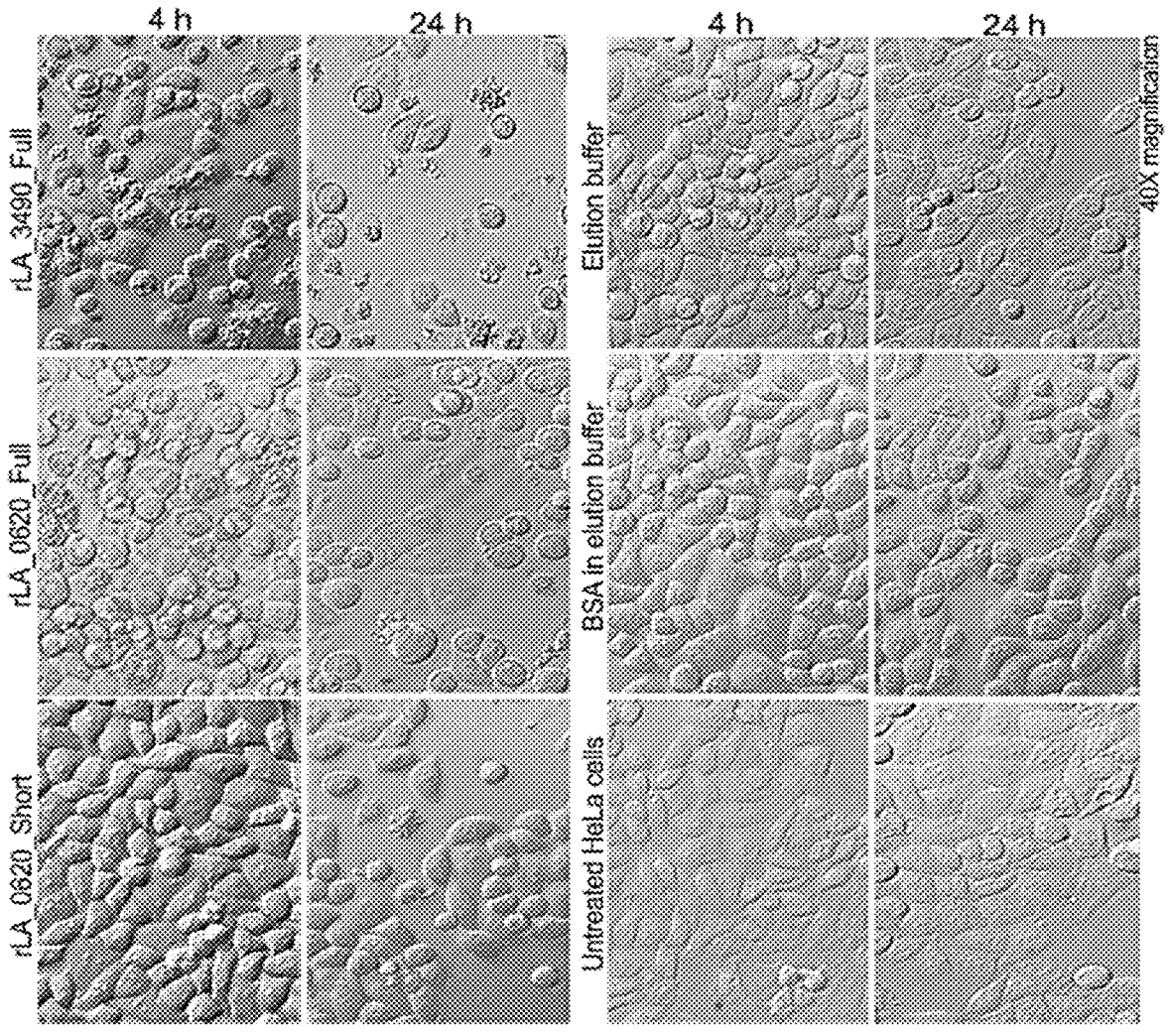

FIG. 12 depicts exemplary images demonstrating the physical and morphological changes of HeLa cells upon treatment with soluble rLA_0620_Short, rLA_0620_Full and rLA_3490_Full.

Figure 13:
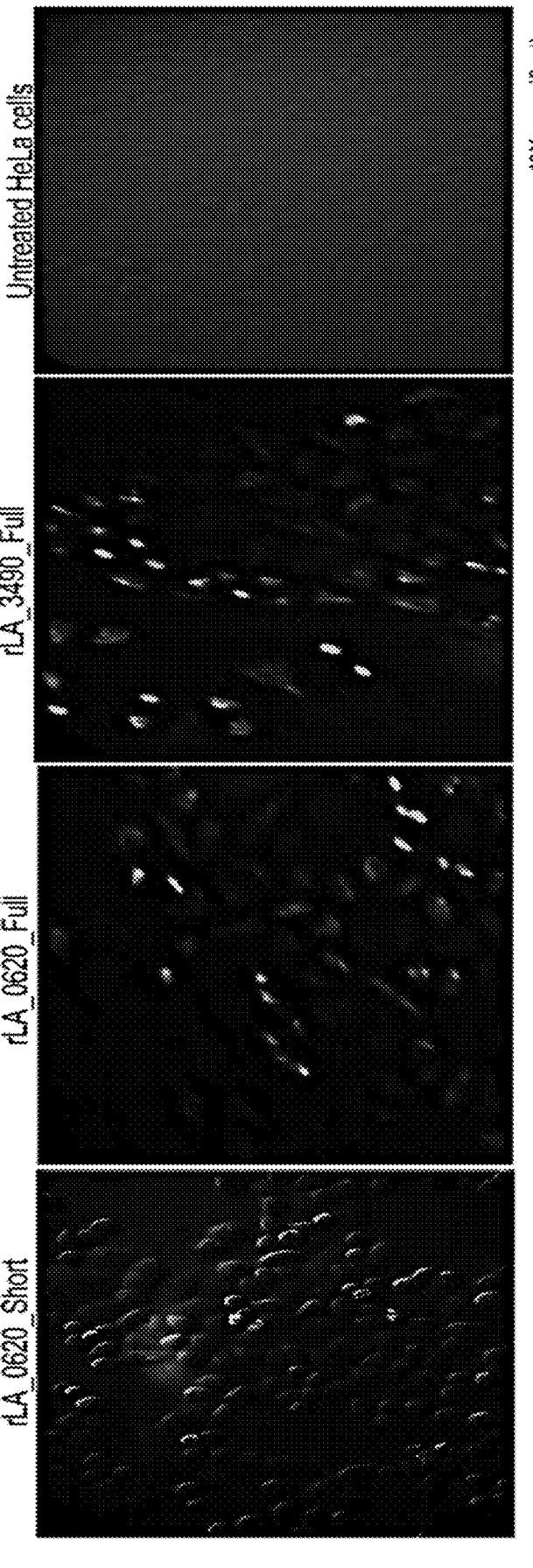

FIG. 13 depicts exemplary images demonstrating the treatment of HeLa cells with soluble rLA_0620_Short, rLA_0620_Full and rLA_3490_Full.

Figure 14:
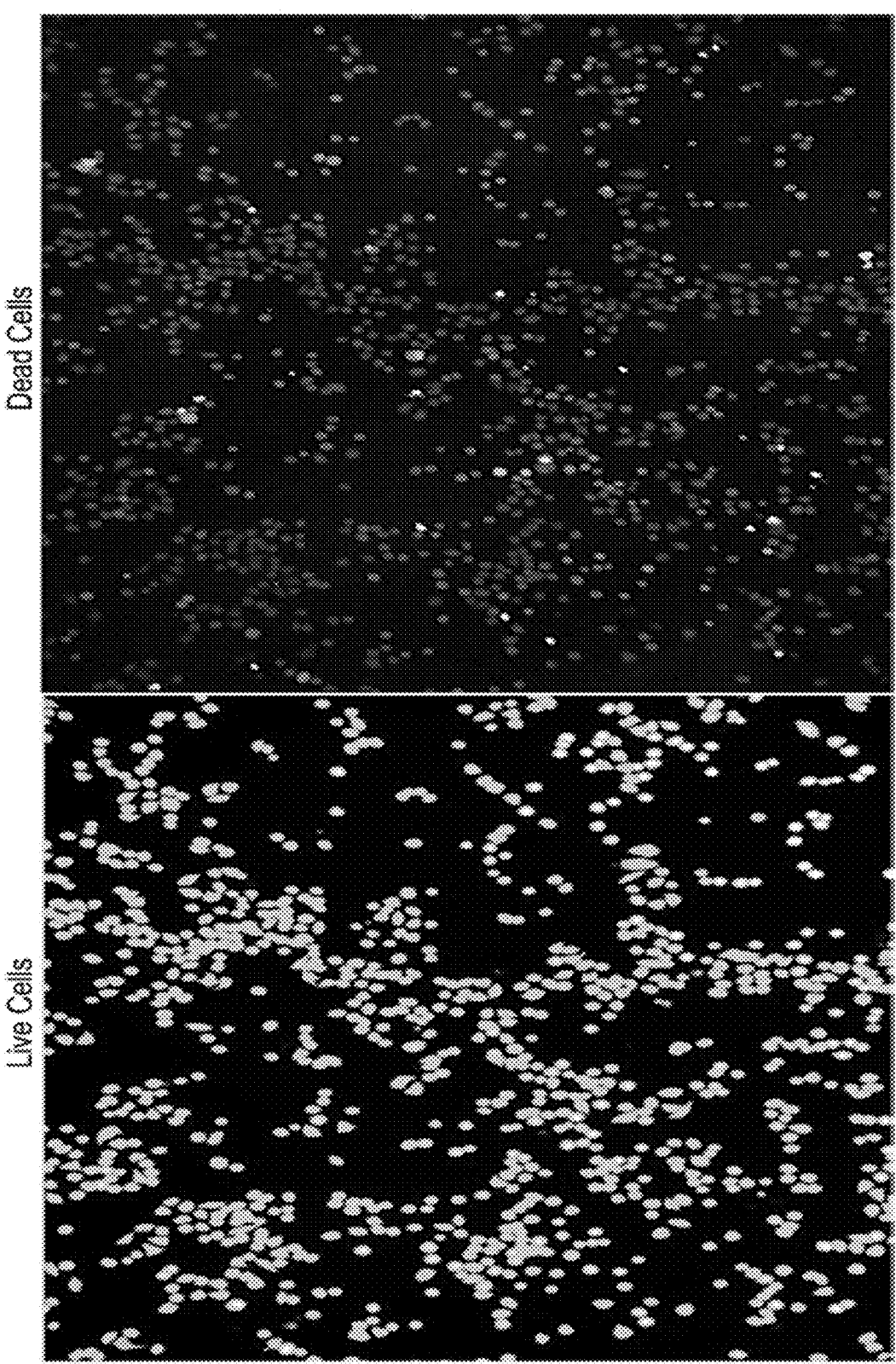

FIG. 14 depicts live dead staining of HeLa cells treated with rLA_0620_Short.

Figure 15:
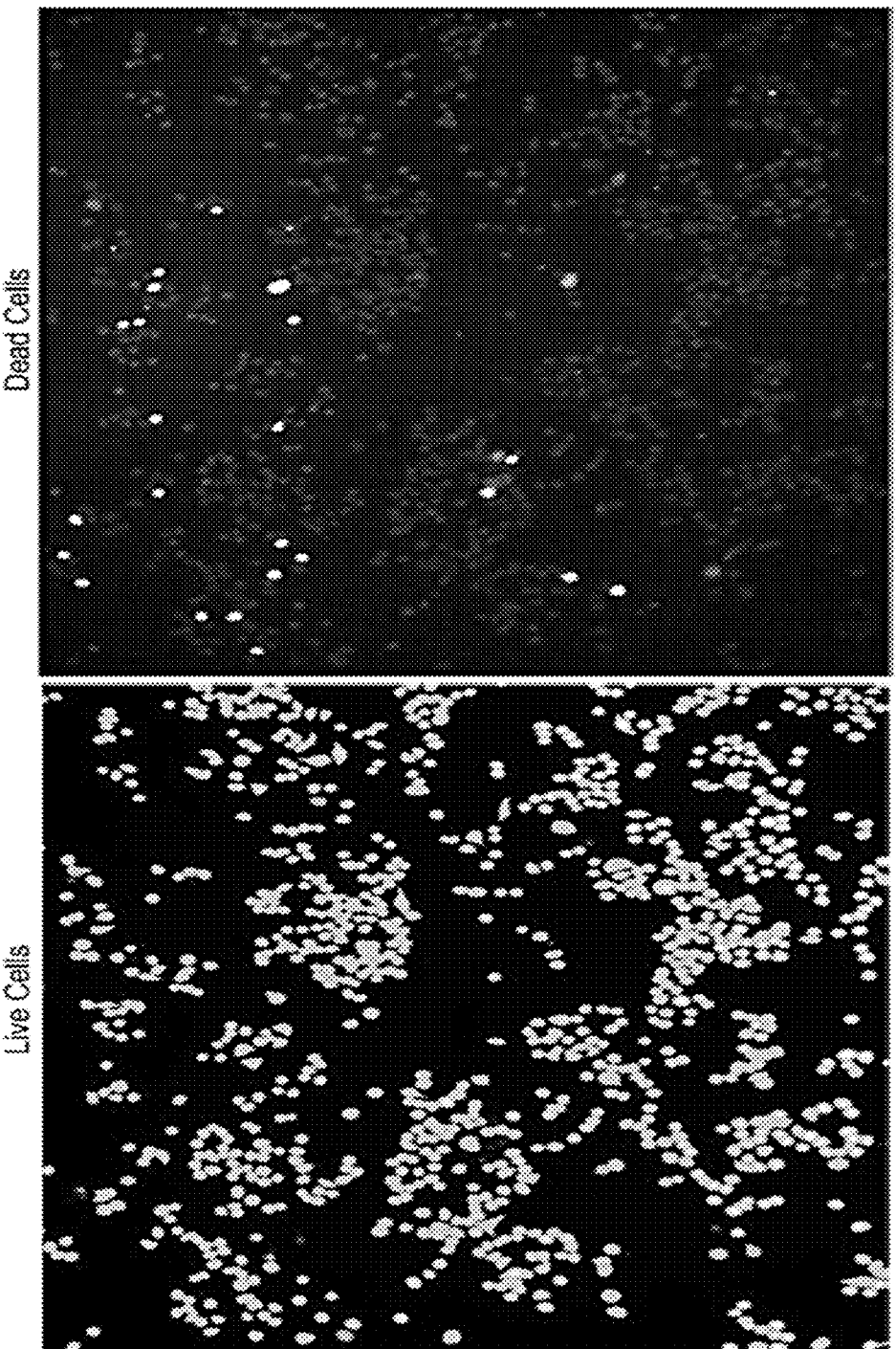

FIG. 15 depicts live dead staining of HeLa cells treated with rLA_0620_Full.

Figure 16:
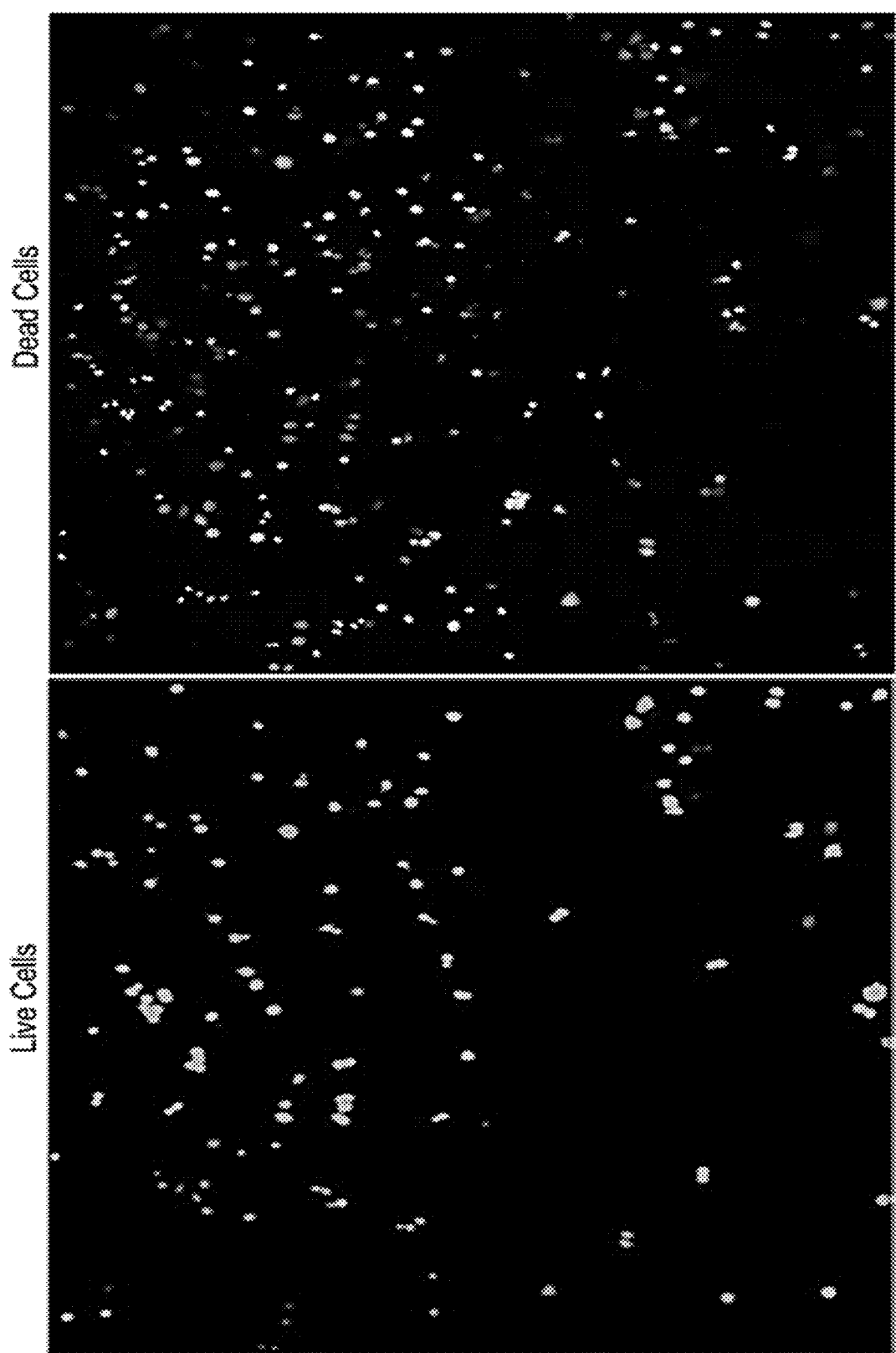

FIG. 16 depicts live dead staining of HeLa cells treated with rLA_3490_Full.

Figure 17:
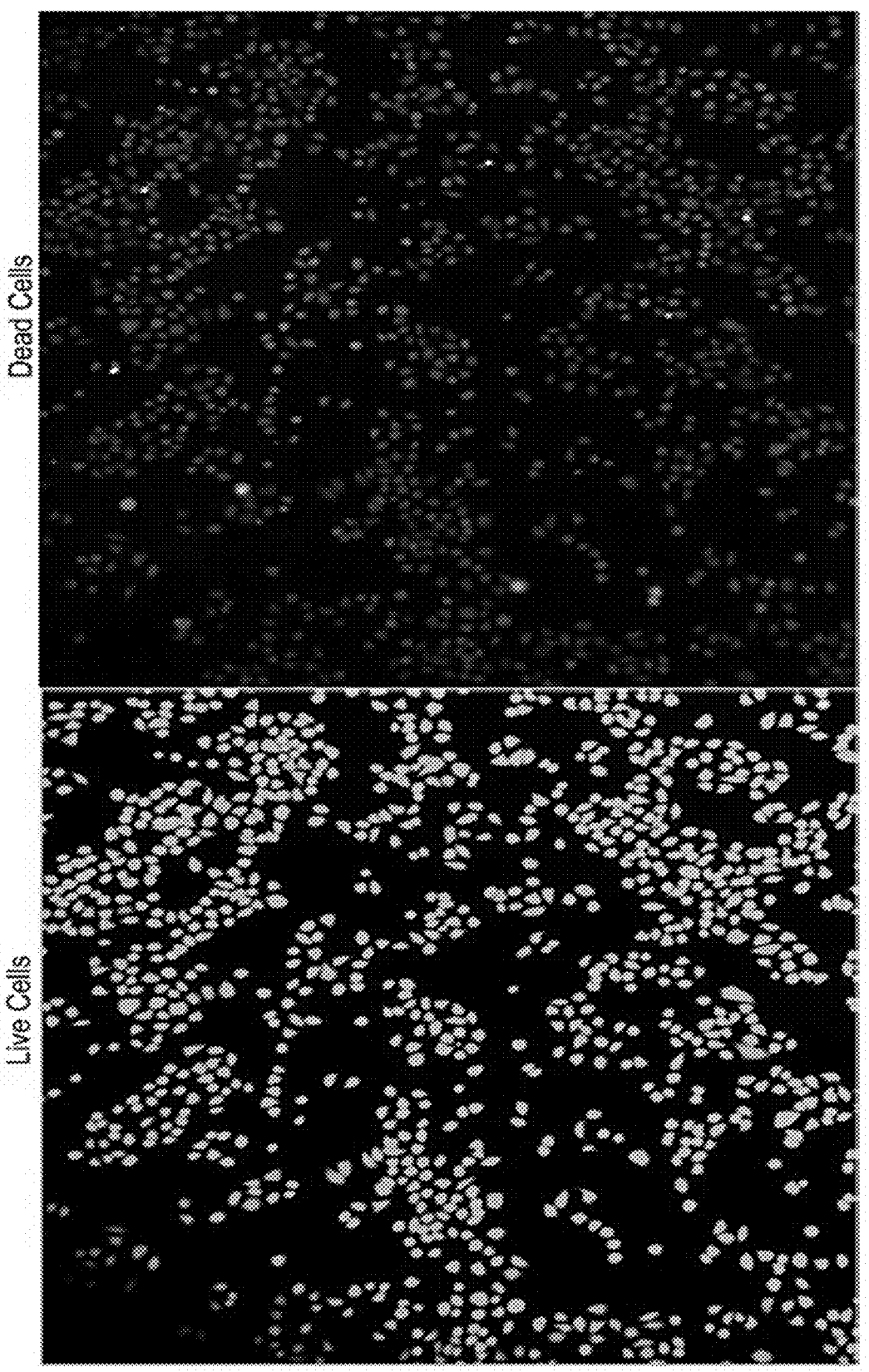

FIG. 17 depicts live dead staining of stained untreated HeLa cells (negative control).

Figure 18:
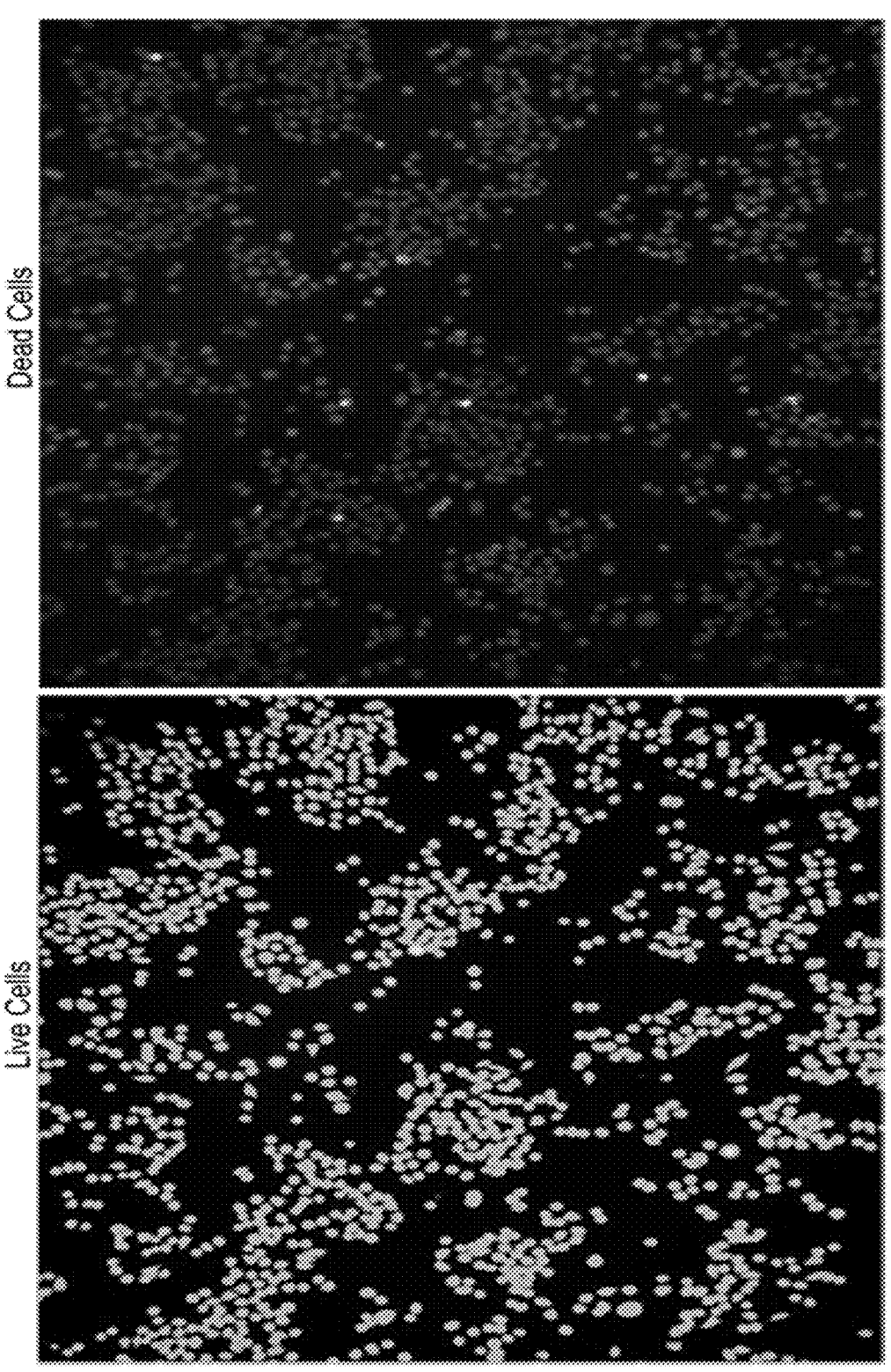

FIG. 18 depicts live dead staining of HeLa cells treated with BSA prepared in elution buffer (negative control).

Figure 19:
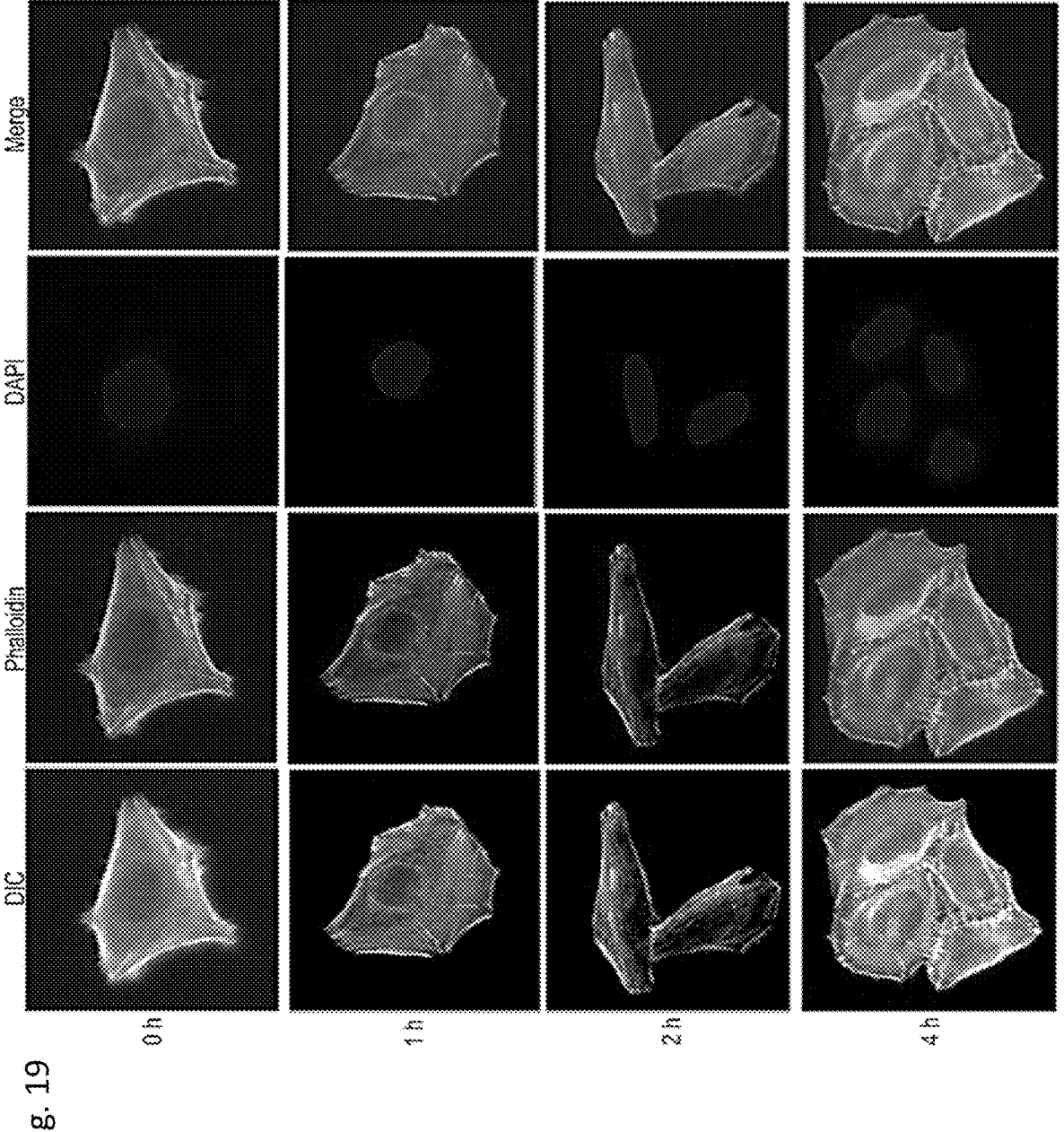

FIG. 19 depicts an analysis of early actin depolymerization in untreated HeLa cells (negative control.)

Figure 20:
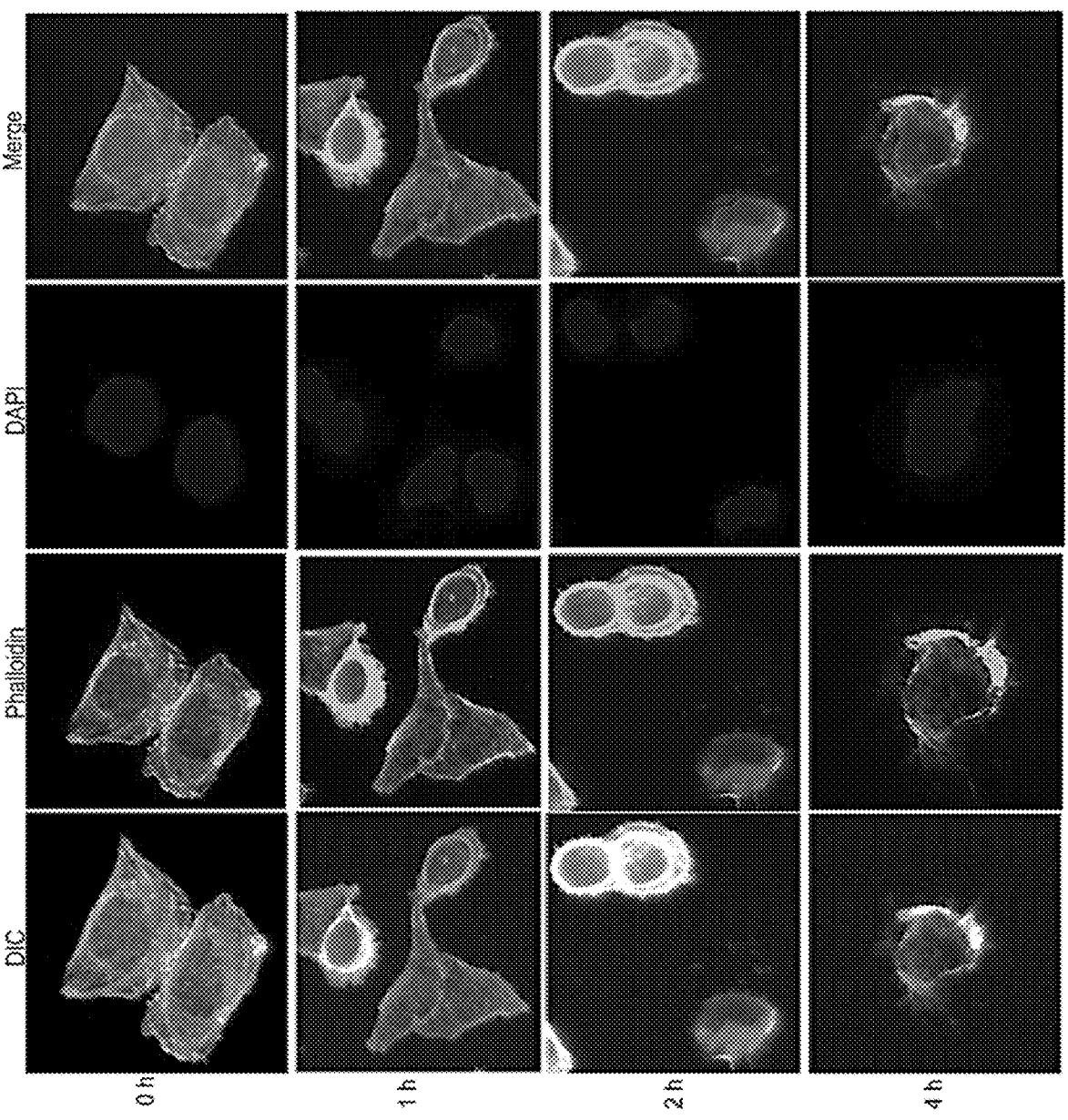

FIG. 20 depicts an analysis of early actin depolymerization in rLA_3490_Full treated HeLa Cells.

Figure 21:
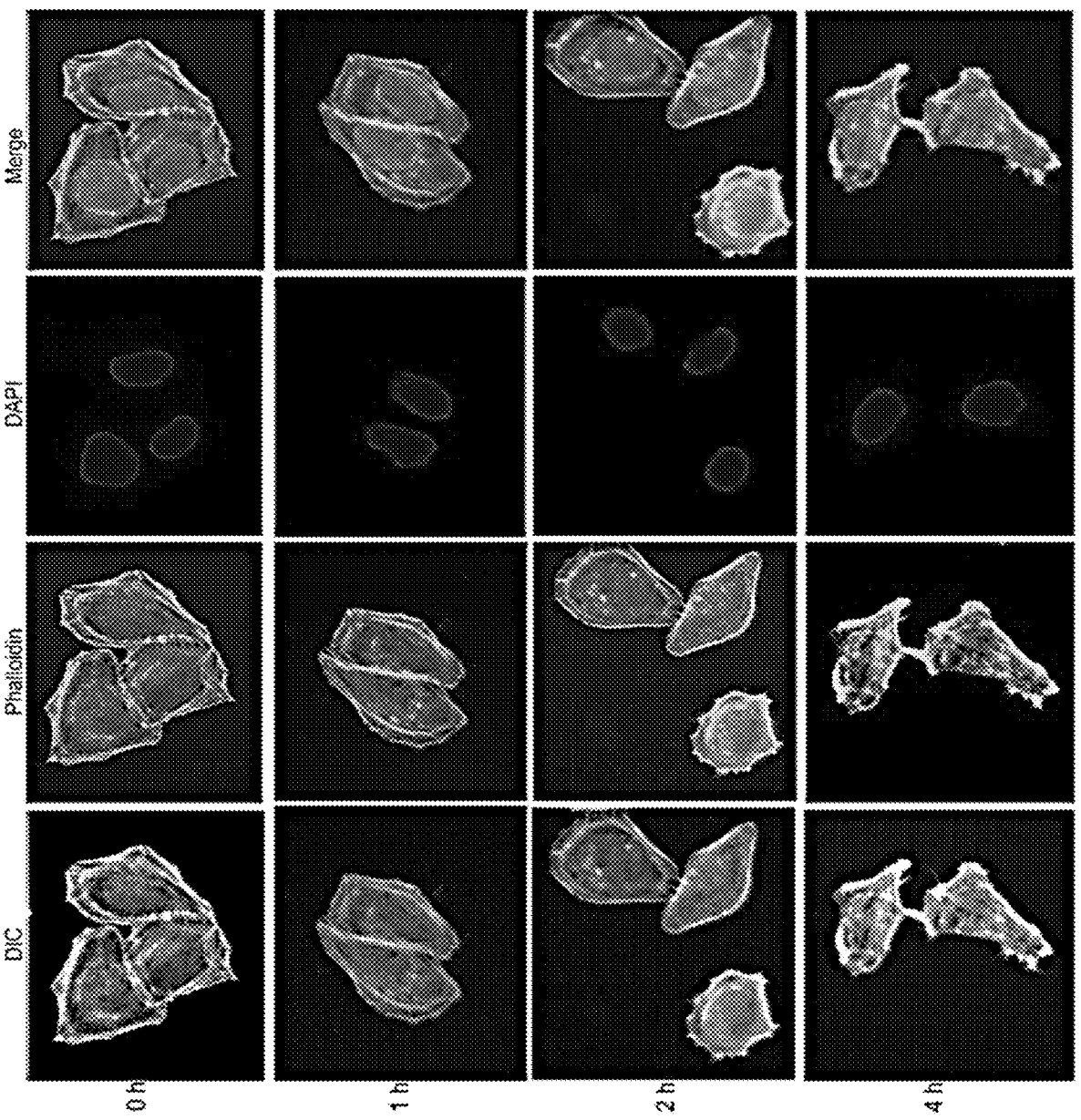

FIG. 21 depicts an analysis of early actin depolymerization in rLA_3490_Short treated HeLa cells (Ricin B domain alone, minimal effect).

Figure 22:
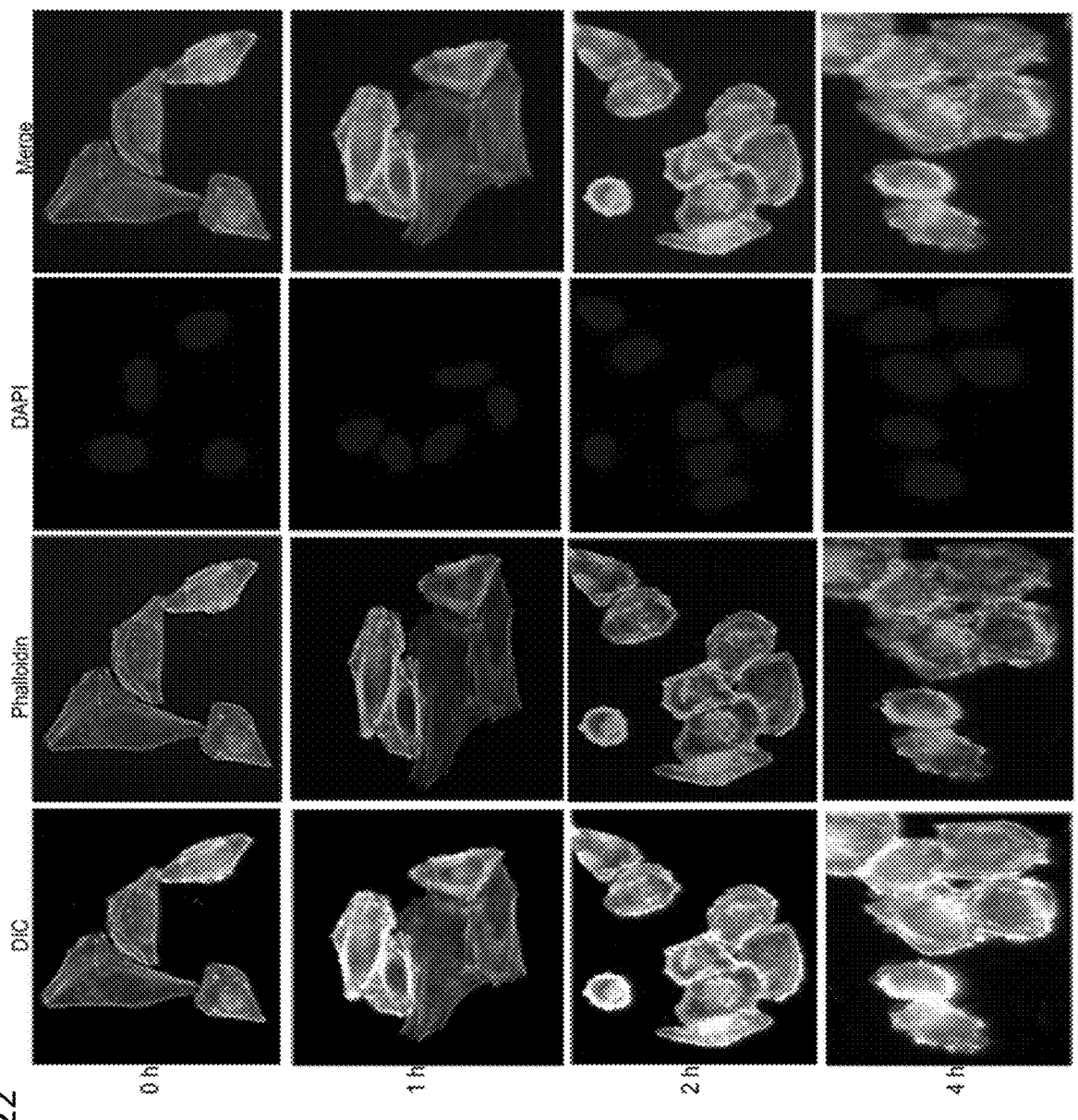

FIG. 22 depicts an analysis of early actin depolymerization in rLA_0620_Full treated HeLa cells.

Figure 23:
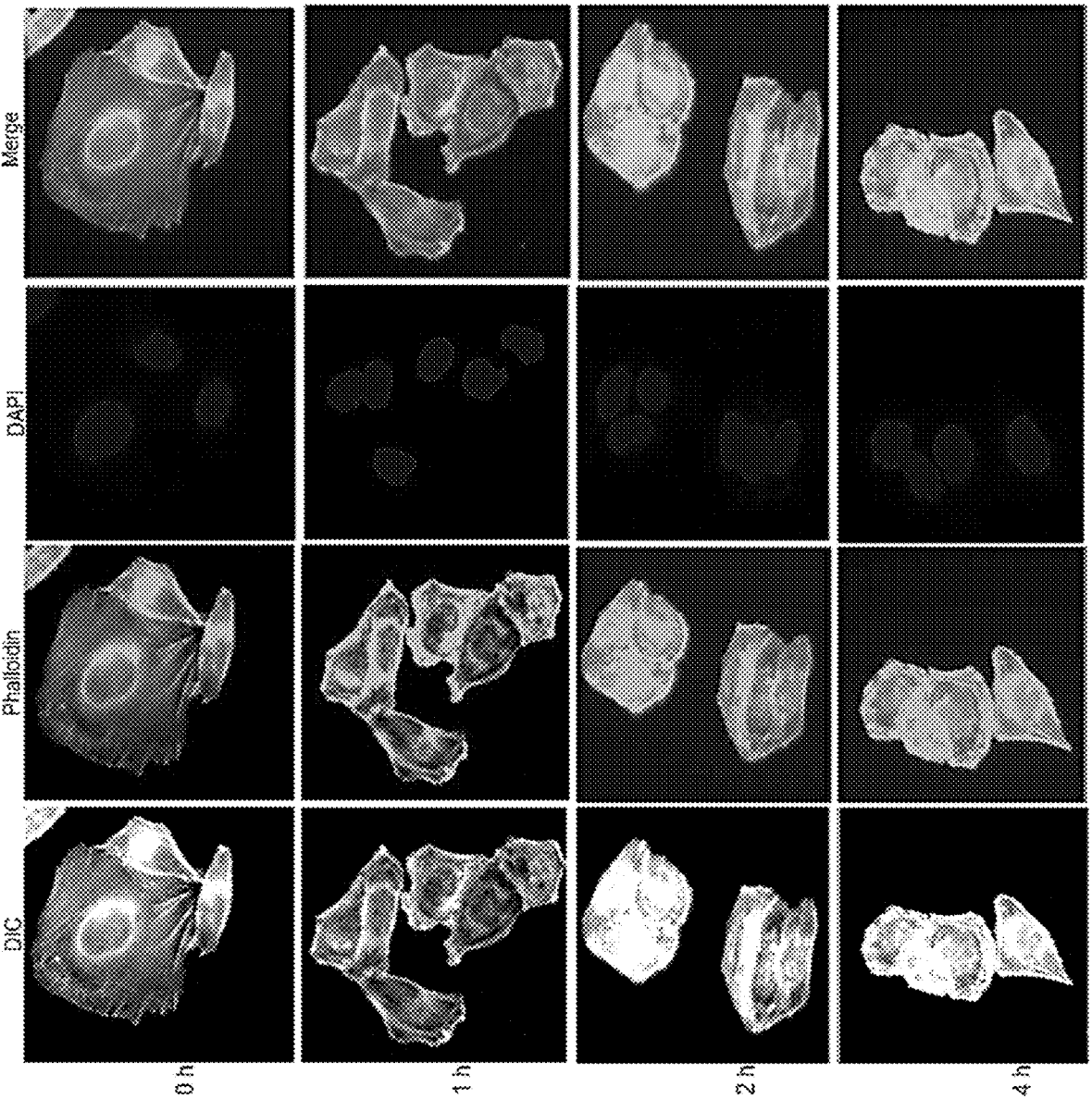

FIG. 23 depicts an analysis of early actin depolymerization in rLA_0620_Short treated HeLa cells (Ricin B domain alone, minimal effect).

Figure 24:
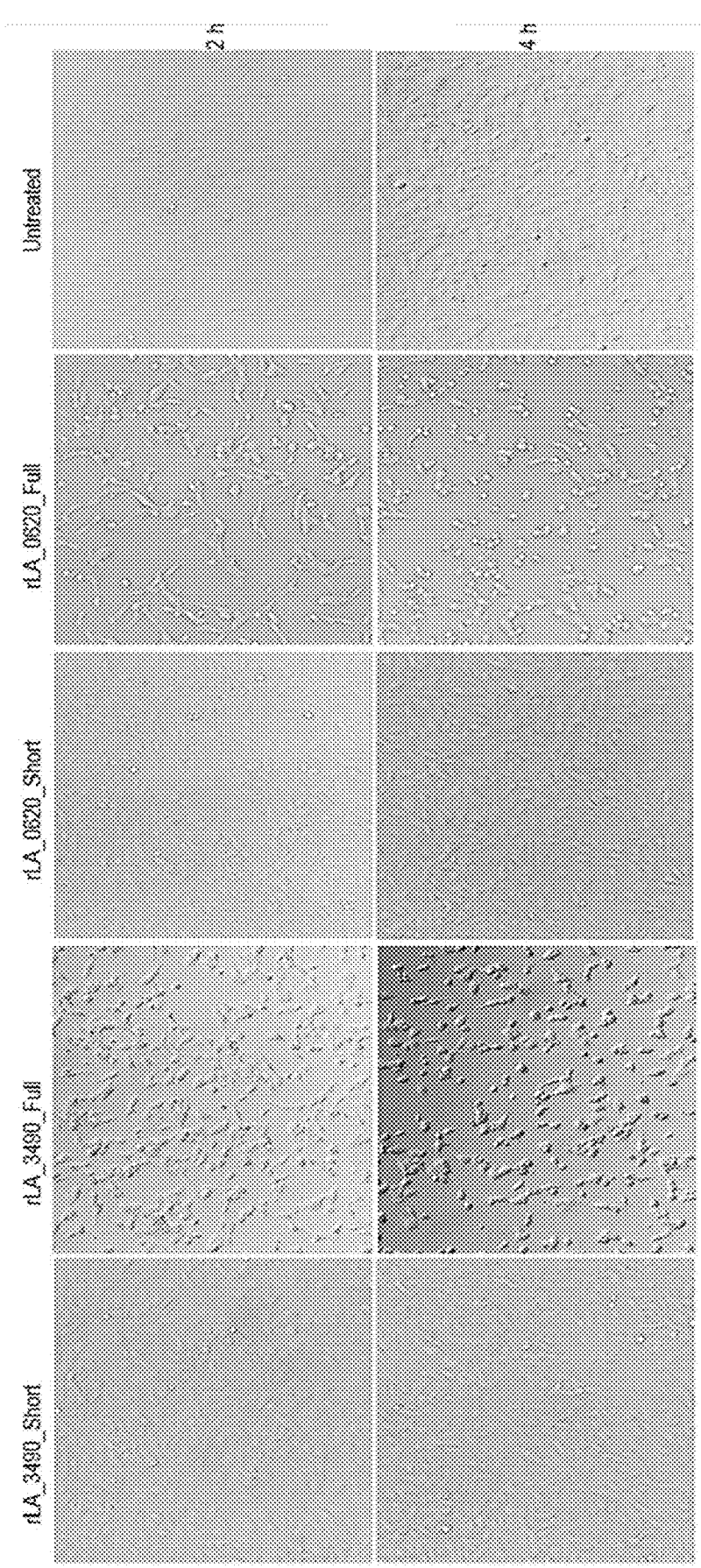

FIG. 24 depicts the cytopathic effect of leptospiral proteins (soluble rLA_3490 and rLA_0620) on U251 glioblastoma cells.

Figure 25:
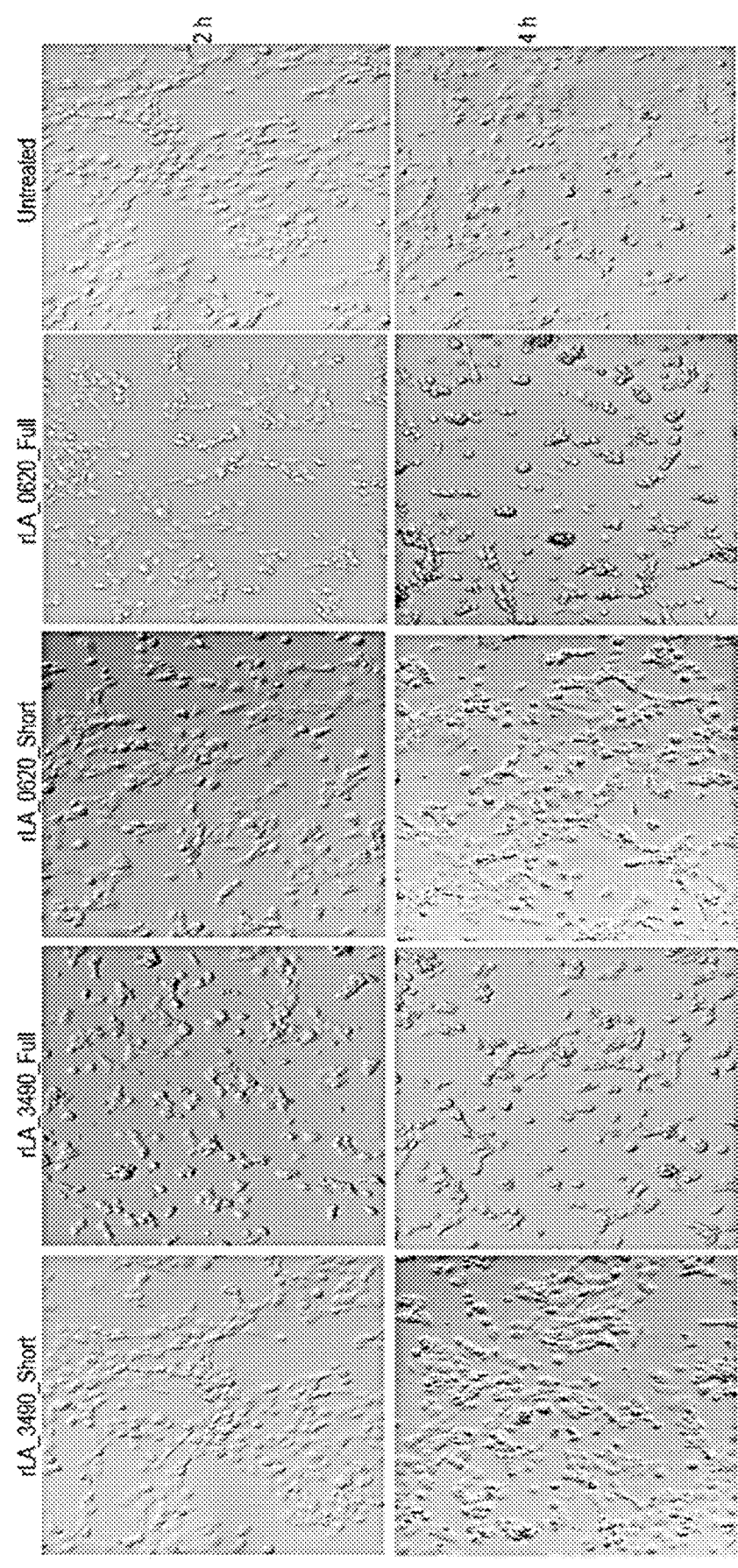

FIG. 25 depicts the cytopathic effect of leptospiral proteins (soluble rLA_3490 and rLA_0620) on astrocytes.

Figure 26:
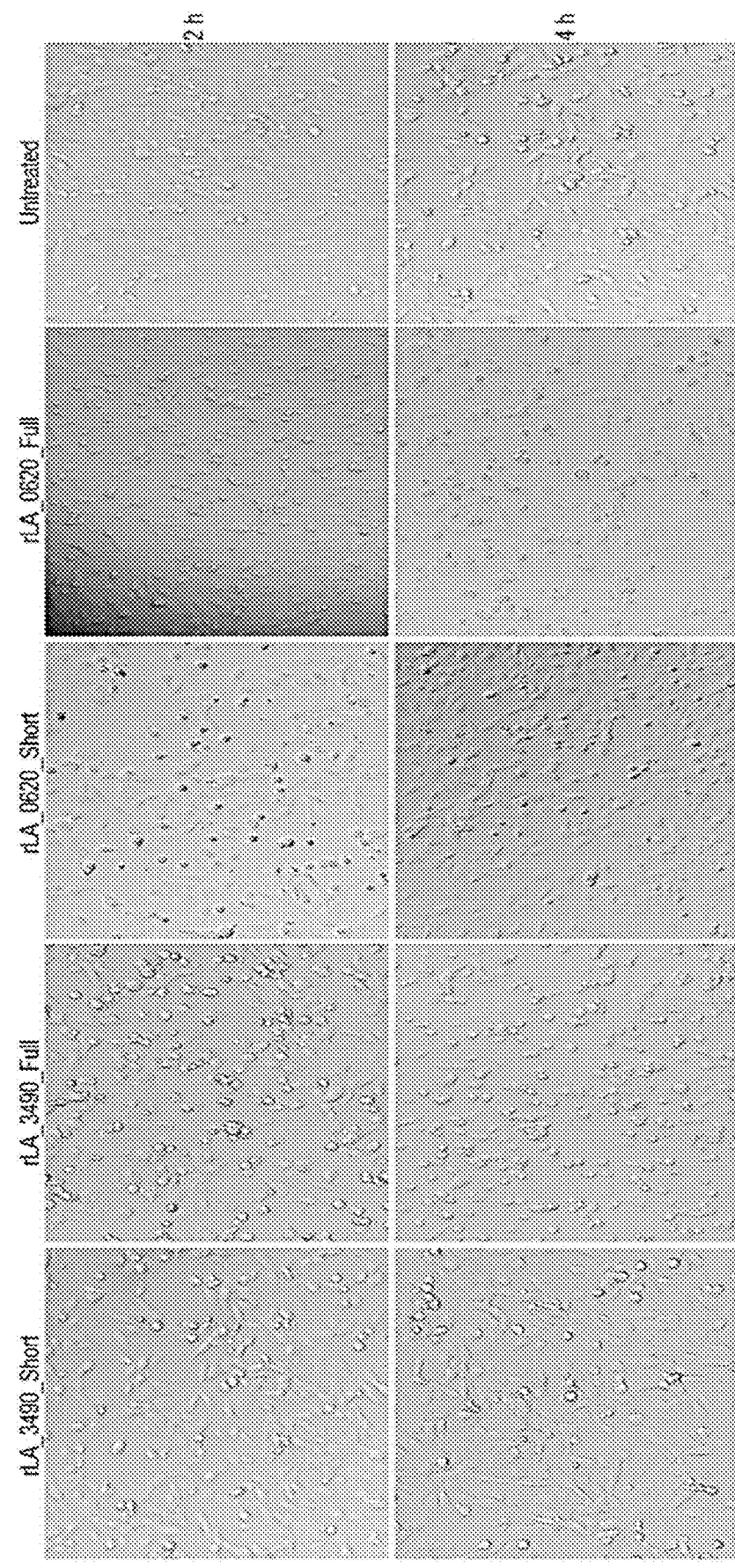

FIG. 26 depicts the cytopathic effect of leptospiral proteins (soluble rLA_3490 and rLA_0620) on endothelial cells.

Figure 27:
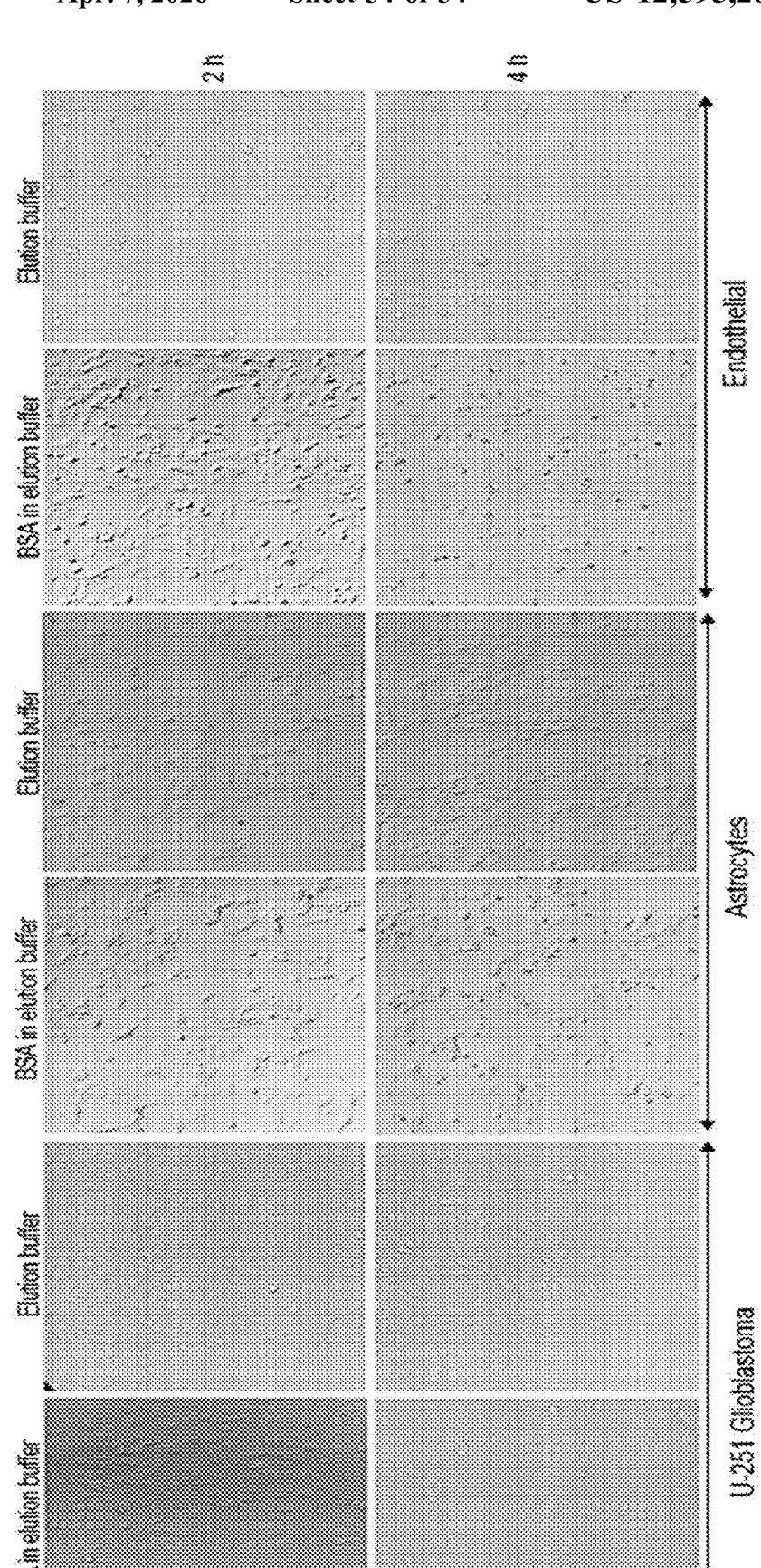

FIG. 27 depicts exemplary images of U251 glioblastoma cells, astrocytes and endothelial cells in elution buffer or BSA in elution buffer (negative controls).

DETAILED DESCRIPTION

The present invention relates to Leptospiral virulence modifying (VM) proteins encoded by the PF07598 *Leptospira* gene family, and variants and fragments thereof. The present invention is based, in part, upon the discovery that Leptospiral VM proteins are cytopathic and thus can be used as a therapeutic agent to induce the cell death of tumor cells. Further, it is demonstrated herein that Leptospiral VM proteins are immunogenic and can thus be used as a vaccine or immunogenic composition to treat or prevent leptospirosis in a subject in need. Further, it is demonstrated herein that Leptospiral VM proteins bind to terminal galactosyl glycoprotein, asialfetunin, and to cell surfaces, and thus can be used as a biological probe.

In one embodiment, the invention provides a composition comprising at least one virulence modifying (VM) protein or a fragment or variant thereof. In one embodiment, the VM protein is LA_0620, or a fragment or variant thereof. In one embodiment, the VM protein is LA_3490, or a fragment or variant thereof.

In another embodiment, the composition of the invention comprises a nucleic acid sequence encoding a VM protein, or a mutant thereof. In another embodiment, the composition of the invention comprises a nucleic acid sequence encoding LA_0620, or a fragment or variant thereof, or a mutant thereof. In one embodiment, the composition of the invention comprises a nucleic acid sequence encoding LA_3490, or a fragment or variant thereof.

In one embodiment the invention provides compositions and methods for inducing or enhancing an immune response. For example, in certain embodiments, the invention relates to inducing or enhancing cell-mediated and/or humoral immunity directed against a desired antigen.

In one embodiment, the composition of the invention serves as an antigen to induce immunity directed against a *Leptospira* sp. bacterium. In certain embodiments, the compositions and methods are used to prevent, treat and diagnose infection by *Leptospira*. In certain embodiments, the compositions and methods are used to prevent or treat a disease or disorder associated with infection by *Leptospira*, including, but not limited to, leptospirosis, kidney damage, meningitis, liver failure, respiratory distress, and even death. In one embodiment, the composition of the invention is a vaccine that induces the cell-mediated and/or humoral immunity directed against at least one *Leptospira* sp protein.

In one embodiment, the compositions of the invention serve as therapeutic agents to treat or prevent a hyperproliferative disease or disorder. In one embodiment, the compositions of the invention are used to treat or prevent tumor growth or metastasis. Therefore, in one embodiment, the invention provides methods of treating or preventing the onset or progression of cancer, comprising administering at least one virulence modifying (VM) proteins or a fragment or variant thereof, or nucleic acid molecule encoding the same, to a subject in need thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from an individual to which it is later to be re-introduced into the same individual.

The term "adjuvant" as used herein is defined as any molecule to enhance an antigen-specific adaptive immune response.

The term "agent" includes any substance, metabolite, molecule, element, compound, or a combination thereof. It includes, but is not limited to, e.g., protein, oligopeptide, small organic molecule, glycan, polysaccharide, polynucleotide, and the like. It can be a natural product, a synthetic compound, a chemical compound, or a combination of two or more substances. Unless otherwise specified, the terms "agent," "substance," and "compound" can be used interchangeably. Further, a "test agent" or "candidate agent" is generally a subject agent for use in an assay of the invention.

The term "binding" refers to a direct association between at least two molecules, due to, for example, covalent, electrostatic, hydrophobic, ionic and/or hydrogen-bond interactions.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

A "chimeric antibody" refers to a type of engineered antibody which contains a naturally-occurring variable region (light chain and heavy chains) derived from a donor antibody in association with light and heavy chain constant regions derived from an acceptor antibody.

"Contacting" refers to a process in which two or more molecules or two or more components of the same molecule or different molecules are brought into physical proximity such that they are able undergo an interaction. Molecules or components thereof may be contacted by combining two or more different components containing molecules, for example by mixing two or more solution components, preparing a solution comprising two or more molecules such as target, candidate or competitive binding reference molecules, and/or combining two or more flowing components.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap temporally with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared multiplied by 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

As used herein, an "inhibitory-effective amount" is an amount that results in a detectable (e.g., measurable) amount of inhibition of an activity. In some instance, the activity is its ability to bind with another component.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

"Parenteral" administration of an immunogenic composition includes, e.g., subcutaneous (s.c.), intravenous (i.v.), intramuscular (i.m.), or intradermal (i.d.) injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "X," the presence of a molecule containing epitope X (or free, unlabeled A), in a reaction containing labeled "X" and the antibody, will reduce the amount of labeled X bound to the antibody.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "therapeutic" as used herein means a treatment and/or prophylaxis. A therapeutic effect is obtained by suppression, diminution, remission, or eradication of a disease state.

The term "therapeutically effective amount" refers to the amount of the subject compound that will elicit the biological or clinical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to Leptospiral virulence modifying (VM) proteins encoded by the PF07598 *Leptospira* gene family, and variants and fragments thereof.

In some embodiments, the present invention provides a composition comprising a Leptospiral VM protein, variant thereof, or fragment thereof. In some embodiment, the composition comprises a fragment of a Leptospiral VM protein. For example, in one embodiment, the composition comprises a fragment of a Leptospiral VM protein, wherein the fragment comprises a Ricin B-like domain of a Leptospiral VM protein.

In one embodiment, the composition comprises a fusion protein, comprising a first domain comprising a Leptospiral VM protein, variant thereof, or fragment thereof. In one embodiment, the fusion protein comprises a second domain. In one embodiment, the second domain is a targeting domain, wherein the targeting domain directs the fusion protein to a specific cell or tissue of interest. For example, in one embodiment, the targeting domain comprises an antibody, antibody fragment, or peptide that specifically binds to an antigen (e.g., tumor antigen) thereby directing the fusion protein to a cell or tissue expressing the antigen. In one embodiment, the second domain comprises a detectable protein or peptide (e.g., a fluorescent protein) that allows for the visualization of the fusion protein.

In one embodiment, the present invention provides an isolated nucleic acid molecule encoding a Leptospiral VM protein, variant thereof, or fragment thereof. In some embodiments, the isolated nucleic acid molecule comprises DNA, cDNA, RNA, or mRNA encoding a Leptospiral VM protein, variant thereof, or fragment thereof. In one embodiment, the isolated nucleic acid molecule encodes a fusion protein comprising a Leptospiral VM protein, variant thereof, or fragment thereof.

In one embodiment, the composition comprises an immunological composition comprising (a) a Leptospiral VM protein, variant thereof, or fragment thereof or (b) a nucleic acid molecule encoding a Leptospiral VM protein, variant thereof, or fragment thereof. As demonstrated herein, in certain embodiments, a Leptospiral VM protein, variant thereof, or fragment thereof induces a protective immune response that can treat or prevent Leptospiral infection or leptospirosis in a subject in need thereof. In one embodiment, the immunological composition comprises a vaccine. In one embodiment, the immunological composition comprises a bacterium (e.g., a bacterium from genus *Leptospira*) modified to express a Leptospiral VM protein, variant thereof, or fragment thereof. In one embodiment, the bacterium is attenuated in that it has reduced pathogenicity, but is capable of inducing a protective immune response. The compositions are not only useful as a prophylactic therapeutic agent for immunoprotection, but are also useful as a therapeutic agent for treatment of an ongoing infection, disease, or disorder.

In one embodiment, the present invention relates to methods of inducing cell death or damage comprising administering to a cell a composition comprising (a) a Leptospiral VM protein, variant thereof, or fragment thereof; or (b) a nucleic acid molecule encoding a Leptospiral VM protein, variant thereof, or fragment thereof. For example, as demonstrated herein, Leptospiral VM proteins are cytopathic proteins. In one embodiment, the method comprises administering the composition to a tumor, thereby inducing tumor cell death or damage.

The present invention also provides methods of preventing, inhibiting, and treating infection caused by bacteria of genus *Leptospira* in a subject in need thereof. In one embodiment, the methods of the invention induce immunity against genus *Leptospira* in the subject, by generating an immune response in the subject directed to a Leptospiral VM protein. In certain embodiments, the method induces broad immunity across genus *Leptospira*. In one embodiment, the methods of the invention induce production of VM protein-specific antibodies in the subject. In one embodiment, the methods of the invention prevent *Leptospira* related pathology, such as leptospirosis (also known as Weil's disease) in a subject in need thereof. In one embodiment, the methods of the invention comprise administering to the subject a composition comprising a) a Leptospiral VM protein, variant thereof, or fragment thereof; or (b) a nucleic acid molecule encoding a Leptospiral VM protein, variant thereof, or fragment thereof Compositions The present invention provides compositions comprising or encoding a Leptospiral VM protein, variant thereof, or fragment thereof.

In one embodiment, the composition comprises a Leptospiral VM protein comprising the amino acid sequence of SEQ ID NO:1 (minus the signal peptide of LA_0620; full length expressed in pET32b+*E. coli* expression vector.)

In one embodiment, the composition comprises a Leptospiral VM protein comprising the amino acid sequence of SEQ ID NO:2 (minus the signal peptide of LA_3490; full length expressed in pET32b+*E. coli* expression vector.).

In certain embodiments, the composition comprises a fragment of a Leptospiral VM protein. For example, in one embodiment, the composition comprises a Ricin B-like domain of a Leptospiral VM protein.

In certain embodiments, the composition comprises a fragment of a Leptospiral VM protein. For example, in one embodiment, the composition comprises a Ricin B-like domain of any of the defined or structurally predicted (PHYRE2) Leptospiral VM proteins.

In one embodiment, the composition comprises a portion of a Leptospiral VM protein, LA_0620, comprising the predicted Ricin B-like domain having an amino acid sequence of SEQ ID NO:3.

In one embodiment, the composition comprises a Leptospiral VM protein LA_3490, comprising the predicted Ricin B-like domain with an amino acid sequence as set forth in SEQ ID NO:4.

In one embodiment, the amino acid sequence of the LA_0620 (full)-mCherry Fusion protein including Gly4Ser linkers and an enterokinase cleavage site (DDDDK; SEQ ID NO:5) is set forth in SEQ ID NO:6.

In one embodiment, the amino acid sequence of the LA_3490 (full)-mCherry Fusion protein including Gly4Ser linkers and an enterokinase cleavage site (DDDDK; SEQ ID NO:5) is set forth in SEQ ID NO:7.

In various embodiments, the invention provides a protein, or a fragment, a homolog, a mutant, a variant, a derivative or a salt of a protein as elsewhere described herein, wherein the activity of the various domains of Leptospiral VM proteins (e.g., immunogenic activity or cytopathic activity or activity related to Leptospiral VM protein mechanism of action) is retained.

Proteins or peptides of the present invention can be prepared using well known techniques. For example, the proteins can be prepared synthetically, using either recombinant DNA technology or chemical synthesis. Proteins of the present invention may be synthesized individually or as longer proteins composed of two or more proteins. The proteins of the present invention can be isolated, i.e., substantially free of other naturally occurring host cell proteins and fragments thereof.

The proteins of the present invention may contain modifications, such as glycosylation, aglycosylation, side chain oxidation, or phosphorylation; so long as the modifications do not destroy the immunologic activity of the proteins. Other modifications include incorporation of D-amino acids or other amino acid mimetics that can be used, for example, to increase the serum half-life of the proteins.

The proteins of the invention can be modified whereby the amino acid is substituted for a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note that the parenthetic letters indicate the one-letter codes of amino acids. As used herein, X stands for any amino acid.

The present invention should also be construed to encompass "mutants," "derivatives," and "variants" of the proteins of the invention (or of the DNA encoding the same) which mutants, derivatives and variants are polypeptides which are altered in one or more amino acids (or, when referring to the nucleotide sequence encoding the same, are altered in one or more base pairs) such that the resulting protein (or DNA) is not identical to the sequences recited herein, but has the same biological property as the protein disclosed herein.

The invention should also be construed to include any form of a protein variant having substantial homology to an amino acid sequence disclosed herein. In one embodiment, a protein variant is at least about 50%, 70%, 80%, 85%, 86%, 87%, 88%, 89%, 90%, 91%, 92%, 93%, 94%, 95%, 96%, 97%, 98%, or 99% homologous to an amino acid sequence disclosed herein.

The invention should also be construed to include any form of a fragment having a substantial length of an amino acid sequence disclosed herein. In one embodiment, a fragment is at least about 50%, 70%, 80%, 85%, 86%, 87%, 88%, 89%, 90%, 91%, 92%, 93%, 94%, 95%, 96%, 97%, 98%, or 99% of the length of an amino acid sequence disclosed herein.

The invention should also be construed to include any form of a fragment of a protein variant, having both substantial homology to and a substantial length of an amino acid sequence disclosed herein. In one embodiment, a fragment of a protein variant is at least about 50%, 70%, 80%, 85%, 86%, 87%, 88%, 89%, 90%, 91%, 92%, 93%, 94%, 95%, 96%, 97%, 98%, or 99% homologous to an amino acid sequence disclosed herein, and is at least about 50%, 70%, 80%, 85%, 86%, 87%, 88%, 89%, 90%, 91%, 92%, 93%, 94%, 95%, 96%, 97%, 98%, or 99% of the length of an amino acid sequence disclosed herein.

The protein may alternatively be made by recombinant means or by cleavage from a longer protein. The protein may be confirmed by amino acid analysis or sequencing.

The variants of the proteins according to the present invention may be (i) one in which one or more of the amino acid residues are substituted with a conserved or non-conserved amino acid residue (e.g., a conserved amino acid residue) and such substituted amino acid residue may or may not be one encoded by the genetic code, (ii) one in which there are one or more modified amino acid residues, e.g., residues that are modified by the attachment of substituent groups, (iii) one in which the protein comprises an alternative splice variant of the proteins or domains described herein, (iv) fragments of the proteins or domains described herein and/or (v) one in which the protein is fused with another protein or peptide, such as a leader or secretory sequence or a sequence which is employed for purification (for example, His-tag) or for detection (for example, Sv5 epitope tag). The fragments include proteins or peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one peptide to a sequence of a second peptide. Variants are defined to include peptide sequences different from the original sequence, e.g., different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, or 95% similar or identical to the original amino acid sequence. The degree of identity between two peptides may be determined using computer algorithms and methods that are widely known for the persons skilled in the art. The identity between two amino acid sequences may be determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The protein of the invention may or may not be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction. A polypeptide or protein of the invention may be phosphorylated using conventional methods such as the method described in Reedijk et al. (The EMBO Journal 11(4):1365, 1992).

The protein of the invention may include unnatural amino acids formed by post-translational modification or by introducing unnatural amino acids during translation. A variety of approaches are available for introducing unnatural amino acids during polypeptide translation.

A protein of the invention may be conjugated with other molecules, such as polyethylene glycol (PEG). This may be accomplished by inserting cysteine mutations or unnatural amino acids that can be modified with a chemically reactive PEG derivative. In one embodiment, the protein is conjugated to other proteins, to prepare fusion proteins. This may be accomplished, for example, by the synthesis of N-terminal or C-terminal fusion proteins provided that the resulting fusion protein retains the functionality of the protein described herein.

Cyclic derivatives of the proteins of the invention are also part of the present invention. Cyclization may allow the protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzenecontaining amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic protein which is more flexible than the cyclic proteins containing peptide bond linkages as described above. A more flexible protein may be prepared by introducing cysteines at the right and left position of the polypeptide and forming a disulfide bridge between the two cysteines. The two cysteines are arranged so as not to deform the beta-sheet and turn. The protein is more flexible as a result of the length of the disulfide linkage and the smaller number of hydrogen bonds in the beta-sheet portion. The relative flexibility of a cyclic protein can be determined by molecular dynamics simulations.

The invention also relates to a fusion protein. For example, in one embodiment, the fusion protein comprises a first domain comprising a Leptospiral VM protein, variant thereof, or fragment thereof. In one embodiment, the fusion protein comprises a second domain. In one embodiment, the second domain is a targeting domain, wherein the targeting domain directs the fusion protein to a specific cell or tissue of interest. For example, in one embodiment, the targeting domain comprises an antibody, antibody fragment, or peptide that specifically binds to an antigen (e.g., tumor antigen) thereby directing the fusion protein to a cell or tissue expressing the antigen. In one embodiment, the second domain comprises a detectable protein or peptide (e.g., a fluorescent protein) that allows for the visualization of the fusion protein.

In one embodiment, the fusion protein comprises a targeting domain capable of directing the resulting protein to a desired cellular component or cell type or tissue. The chimeric or fusion proteins may also contain additional amino acid sequences or domains. The chimeric or fusion proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate, for example, with vesicles or with the cell surface. In one embodiment, the targeting domain can target a protein to a particular cell type or tissue. For example, the targeting domain can be a cell surface ligand or an antibody against a cell surface antigens of a target tissue. A targeting domain may target a protein of the invention to a cellular component.

In one embodiment, the targeting domain may comprises an antibody or antibody fragment thereof. An antibody may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one embodiment, the targeting domain of a composition of the invention comprises an antibody fragment. In one embodiment, the targeting domain comprises an antibody fragment that comprises a scFv.

The VM-domain containing fusion molecule of the invention can be generated to be reactive to any desirable antigen of interest, or fragment thereof, including, but not limited to a tumor antigen, a bacterial antigen, a viral antigen or a self-antigen. In the context of the present invention, "tumor antigen" or "hyperporoliferative disorder antigen" or "antigen associated with a hyperproliferative disorder," refers to antigens that are common to specific hyperproliferative disorders, such as cancer. In certain aspects, the hyperproliferative disorder antigens of the present invention are derived from cancers including, but not limited to, primary or metastatic melanoma, mesothelioma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The antigens discussed herein are merely included by way of example. The list is not intended to be exclusive and further examples will be readily apparent to those of skill in the art.

Tumor antigens are proteins that are produced by tumor cells that elicit an immune response. The selection of the antigen binding domain of the VM-domain containing fusion molecule of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RUL RU2 (AS), intestinal carboxyl esterase, mut hsp70-2, M-CSF, prostase, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. Another exemplary tumor antigen is chondroitin sulfate proteoglycan 4 (CSPG4) (also referred to as melanoma-associated chondroitin sulfate proteoglycan (MCSP), high-molecular-weight melanoma-associated antigen (HMW-MAA), or neuron-glial antigen 2 (NG2)).

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: differentiation antigens such as MART-1/ MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; over-expressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Depending on the desired antigen to be targeted, the VM-domain containing fusion molecule can be engineered to include an appropriate antigen binding moiety that is specific to the desired antigen target. For example, if CD19 is the desired antigen that is to be targeted, an antibody for CD19 can be used as the antigen binding moiety for incorporation into a VM-domain containing fusion molecule of the invention.

A protein of the invention may be synthesized by conventional techniques. For example, the proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a polypeptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or protein of the invention, conjugated with at least one other molecule, may be prepared by fusing, through recombinant techniques, the N-terminal or C-terminal end of the peptide or protein, and the sequence of a selected protein or selectable marker with a desired biological function. The resultant fusion proteins contain the Leptospiral VM protein, variant thereof, or fragment thereof, fused to the selected protein or marker protein as described herein. Examples of proteins which may be used to prepare fusion proteins include immunoglobulins and regions thereof, glutathione-S-transferase (GST), hemagglutinin (HA), and truncated myc.

A protein of the invention may be developed using a biological expression system. The use of these systems allows the production of large libraries of random sequences and the screening of these libraries for sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The protein of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

The present invention further encompasses fusion proteins in which the protein of the invention or fragments thereof, are recombinantly fused or chemically conjugated (including both covalent and non-covalent conjugations) to heterologous proteins (i.e., an unrelated protein or portion thereof, e.g., at least 10, at least 20, at least 30, at least 40, at least 50, at least 60, at least 70, at least 80, at least 90, at least 100, at least 125, at least 150, at least 175, at least 200, at least 225, at least 250, at least 275, at least 300, or at least 500 amino acids of the polypeptide) to generate fusion proteins. The fusion does not necessarily need to be direct, but may occur through linker sequences.

In one example, a fusion protein in which a protein of the invention or a fragment thereof can be fused to sequences derived from various types of immunoglobulins. For example, a polypeptide of the invention can be fused to a constant region (e.g., hinge, CH2, and CH3 domains) of human IgG or IgM molecule, for example, as described herein, so as to make the fused protein or fragments thereof more soluble and stable in vivo. In another embodiment, such fusion proteins can be administered to a subject so as to inhibit interactions between a ligand and its receptors in vivo. Such inhibition of the interaction will block or suppress signal transduction which triggers certain cellular responses.

In one aspect, the fusion protein comprises a polypeptide of the invention which is fused to a heterologous signal sequence at its N-terminus. For example, the signal sequence naturally found in the protein of the invention can be replaced by a signal sequence which is derived from a heterologous origin. Various signal sequences are commercially available. For example, the secretory sequences of melittin and human placental alkaline phosphatase (Stratagene; La Jolla, Calif.) are available as eukaryotic heterologous signal sequences. As examples of prokaryotic heterologous signal sequences, the phoA secretory signal (Sambrook, et al., supra; and Current Protocols in Molecular Biology, 1992, Ausubel, et al., eds., John Wiley & Sons) and the protein A secretory signal (Pharmacia Biotech; Piscataway, N.J.) can be listed. Another example is the gp67 secretory sequence of the baculovirus envelope protein (Current Protocols in Molecular Biology, 1992, Ausubel, et al., eds., John Wiley & Sons).

In another embodiment, a protein of the invention can be fused to tag sequences, e.g., a hexa-histidine peptide, such as the tag provided in a pQE vector (QIAGEN, Inc., 9259 Eton Avenue, Chatsworth, Calif., 91311), among others, many of which are commercially available. As described in Gentz, et al., 1989, Proc. Natl. Acad. Sci. USA 86:821-824, for instance, hexa-histidine provides for convenient purification of the fusion protein. Other examples of peptide tags are the hemagglutinin "HA" tag, which corresponds to an epitope derived from the influenza hemagglutinin protein (Wilson, et al., 1984, Cell 37:767) and the "flag" tag (Knappik, et al., 1994, Biotechniques 17(4):754-761). These tags are especially useful for purification of recombinantly produced proteins of the invention.

In one embodiment, the protein of the invention can be fused to a detectable label, such as a fluorescent tag. Non-limiting examples of fluorescent tags include green fluorescent protein (GFP), cyan fluorescent protein (CFP), yellow fluorescent protein (YFP), red fluorescent protein (RFP), orange fluorescent protein (OFP), eGFP, mCherry, hrGFP, hrGFPII, Alexa 488, Alexa 594, and the like. Fluorescent tags may also be photoconvertible, such as for example kindling red fluorescent protein (KFP-red), PS-CFP2, Dendra2, CoralHue Kaede and CoralHue Kikume. However, the invention should not be limited to a particular label. Rather, any detectable label can be used to tag the expressed protein.

The present invention also provides isolated nucleic acid molecules that encode the proteins described herein. Therefore, in one embodiment, the composition of the invention comprises an isolated nucleic acid molecule encoding a Leptospiral VM protein, variant thereof, or fragment thereof.

In one embodiment, the isolated nucleic acid molecule encodes a protein having an amino acid sequence of SEQ ID NO: 1, SEQ ID NO: 2, SEQ ID NO: 3, or SEQ ID NO: 4.

In one embodiment, the isolated nucleic acid molecule comprises a nucleic acid sequence of SEQ ID NO:8 (nucleic acid sequence of native *Leptospira interrogans* serovar Lai wildtype encoding LA_0620; full length minus encoded predicted signal peptide).

In one embodiment, the isolated nucleic acid molecule comprises a nucleic acid sequence of SEQ ID NO:9 (nucleic acid sequence of native *Leptospira interrogans* serovar Lai wildtype encoding LA_3490; full length minus encoded predicted signal peptide).

In one embodiment, the isolated nucleic acid molecule comprises a nucleic acid sequence of SEQ ID NO:10, encoding the predicted Ricin B domain LA_0620 (short).

In one embodiment, the isolated nucleic acid molecule comprises a nucleic acid sequence of SEQ ID NO:11, encoding the predicted Ricin B domain LA_3490 (short).

The isolated nucleic acid may comprise any type of nucleic acid, including, but not limited to DNA, cDNA, and RNA. For example, in one embodiment, the composition comprises an isolated DNA molecule, including for example, an isolated cDNA molecule, encoding a protein or functional fragment thereof. In one embodiment, the composition comprises an isolated RNA molecule encoding a protein or a functional fragment thereof.

The nucleic acid sequences include both the DNA sequence that is transcribed into RNA and the RNA sequence that is translated into a protein. According to other embodiments, the nucleic acid sequences of the invention are inferred from the amino acid sequence of the proteins of the invention. As is known in the art several alternative nucleic acid sequences are possible due to redundant codons, while retaining the biological activity of the translated proteins.

Further, the invention encompasses an isolated nucleic acid molecule encoding a protein having substantial homology to the proteins disclosed herein. In some embodiments, the present invention encompasses an isolated nucleic acid molecule encoding a protein comprising an amino acid sequence having at least about 75%, 80%, 85%, 86%, 87%, 88%, 89%, 90%, 91%, 92%, 93%, 94%, 95%, 96%, 97%, 98%, or 99% sequence homology with an amino acid sequence an amino acid sequence of the proteins disclosed herein. In some embodiments, the nucleic acid sequence encoding a protein of the invention is "substantially homologous," that is about 50% homologous, about 70% homologous, about 80% homologous, about 90% homologous, about 91% homologous, about 92% homologous, about 93% homologous, about 94% homologous, about 95% homologous, about 96% homologous, about 97% homologous, about 98% homologous, or about 99% homologous to a nucleic acid sequence described herein.

It is to be understood explicitly that the scope of the present invention encompasses homologs, analogs, variants, fragments, derivatives and salts, including shorter and longer proteins and nucleic acid molecules, as well as protein and nucleic acid molecule analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the activity of the original molecule. Specifically, any active fragments of the active proteins and nucleic acid molecules, as well as extensions, conjugates and mixtures are included and are disclosed herein according to the principles of the present invention.

The invention should be construed to include any and all isolated nucleic acid sequences which are homologous to the nucleic acid sequences described and referenced herein, provided these homologous nucleic acid sequences encode proteins having the biological activity of the proteins disclosed herein.

The skilled artisan would understand that the nucleic acid sequences of the invention encompass an RNA or a DNA sequence encoding a protein of the invention, and any modified forms thereof, including chemical modifications of the DNA or RNA which render the sequence more stable when it is cell free or when it is associated with a cell. Chemical modifications of nucleotides may also be used to enhance the efficiency with which a nucleic acid sequence is taken up by a cell or the efficiency with which it is expressed in a cell. Any and all combinations of modifications of the nucleic acid sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. The above modifications may be combined.

In some instances, the nucleic acid molecule comprises at least one of the following chemical modifications: 2'-H, 2'-O-methyl, or 2'-OH modification of one or more nucleotides. In some embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, for example different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a protein is typically achieved by operably linking a nucleic acid encoding the protein or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In some embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a protein, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a peptide or protein into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York).

Biological methods for introducing a peptide or protein of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a peptide or protein into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular polypeptide, e.g., by immunological means (ELISAs and Western blots) or by assays described herein to identify agents falling within the scope of the invention.

In one embodiment, the present invention provides a delivery vehicle comprising a protein, or a nucleic acid molecule encoding protein. Exemplary delivery vehicles include, but are not limited to, microspheres, microparticles, nanoparticles, polymerosomes, liposomes, and micelles. For example, in some embodiments, the delivery vehicle is loaded with protein, or a nucleic acid molecule encoding a protein. In some embodiments, the delivery vehicle provides for controlled release, delayed release, or continual release of its loaded cargo. In some embodiments, the delivery vehicle comprises a targeting moiety that targets the delivery vehicle to a treatment site.

In one embodiment, the present invention provides an implantable scaffold or device comprising the protein or nucleic acid molecule encoding the protein. For example, in some embodiments, the present invention provides a tissue engineering scaffold, including but not limited to, a hydrogel, electrospun scaffold, polymeric matrix, or the like, comprising the protein or nucleic acid molecule encoding the protein in or on the scaffold.

In certain aspects, the present invention encompasses compositions, including polypeptides, nucleotides, vectors, bacteria, and vaccines, that when administered to a subject, elicit or enhance an immune response. In certain instances, the composition elicits an immune response directed against a bacteria of genus *Leptospira* including an immune response directed against a Leptospiral VM protein. Further, when the compositions are administered to a subject, they elicit an immune response that serves to protect the inoculated subject against conditions associated with *Leptospira* infection.

In one embodiment, the present invention provides compositions that are useful as immunomodulatory agents, for example, for stimulating immune responses and in preventing *Leptospira* related pathology. In various embodiments, the immunomodulatory agents comprise (a) a Leptospiral VM protein, variant thereof, or fragment thereof; or (b) a nucleic acid molecule encoding a Leptospiral VM protein, variant thereof, or fragment thereof. In one embodiment, the immune response is not detrimental to the host and therefore the compositions of the invention are useful as a vaccine. In one embodiment, the immunomodulatory agents are administered in combination with an adjuvant. In another embodiment, the immunomodulatory agents are administered in the absence of an adjuvant.

In some embodiments, the compositions are used as immunostimulatory agents to induce or enhance the production of specific antibodies. In certain aspects, the immunostimulatory agents protect against Leptospiral induced pathology.

In one embodiment, the composition comprises a bacterium comprising (a) a Leptospiral VM protein, variant thereof, or fragment thereof; or (b) a nucleic acid molecule encoding a Leptospiral VM protein, variant thereof, or fragment thereof. For example, in one embodiment, the composition comprises a bacterium of genus *Leptospira* comprising (a) a Leptospiral VM protein, variant thereof, or fragment thereof; or (b) a nucleic acid molecule encoding a Leptospiral VM protein, variant thereof, or fragment thereof. In one embodiment, the composition comprises a bacterium that is not a bacterium of genus *Leptospira*, wherein the bacterium comprises (a) a Leptospiral VM protein, variant thereof, or fragment thereof; or (b) a nucleic acid molecule encoding a Leptospiral VM protein, variant thereof, or fragment thereof.

A bacterium comprising a nucleotide sequence encoding a Leptospiral VM protein, variant thereof, or fragment thereof, can be generated using any method known in the art including, but not limited to allelic exchange and site-directed mutagenesis.

Any bacterium or bacterial strain which has at least one nucleotide sequence encoding a Leptospiral VM protein, variant thereof, or fragment thereof can be selected and used in accordance with the invention. In one embodiment, naturally occurring mutants or variants, or spontaneous mutants can be selected. In another embodiment, mutant bacteria can be generated by exposing the bacteria to mutagens, such as ultraviolet irradiation or chemical mutagens, or by multiple passages and/or passage in non-permissive hosts. Screening in a differential growth system can be used to select for those mutants having a mutation in a Leptospiral VM protein.

In another embodiment, mutations can be engineered into a bacterium, for example a *Leptospira* bacterium using "reverse genetics" approaches. In this way, natural or other mutations which confer an inactivated or attenuated phenotype can be engineered into strains. For example, deletions, insertions or substitutions of the coding region of the gene responsible for the Leptospiral VM protein can be engineered. Deletions, substitutions or insertions in the noncoding region of the gene responsible for the Leptospiral VM protein are also contemplated. To this end, mutations in the signals responsible for the transcription, replication, polyadenylation and/or packaging of the gene responsible for the Leptospiral VM protein can be engineered.

In one embodiment, the bacterium is engineered to be deficient, in which a Leptospiral VM protein is absent. For example, in certain embodiments, a toxin-deficient mutant bacterium or virus, where one or more Leptospiral VM protein is absent, is unable to cause disease but is able to induce an adaptive immune response against genus *Leptospira*.

Bacterium generated by the approaches described herein can be used in the vaccine and pharmaceutical formulations described herein. Reverse genetics techniques can also be used to engineer additional mutations to other genes important for vaccine production—i.e., the epitopes of useful vaccine strain variants can be engineered into the bacterium. Alternatively, completely foreign epitopes, including antigens derived from other pathogens can be engineered into the inactivated or attenuated strain.

The inactivated or attenuated bacterium of the present invention can itself be used as the active ingredient in vaccine or pharmaceutical formulations. In certain embodiments, the bacterium can be used as the vector or "backbone" of recombinantly produced vaccines. To this end, the "reverse genetics" technique can be used to engineer mutations or introduce foreign epitopes into the bacterium, which would serve as the "parental" strain. In this way, vaccines can be designed for immunization against strain variants, or in the alternative, against completely different infectious agents or disease antigens.

For example, in one embodiment, the immunological composition of the invention comprises a bacterium, engineered to express one or more epitopes or antigens of a given pathogen. For example, the bacterium can be engineered to express neutralizing epitopes of other preselected strains. Alternatively, epitopes of other pathogens can be built into the mutant bacterium.

In one embodiment, the bacterium is capable of inducing a robust immune response in the host—a feature which contributes to the generation of a strong immune response when used as a vaccine, and which has other biological consequences that make the bacterium useful as pharmaceutical agents for the prevention and/or treatment of an infection, disease, or disorder associated with an antigen. For example, in certain embodiments, the bacterium induces an anti-Leptospiral immune response.

For an antigenic composition to be useful as a vaccine, the antigenic composition must induce an immune response to the antigen in a cell, tissue or subject (e.g., a human). In certain aspects the vaccine induces a protective immune response in the subject. As used herein, an "immunological composition" may comprise, by way of examples, an antigen (e.g., a protein), a nucleic acid molecule encoding an antigen (e.g., an antigen expression vector), or a cell expressing or presenting an antigen. In particular embodiments the antigenic composition comprises or encodes all or part of any protein antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" (also referred to as an immunogenic composition) refers to a substance that induces immunity upon inoculation into an animal. In one embodiment, the vaccine induces anti-Leptospiral immunity. In various embodiments, the vaccine of the invention comprises In one embodiment, the vaccine is administered in combination with an adjuvant. In another embodiment, the vaccine is administered in the absence of an adjuvant.

A vaccine of the present invention may vary in its composition of nucleic acid and/or cellular components. In a non-limiting example, a nucleic encoding an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In one embodiment, the protein vaccine of the invention includes, but is not limited to at least one Leptospiral VM protein, variant thereof, or fragment thereof, optionally mixed with adjuvant substances. In some embodiments, the protein is introduced together with an antigen presenting cell (APC). The most common cells used for the latter type of vaccine are bone marrow and peripheral blood derived dendritic cells, as these cells express costimulatory molecules that help activation of T cells. WO00/06723 discloses a cellular vaccine composition which includes an APC presenting tumor associated antigen polypeptides. Presenting the protein can be effected by loading the APC with a polynucleotide (e.g., DNA, RNA) encoding the proteine or loading the APC with the protein itself.

For example, a method for detecting the induction of cytotoxic T lymphocytes is well known. A foreign substance that enters the living body is presented to T cells and B cells by the action of APCs. T cells that respond to the antigen presented by APC in an antigen-specific manner differentiate into cytotoxic T cells (also referred to as cytotoxic T lymphocytes or CTLs) due to stimulation by the antigen. The antigen stimulated cells then proliferate. This process is referred to herein as "activation" of T cells. Therefore, CTL induction by a certain polypeptide or combination of polypeptides of the invention can be evaluated by presenting the polypeptide to a T cell by APC, and detecting the induction of CTL. Furthermore, APCs have the effect of activating CD4+ T cells, CD8+ T cells, macrophages, eosinophils and NK cells.

A method for evaluating the inducing action of CTL using dendritic cells (DCs) as APC is well known in the art. DC is a representative APC having the strongest CTL inducing action among APCs. In this method, the polypeptide or combination of polypeptides are initially contacted with DC and then this DC is contacted with T cells. Detection of T cells having cytotoxic effects against the cells of interest after the contact with DC shows that the polypeptide or combination of polypeptides have an activity of inducing the cytotoxic T cells. Furthermore, the induced immune response can be also examined by measuring IFN-gamma produced and released by CTL in the presence of antigen-presenting cells that carry immobilized polypeptide or combination of polypeptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The polypeptide, or combination of polypeptides, confirmed to possess CTL inducing activity by these methods are polypeptides having DC activation effect and subsequent CTL inducing activity. Therefore, a polypeptide or combination of polypeptides that induce CTL against a Leptospiral VM protein are useful as vaccines against Leptospira associated pathology. Furthermore, CTL that have acquired cytotoxicity due to presentation of the polypeptide or combination of polypeptides by APC can be also used as vaccines against Leptospiral infection.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous to use a mixture of multiple types of fragments.

The induction of immunity by a polypeptide or combination of polypeptides can be further confirmed by observing the induction of antibody production against the specific antigen. For example, when antibodies against a polypeptide or combination of polypeptides are induced in a laboratory animal immunized with the polypeptide or combination of polypeptides, and when Leptospiral associated pathology is suppressed by those antibodies, the polypeptide or combination of polypeptides are determined to induce anti-Leptospiral immunity.

Methods

In various embodiments, the compositions of the invention can be used in biological assays, including methods of detecting a protein (e.g. asialofetuin). Exemplary biological assays include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (MA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007). In some embodiments, the level of asialofetuin in the biological sample is measured with an assay that uses at least one Leptospiral VM protein, variant thereof, or fragment thereof; or a nucleic acid molecule encoding a Leptospiral VM protein, variant thereof, or fragment thereof of the invention, as described elsewhere herein.

In various embodiments, the present invention provides methods comprising administering a composition described herein, to a subject in need thereof. For example, in one embodiment, the method comprises administering to a subject a composition comprising a) a Leptospiral VM protein, variant thereof, or fragment thereof or (b) a nucleic acid molecule encoding a Leptospiral VM protein, variant thereof, or fragment thereof. In various embodiments, the compositions of the invention can be used as agents for inducing Leptospiral immunity or as cytotoxic agents for the treatment of a disease or disorder.

Methods of Use as Cytotoxic Therapeutic Agent

In one aspect, the present invention provides methods to treat a disease or disorder in a subject in need thereof. In one embodiment, the present invention provides a method of inducing cell damage or cell death by administering to a cell a composition comprising a) a Leptospiral VM protein, a variant thereof, a fragment thereof, or a fusion thereof or (b) a nucleic acid molecule encoding a Leptospiral VM protein, a variant thereof, a fragment thereof, or a fusion thereof. In some embodiments, the method comprises administering to a subject a composition comprising a fusion protein, or a nucleic acid molecule encoding a fusion protein, wherein the fusion protein comprises a first domain comprising a Leptospiral VM protein, variant thereof, or fragment thereof, and a second domain comprising a targeting domain that directs the fusion protein to a desired cell type, thereby inducing the cell damage or cell death of the targeted cell.

The method of the present invention is used to treat any type of disease or disorder associated with the antigen that is recognized by the antigen receptor encoded by the antigen receptor composition, including, but not limited to cancer and pathogenic diseases and disorders. The immunogenic composition can be used to reduce tumor growth or metastasis or protect against tumor development, thereby treating, preventing, and/or protecting against cancer based pathologies.

In one embodiment, the present invention provides a method comprising administering to a subject having cancer a composition comprising a) a Leptospiral VM protein, a variant thereof, a fragment thereof, or a fusion thereof or (b) a nucleic acid molecule encoding a Leptospiral VM protein, a variant thereof, a fragment thereof, or a fusion thereof. In one embodiment, the present invention provides a method comprising administering to a subject having cancer a composition comprising a fusion protein, or a nucleic acid molecule encoding a fusion protein, wherein the fusion protein comprises a first domain comprising a Leptospiral VM protein, variant thereof, or fragment thereof, and a second domain comprising a targeting domain that directs the fusion protein to a cancerous cell or tumor cell.

The following are non-limiting examples of cancers that can be treated by the disclosed methods: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocytoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and wilms tumor.

The therapeutic compounds or compositions of the invention may be administered prophylactically or therapeutically to subjects suffering from, or at risk of, developing cancer. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

Compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials. When "an effective amount", or "therapeutic amount" is indicated, the precise amount of the compositions of the present invention to be administered can be determined by a physician with consideration of individual differences in age, weight, disease progression, and condition of the patient (subject). The optimal dosage and treatment regime for a particular patient can readily be determined by one skilled in the art of medicine by monitoring the subject for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous (i.v.) injection, or intraperitoneally.

Forms of administration that may be useful in the methods described herein include, but are not limited to, direct delivery to a desired organ, oral, inhalation, intranasal, intratracheal, intravenous, intramuscular, intratumroal, subcutaneous, intradermal, and other parental routes of administration. Additionally, routes of administration may be combined, if desired. In one embodiments, route of administration is intradermal injection or intratumoral injection. In one embodiment, one or more composition is administered to a treatment site during a surgical procedure, for example during surgical resection of all or part of a tumor.

Methods of Use as a Vaccine

Thus, the present invention also encompasses a method of inducing anti-Leptospiral immunity using one or more of the compositions described herein. Anti-Leptospiral immunity can be induced by administering a composition of the invention, and the induction of anti-Leptospiral immunity enables treatment and prevention of pathologies associated with Leptospiral infection. Thus, the invention provides a method for treating, or preventing infection by genus *Leptospira*.

In one embodiment, the method comprises administering to a subject having a Leptospiral infection a composition comprising a) a Leptospiral VM protein, a variant thereof, a fragment thereof, or a fusion thereof; or (b) a nucleic acid molecule encoding a Leptospiral VM protein, a variant thereof, a fragment thereof, or a fusion thereof.

When a certain composition induces a Leptospiral immune response upon inoculation into an animal, the composition is determined to have an immunity inducing effect. The induction of immunity by a composition can be detected by observing in vivo or in vitro the response of the immune system in the host against the composition.

In another embodiment, the methods of the invention comprise administering to the subject a bacterium or virus comprising a nucleic acid sequence encoding a nucleic acid molecule encoding a Leptospiral VM protein, variant thereof, or fragment thereof. In another embodiment, the methods of the invention comprise administering to the subject a bacterium or virus, wherein a Leptospiral VM protein is absent. For example, in certain embodiments, administering a toxin-deficient mutant bacterium or virus, where a Leptospiral VM protein is absent, is unable to cause disease but is able to induce an adaptive immune response.

The therapeutic compounds or compositions of the invention may be administered prophylactically or therapeutically to subjects suffering from, or at risk of, or susceptible to, developing an infection, disease, or disorder associated with the antigen. Such subjects may be identified using standard clinical methods. As described elsewhere herein, in the context of the present invention, prophylactic administration occurs prior to the manifestation of overt clinical symptoms of disease, such that a disease or disorder is prevented or alternatively delayed in its progression. Prevention can occur at primary, secondary and tertiary prevention levels.

The polypeptide or combination of polypeptides of the invention having immunological activity, or a polynucleotide or vector encoding such a polypeptide or combination of polypeptides, may optionally be combined with an adjuvant. An adjuvant refers to a compound that enhances the immune response against the polypeptide or combination of polypeptides when administered together (or successively) with the polypeptide having immunological activity. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

In one embodiment, the methods of the present invention comprise administering a composition comprising a) a Leptospiral VM protein, variant thereof, or fragment thereof; or (b) a nucleic acid molecule encoding a Leptospiral VM protein, variant thereof, or fragment thereof, to a subject. Administration of the composition can comprise, for example, intramuscular, intravenous, peritoneal, subcutaneous, intradermal, as well as topical administration.

The actual dose and schedule can vary depending on whether the compositions are administered in combination with other pharmaceutical compositions, or depending on inter-individual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

These methods described herein are by no means all-inclusive, and further methods to suit the specific application will be apparent to the ordinary skilled artisan. Moreover, the effective amount of the compositions can be further approximated through analogy to compounds known to exert the desired effect.

Dosage and Formulation

The present invention envisions treating a disease, for example, cancer or diseases associated with a pathogen, in a subject by the administration of one or more of the therapeutic agents of the present invention (e.g., the VM-domain fusion constructs of the invention).

Administration of the composition in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. In one embodiment, the cytokine composition, the antigen receptor composition, and the integration composition of the invention are administered locally to the same site. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into a tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

In certain embodiments, the therapeutic agent is combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. In one embodiment, the composition described above is administered to the subject by intratumoral injection. Other forms of administration that may be useful in the methods described herein include, but are not limited to, direct delivery to a desired organ, intramuscular, subcutaneous, intradermal, and other parental routes of administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Kits

The invention also includes a kit comprising one or more of the compositions described herein. For example, in one embodiment, the kit comprises a Leptospiral VM protein, a variant or fragment thereof, a nucleic acid molecule encoding a Leptospiral VM protein, a variant or fragment thereof or a fusion construction comprising a Leptospiral VM domain. In one embodiment, the kit comprises instructional material which describes the use of the composition. For instance, in some embodiments, the instructional material describes administering the composition(s), to a subject as a therapeutic treatment or a non-treatment use as described elsewhere herein. In an embodiment, the kit further comprises one or more additional reagents for use in an assay, for example in an immunoassay of the invention.

EXPERIMENTAL EXAMPLE

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: PF07598 Gene Family Members Encode VM ("Virulence Modifying") Proteins VM proteins are demonstrated to be potent toxins that bind to HeLa cells and have destructive, cytopathic effect. The VM proteins have potential commercial biotechnological, therapeutic and vaccine uses. The N-terminal, conserved ricin B-like lectin domains of VM proteins have strong potential to be a leptospirosis vaccine. VM proteins have potential use as biological probes in cell biology, biochemistry, and immunology. They also have potential for use in cancer therapy as fusion proteins.

The experiments provided herein identified a Ricin B chain-like functional domain in the amino terminus of the PF07598 gene family. It is demonstrated that recombinant PF07598-derived recombinant Ricin B-like protein domain and full length protein bind to the predicted terminal galactosyl glycoprotein, asialofetuin. Further it is demonstrated that two PF07598 recombinant Ricin B-like protein domains and full length proteins bind to the surface of HeLa cells in vitro. It is also demonstrated that the full length PF07598 gene family-expressed proteins cause cytopathic effect and cell death (demonstrating that this gene family encodes a unique bacterial-secreted toxin protein related to pathogenesis of the disease, leptospirosis. The cellular toxicity/cytopathic effect is associated with actin depolymerization of target cells as a mechanism of cytopathic effect. The Ricin B domain may be useful as a cell imaging probe. Alignment of the Ricin B domains of all PF07598 gene family members in the genus demonstrated high degree of conservation, indicating that the PF07598 gene family is a pan-leptospirosis vaccine candidate. PF07598 proteins may be the target of neutralizing therapeutic antibodies (or drug inhibitors) that might be used to treat severe, life-threatening leptospirosis. Further, the toxin domain of the PF07598 gene family may be useful as a cancer therapeutic when coupled to cancer cell-specific antibodies. The PF07598 gene family proteins may be useful biological probes for cell biology, biochemistry, and immunology biotechnology applications, and also applicable to leptospirosis eradication because animal reservoirs could be vaccinated with an oral vaccine that encoded PF07598 gene family member(s).

A leptospirosis vaccine based on the PF07598 gene family would be easier to manufacture (because these vaccine candidates have been produced in *E. coli* as recombinant protein purified by column chromatography) than the current vaccine (which requires growing live virulent organisms in bioreactors). Further, it would be more effective than current vaccines because it would be broadly reactive against the most important *Leptospira* pathogens, and applicable to animal and human health because leptospirosis is a zoonotic disease. Further the vaccine of the invention is applicable to leptospirosis eradication via zoonotic reservoir vaccination, which is broadly protective against *leptospira* from diverse sources. Leptospirosis vaccines have to be inexpensive to be marketable to agriculture and endemic countries in the developing world, and the provides a method and composition of matter that enables inexpensive manufacture.

The materials and methods employed in these experiments are now described.

Construct Design

A synthetic gene construct was designed (FIG. 1), produced in *E. coli*-preferred codons, which was produced from overlapping synthetic oligos and cloned intoT7 promoter expression plasmid, pET32b with an N-terminal trx fusion protein and S-tag (C-terminal His6 tag). The construct was constructed with an mCherry fusion protein at C-terminus, and preceded by enterokinase cleavage site. The construct was transfected into T7 shuffle cells (New England BioLabs) for expression.

Expression, Purification and Characterization

Cells were grown at 37° C. to OD600=0.4, then incubated in shaking incubator overnight at 16° C. The bacteria was observed to be pink. Cells were lysed either by sonication or by Cell Lytic B/Benzonase/Lysozyme/EDTA-free protease inhibitors (Roche). The lysate was analyzed for soluble vs. inclusion body by SDS-PAGE and Western blot. Proteins were purified using HiTrap NiNTA sepharose on AKTA Explorer. SDS-PAGE and WB confirmed>95% purity. A limulus lysate on purified protein demonstrated<0.5 mUnits of endotoxin/mL. The target protein was quantified using a Bradford assay.

The results of these experiments are now described.

The optimization, expression and purification of soluble full length rLA_3490 is shown in FIG. 2A through FIG. 2E. The expression, on column refolding and purification of rLA_0620_Short is shown in FIG. 3A through FIG. 3C. Recombinant VM proteins, like Ricin B, binds to Asialofetuin (terminal galactose-containing glycoprotein) (FIG. 4). Western blot detection of a LA_0620 VM paralog in Pathogenic *Leptospira* serovar Manilae is shown in FIG. 5A through FIG. 5C. Western blot detection of LA_3490 VM paralog in Pathogenic *Leptospira* serovar Manilae is shown in FIG. 6A through FIG. 6C.

rLA_3490_Full is Cytotoxic to HeLa Cells

The cytopathic effect of in vivo-mimicked (Rat serum, NaCl) *Leptospira* on HeLa cells is shown in FIG. 7. Treatment of HeLa cells with soluble rLA_3490_Full reproduces effect of induced *Leptospira* (FIG. 8). rLA_0620_Short also showed slight killing of the cells. The treatment of HeLa cells with soluble rLA_0620_Short is shown in FIG. 9. The treatment of HeLa cells with BSA as negative control (for endotoxin) is shown in FIG. 10.

Morphological Changes

The binding of recombinant LA_0620 short-mCherry fusion (Ricin B domain alone) to HeLa cells is shown in FIG. 11. rLA_3490_Full protein significantly altered the morphology and detached the cells at 5 μg/mL which was evident at 4 h of treatment. Intriguingly blebbing and necrosis were seen at 24 h of treatment (FIG. 12). rLA_0620_Short and rLA_0620_Full proteins rounded and detached the cells from substratum though blebbing and necrosis were not seen at 4 hours (FIG. 20 and FIG. 21). Altered morphology was not significant when cells were treated with BSA prepared in elution buffer and also when treated with only elution buffer (FIG. 22 and FIG. 23). Though a few cells were rounded. Untreated cells did not show any alterations in the morphology (FIG. 19). Live and Dead staining confirmed that rLA_3490_Full protein kill the cells at 4 hours of treatment with 5 μg/mL (FIG. 14 through FIG. 18).

Together these results demonstrate that recombinant full length LA_3490 recapitulates the cytopathic effect of *leptospira* to a greater degree than recombinant full length LA_0620. Further, the recombinant Ricin B domain alone binds to the cell surface but does not recapitulate the cytopathic effect of *leptospira*.

Example 2: Effect of VM ("Virulence Modifying") Proteins on Different Cell Lines Experiments were performed to demonstrate the cytopathic effect of leptospiral proteins (soluble rLA_3490 and rLA_0620) on glioblastoma, astrocytes and endothelial cell lines. The experiments were performed in 8 well chamber slides. 35,000 cells/200 μL were seeded to wells. Three cell lines were treated with rLA_3490 (Short and Full length) and rLA_0620 (Short and Full length) at 5 μg/mL concentration. BSA in elution buffer (5 μg/mL) and elution buffer (5μ/mL) alone were served as controls. Images were captured at 2 hours and 4 hours.

Treatment of cells with rLA_3490_Full and rLA_0620_Full altered the morphology of all the three cell lines (FIG. 24 through FIG. 26). Treatment of cells with rLA_3490_Short and rLA_0620_Short did not alter the morphology (FIG. 24 through FIG. 26). Untreated and control endothelial cells also showed altered morphology though there was a significance difference with rLA_3490_Full and rLA_0620_Full treated cells (FIG. 26 and FIG. 27). BSA and Elution buffer did not affect the astrocytes and glioblastoma cell line (FIG. 27).

```
Sequences
Leptospiral VM protein comprising the amino
acid sequence (minus the signal peptide of
LA_0620 (full length expressed in pET32b+
E. coli expression vector:
>gi|24213320|ref|NP_710801.1| hypothetical
protein LA_0620 [Leptospira interrogans
serovar Lai str. 56601]
                              SEQ ID NO: 1
SSKIEYSVIQKPTDPPKDKPIKVIVSDGGKFCYGPNFSGG

ESYIIIEQCWQMHVMNARYDVFQRISYNINNTWLCITAPE

KVIKAEETWDYVHLRPCTINDPLQRWIIKNNSFWTANGFY

RLKDYNWYGYISRNSGDRYNHTLDPSMNDWVNTIATPGNI

SIQTSIAWNLQTTEGGQERYFIRWGSSNKNTTPLYYNPENG

HLAQYDPISGSLYCMYSQVDNYQWNWVKWKWCSDSLESKS

KGNPTFWNVFFETDQGGMITDYKGNALRVTRYGSNWGVAY

TAKPDFVKTDTKNSPTSLFVVDKSLLDWTRYTSSNLGKTE

QYCPAGNKESVVHKKAKRTLPPDFQLTEAWIRRLYEIART

DPSSRTSRGVCGVCMLQALQMIAELQEYHSQGPLQSGGYF

FNTAPNTNPFISFGQRYPHLDRLLVDIYRVFDHFFDTSHT

LGYLSAMNLLPQYEWGRTREFSTMSEIRSHIRSLITSPPG

NIWLVLMTMIYPDGTRGGHAVPILRTPQGLVVIETTMATA

TFEEYRAALRPTTDFEQIIRNLRGPNNILIGLSTLQLGRF

YHNPLDSMISNRNCTGEGSDRRGTGGYPASTSVNQCSSKS

SRCSLQ

Leptospiral VM protein comprising the amino
acid sequence (minus the signal peptide of
LA_3490 (full length expressed in pET32b+
E. coli expression vector:
>gi|24216189|ref NP_713670.1| hypothetical
protein LA_3490 [Leptospira interrogans
serovar Lai str. 56601]
                              SEQ ID NO: 2
FEYGVNHTHIHALSKIEYSVIQKPTDPPKDKPIKVIVSDG

GKFCYGPNFSGGESYIIIEQCWQMHVMNARYDVFQRISYN

INNTWLCITAPEKVIKAEKNWDYVHLRPCTINDPLQRWII

KNNSFWTANGFYRLKDYNWYGYISRNSGDRYNHTLDSSMN

DWVNTIATPGNISIQTSIAWNLQTTEGGQERYFIRWGGSDK
```

-continued

NTTPLYYNPENGHLAQYDPISGSLYCMYSQVDNYQWNWVK

WKWCSDLLESKSKGNPTFWNVFFETDQGGMITDYKGNALR

VTRYGSNWGSAYTAKPSYLEKDTTNSPTSLFVVNKDLLDW

TRYTASNLGKTGQYCPAGKRENIVHRRVKRELPPDFQLTE

AWIRRLYEIATSVSAESETRVSGICGPCALHSFQMLAELL

EYHSREPLQSGGYFFDTAPNTDPFISFGQRYPHLERLLED

IPKKYAPYPHYSTQSFLSFASIDSMLPQYFWSASTEFTNR

DEILSHISSLINSPAGSIWLGVMEQQHPDGTITGHAAPIL

RISQGLVVIPTNVHLWTLEEFRRFLIPTTELSQIVANLEG

SNTLIRFTTIQSLGMLTTNMFDSMVSNRNCTGEGEDRRGS

GEYPTSTSVNQCPSGRCALPF predicted Ricin B-like domain:
                              SEQ ID NO: 3
ESYIIIEQCWQMHVMNARYDVFQRISYNINNTWLCITAPE

KVIKAEETWDYVHLRPCTINDPLQRWIIKNNSFWTANGFY

RLKDYNWYGY predicted Ricin B-like domain:
                              SEQ ID NO: 4
ESYIIIEQCWQMHVMNARYDVFQRISYNINNTWLCITAPE

KVIKAEKNWDYVHLRPCTINDPLQRWIIKNNSFWTANGFY

RLKDYNWYGY enterokinase cleavage site
                              SEQ ID NO: 5
DDDDK LA_0620 (full)-mCherry Fusion protein
including Gly4Ser linkers and an
enterokinase cleavage site
                              SEQ ID NO: 6
SSKIEYSVIQKPTDPPKDKPIKVIVSDGGKFCYGPNFSGG

ESYIIIEQCWQMHVMNARYDVFQRISYNINNTWLCITAPE

KVIKAEETWDYVHLRPCTINDPLQRWIIKNNSFWTANGFY

RLKDYNWYGYISRNSGDRYNHTLDPSMNDWVNTIATPGNI

SIQTSIAWNLQTTEGQERYFIRWGSSNKNTTPLYYNPENG

HLAQYDPISGSLYCMYSQVDNYQWNWVKWKWCSDSLESKS

KGNPTFWNVFFETDQGGMITDYKGNALRVTRYGSNWGVAY

TAKPDFVKTDTKNSPTSLFVVDKSLLDWTRYTSSNLGKTE

QYCPAGNKESVVHKKAKRTLPPDFQLTEAWIRRLYEIART

DPSSRTSRGVCGVCMLQALQMIAELQEYHSQGPLQSGGYF

FNTAPNTNPFISFGQRYPHLDRLLVDIYRVFDHFFDTSHT

LGYLSAMNLLPQYEWGRTREFSTMSEIRSHIRSLITSPPG

NIWLVLMTMIYPDGTRGGHAVPILRTPQGLVVIETTMATA

TFEEYRAALRPTTDFEQIIRNLRGPNNILIGLSTLQLGRF

YHNPLDSMISNRNCTGEGSDRRGTGGYPASTSVNQCSSKS

SRCSLQGGGGSGGGGSGGGGSDDDDKMVSKGEEDNMAIIK

EFMRFKVHMEGSVNGHEFEIEGEGEGRPYEGTQTAKLKVT

KGGPLPFAWDILSPQFMYGSKAYVKHPADIPDYLKLSFPE

-continued

GFKWERVMNFEDGGVVTVTQDSSLQDGEFIYKVKLRGTNF

PSDGPVMQKKTMGWEASSERMYPEDGALKGEIKQRLKLKD

GGHYDAEVKTTYKAKKPVQLPGAYNVNIKLDITSHNEDYT

IVEQYERAEGRHSTGGMDELYK

LA_3490 (full)-mCherry Fusion protein
including Gly4Ser linkers and an
enterokinase cleavage site
                              SEQ ID NO: 7
FEYGVNHTHIHALSKIEYSVIQKPTDPPKDKPIKVIVSDG

GKFCYGPNFSGGESYIIIEQCWQMHVMNARYDVFQRISYN

INNTWLCITAPEKVIKAEKNWDYVHLRPCTINDPLQRWII

KNNSFWTANGFYRLKDYNWYGYISRNSGDRYNHTLDSSMN

DWVNTIATPGNISIQTSIAWNLQTTEGQERYFIRWGGSDK

NTTPLYYNPENGHLAQYDPISGSLYCMYSQVDNYQWNWVK

WKWCSDLLESKSKGNPTFWNVFFETDQGGMITDYKGNALR

VTRYGSNWGSAYTAKPSYLEKDTTNSPTSLFVVNKDLLDW

TRYTASNLGKTGQYCPAGKRENIVHRRVKRELPPDFQLTE

AWIRRLYEIATSVSAESETRVSGICGPCALHSFQMLAELL

EYHSREPLQSGGYFFDTAPNTDPFISFGQRYPHLERLLED

IPKKYAPYPHYSTQSFLSFASIDSMLPQYFWSASTEFTNR

DEILSHISSLINSPAGSIWLGVMEQQHPDGTITGHAAPIL

RISQGLVVIPTNVHLWTLEEFRRFLIPTTELSQIVANLEG

SNTLIRFTTIQSLGMLTTNMFDSMVSNRNCTGEGEDRRGS

GEYPTSTSVNQCPSGRCALPFGGGGSGGGGSGGGGSDDDD

KMVSKGEEDNMAIIKEFMRFKVHMEGSVNGHEFEIEGEGE

GRPYEGTQTAKLKVTKGGPLPFAWDILSPQFMYGSKAYVK

HPADIPDYLKLSFPEGFKWERVMNFEDGGVVTVTQDSSLQ

DGEFIYKVKLRGTNFPSDGPVMQKKTMGWEASSERMYPED

GALKGEIKQRLKLKDGGHYDAEVKTTYKAKKPVQLPGAYN

VNIKLDITSHNEDYTIVEQYERAEGRHSTGGMDELYK nucleic acid sequence of native *Leptospira
interrogans serovar Lai* wildtype encoding
LA_0620
(full length minus encoded predicted
signal peptide).
                              SEQ ID NO: 8
TCATCAAAAATTGAATACTCGGTTATTCAAAAACCTACCG

ATCCACCAAAAGACAAACCAATCAAAGTAATTGTAAGCGA

TGGAGGAAAGTTTTGTTACGGTCCTAATTTTAGCGGAGGT

GAAAGTTACATTATAATTGAACAGTGTTGGCAAATGCACG

TTATGAATGCAAGATACGACGTGTTTCAAAGAATTTCGTA

TAACATCAATAATACGTGGTTATGTATTACTGCTCCGGAG

-continued

AAAGTAATTAAAGCAGAAGAAACCTGGGACTATGTTCATC

TCAGACCTTGTACGATCAATGATCCTCTGCAGAGATGGAT

TATAAAAAACAATTCTTTTTGGACTGCAAATGGGTTTTAC

CGATTGAAGGATTATAATTGGTACGGCTATATCTCTAGAA

ATTCTGGTGATAGATACAATCATACTTTAGATCCTTCCAT

GAACGATTGGGTGAATACAATAGCCACTCCCGGAAATATC

AGCATTCAAACTTCTATAGCCTGGAATTTGCAAACTACTG

AGGGACAGGAACGTTATTTTATTCGCTGGGGAAGTTCGAA

TAAAAATACAACTCCTCTCTACTACAATCCTGAAAATGGA

CATCTCGCTCAGTATGATCCAATCAGTGGTTCTCTCTACT

GTATGTATTCTCAAGTAGACAACTATCAATGGAATTGGGT

GAAATGGAAATGGTGTAGTGATTCACTTGAAAGTAAAAGC

AAGGGAAATCCAACTTTTTGGAATGTCTTTTTTGAAACTG

ATCAAGGAGGAATGATTACAGATTATAAGGGAAATGCGCT

GAGAGTTACTAGATATGGAAGCAATTGGGGTGTTGCTTAT

ACGGCTAAGCCTGATTTTGTCAAAACGGATACTAAGAATA

GTCCCACTTCTTTATTTGTAGTTGATAAAAGCTTACTGGA

TTGGACACGTTATACGTCTTCTAATCTTGGAAAGACAGAG

CAGTATTGTCCAGCTGGTAATAAAGAAAGTGTTGTACATA

AAAAAGCCAAAAGAACCTTACCGCCCGACTTTCAATTAAC

TGAGGCTTGGATTAGAAGACTTTATGAAATAGCAAGGACG

GATCCAAGTTCGCGTACGTCACGTGGAGTATGTGGTGTTT

GTATGCTTCAAGCTCTTCAGATGATAGCAGAACTCCAGGA

GTATCATTCTCAAGGACCTCTTCAGAGTGGAGGTTACTTC

TTCAATACGGCTCCTAATACAAACCCTTTTATCTCGTTCG

GACAACGTTATCCGCACTTGGACAGGTTGCTAGTAGATAT

TTACAGAGTGTTTGACCATTTCTTTGACACAAGCCATACG

TTAGGATACTTATCTGCTATGAATCTCTTACCTCAGTACG

AATGGGGGCGCACTCGTGAATTCTCCACTATGTCTGAAAT

ACGATCCCACATTAGATCACTCATAACTTCCCCACCCGGA

AATATTTGGCTAGTGTTAATGACAATGATTTATCCAGATG

GAACGAGAGGAGGGCATGCGGTTCCAATTCTTAGAACCCC

TCAAGGATTAGTTGTAATTGAAACAACCATGGCAACCGCA

ACATTTGAAGAATACAGAGCAGCGTTAAGACCCACTACAG

ATTTTGAACAGATAATTAGAAATCTGAGAGGACCCAATAA

TATTCTAATAGGACTTTCAACTTTACAATTAGGAAGATTT

TACCACAATCCGTTGGACTCTATGATATCTAACAGAAATT

GCACCGGGGAAGGAAGTGATAGAAGAGGCACAGGAGGATA

TCCAGCTAGCACATCGGTAAACCAATGCTCAAGTAAAAGC

AGCCGGTGCTCCCTGCAGTAA nucleic acid sequence of native *Leptospira*
*interrogans serovar Lai* wildtype encoding
LA_3490
(full length minus encoded predicted
signal peptide).

SEQ ID NO: 9

CGAGTATGGAGTAAATCATACACATATCCACGCTTTATCA

AAAATTGAATACTCGGTTATTCAAAAACCTACCGATCCAC

CAAAAGACAAACCAATCAAAGTAATTGTAAGCGATGGAGG

AAAGTTTTGTTACGGTCCTAATTTTAGCGGAGGTGAAAGT

TATATTATAATTGAACAGTGTTGGCAAATGCACGTTATGA

ATGCAAGATACGACGTGTTTCAAAGAATTTCGTATAACAT

CAATAATACGTGGTTATGTATTACTGCTCCGGAGAAAGTA

ATTAAAGCAGAGAAAAACTGGGACTATGTTCATCTCAGAC

CTTGTACGATCAATGATCCTCTGCAAAGATGGATTATAAA

AAACAATTCTTTTTGGACTGCAAATGGGTTTTACCGATTG

AAGGATTATAATTGGTACGGTTATATCTCTAGAAATTCTG

GTGATAGATACAATCATACTTTAGATTCTTCCATGAACGA

TTGGGTGAATACAATAGCTACTCCCGGAAATATTAGCATT

CAAACTTCTATAGCCTGGAATTTGCAAACTACTGAGGGAC

AGGAACGTTATTTTATTCGCTGGGGTGGTTCAGATAAAAA

TACAACTCCTCTCTACTACAATCCTGAAAATGGACATCTC

GCTCAGTATGATCCAATCAGTGGTTCTCTCTATTGTATGT

ATTCTCAGGTAGACAACTATCAATGGAATTGGGTGAAATG

GAAATGGTGTAGTGATTTACTTGAAAGTAAAAGCAAGGGA

AATCCAACTTTTTGGAATGTCTTTTTTTGAAACTGATCAAG

GAGGAATGATTACAGATTATAAGGGAAATGCGCTGAGAGT

TACTAGATATGGATCCAATTGGGGCTCTGCCTATACAGCC

AAACCTTCTTATTTAGAAAAGGACACTACCAATAGCCCAA

CTTCTCTGTTTGTTGTTAATAAAGATTTATTGGATTGGAC

ACGTTATACAGCAAGTAACCTTGGTAAAACAGGACAATAT

TGTCCGGCTGGCAAAAGAGAAAATATTGTACATAGAAGAG

TCAAAAGAGAATTACCACCCGACTTTCAATTAACTGAGGC

TTGGATCCGAAGACTTTATGAAATAGCAACTTCAGTTTCC

GCTGAATCCGAGACTCGAGTCAGTGGAATCTGTGGCCCTT

GTGCTCTTCATAGCTTTCAGATGTTGGCAGAGCTTCTGGA

GTATCATTCTCGAGAACCTCTTCAGAGTGGAGGTTACTTT

TTTGATACAGCTCCAAATACAGATCCTTTTATATCGTTTG

GTCAACGTTATCCGCATTTGGAAAGACTGTTAGAAGATAT

ACCTAAAAAGTATGCTCCTTATCCTCACTATTCTACACAA

AGTTTCTTATCATTTGCATCTATTGATTCTATGCTGCCCC

AATATTTTTGGTCTGCTTCTACTGAATTTACGAATCGGGA

TGAGATTCTTTCTCACATTAGCTCACTTATTAATTCCCCT

GCTGGAAGCATTTGGTTAGGAGTCATGGAGCAACAACATC

-continued

CTGATGGAACCATAACAGGACACGCAGCTCCAATTCTTAG

AATCTCTCAGGGATTAGTAGTAATTCCAACTAACGTGCAT

TTGTGGACATTAGAAGAATTCAGAAGATTTTTAATACCCA

CCACAGAGCTGTCTCAAATAGTTGCGAATTTGGAAGGATC

AAATACACTGATAAGGTTTACAACTATACAATCATTGGGA

ATGCTCACAACAAATATGTTTGATTCCATGGTCTCTAACA

GAAATTGTACGGGAGAGGGAGAAGACAGAAGAGGTTCTGG

AGAATATCCAACAAGTACATCCGTAAATCAATGTCCAAGC

GGCAGATGTGCATTACCATTTTAA predicted Ricin B domain LA_0620 (short).
bp213-483
SEQ ID NO: 10
GAAAGTTACATTATAATTGAACAGTGTTGGCAAATGCACG

TTATGAATGCAAGATACGACGTGTTTCAAAGAATTTCGTA

TAACATCAATAATACGTGGTTATGTATTACTGCTCCGGAG

AAAGTAATTAAAGCAGAAGAAACCTGGGACTATGTTCATC

TCAGACCTTGTACGATCAATGATCCTCTGCAGAGATGGAT

-continued

TATAAAAAACAATTCTTTTTGGACTGCAAATGGGTTTTAC

CGATTGAAGGATTATAATTGGTACGGCTAT predicted Ricin B domain LA_3490 (short).
bp213-480
SEQ ID NO: 11
GAAAGTTATATTATAATTGAACAGTGTTGGCAAATGCACG

TTATGAATGCAAGATACGACGTGTTTCAAAGAATTTCGTA

TAACATCAATAATACGTGGTTATGTATTACTGCTCCGGAG

AAAGTAATTAAAGCAGAGAAAACTGGGACTATGTTCATC

TCAGACCTTGTACGATCAATGATCCTCTGCAAAGATGGAT

TATAAAAAACAATTCTTTTTGGACTGCAAATGGGTTTTAC

CGATTGAAGGATTATAATTGGTACGGTTAT

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A pharmaceutical composition comprising a Leptospiral virulence modifying (VM) protein LA_3490 and a pharmaceutically acceptable adjuvant, wherein the VM protein comprises an amino acid sequence selected from the group consisting of:

a) SEQ ID NO:2, and b) a functional fragment of SEQ ID NO:2 comprising two ricin B chain-like functional domains, wherein the ricin B chain-like functional domains are N-terminal fragments of a full-length Leptospiral VM protein LA_3490, wherein the two N-terminal ricin B chain-like functional domains comprise a targeting domain, and wherein the pharmaceutical composition is a vaccine that elicits a protective immune response.

2. The pharmaceutical composition of claim 1, wherein the composition comprises a fusion protein comprising a Leptospiral VM domain and a targeting domain specific for binding to an antigen, wherein the fusion protein comprises a) a Leptospiral VM domain of a full-length Leptospiral VM protein LA_3490 and the targeting domain, or b) the two ricin B chain-like functional domains alone.

3. The pharmaceutical composition of claim 2, wherein the targeting domain specifically binds to an antigen selected from the group consisting of a bacterial antigen, viral antigen, parasitic antigen, cancer antigen, tumor-associated antigen, and tumor-specific antigen.

4. The pharmaceutical composition of claim 1, wherein the ricin B chain-like functional domain comprises an amino acid sequence of SEQ ID NO: 4.

5. A method of inducing an immune response in a subject, the method comprising administering the pharmaceutical composition of claim 1 to the subject.

6. The method of claim 5, wherein the subject is currently infected with Leptospira sp and the composition induces an immune response against Leptospira sp.

7. The method of claim 5, wherein the subject is not currently infected with Leptospira sp and the composition induces an immune response against Leptospira sp.

8. A method of treating or preventing a Leptospira sp bacterial infection in a subject, comprising administering a pharmaceutical composition of claim 1 to the subject.

9. A method treating or preventing a disease or disorder in a subject, comprising administering a pharmaceutical composition comprising a fusion protein of claim 2 to the subject.

10. The method of claim 9, wherein the disease or disorder is caused by a Leptospira sp infection.

* * * * *

SEQUENCE LISTING

<160> NUMBER OF SEQ ID NOS: 11

<210> SEQ ID NO 1
<211> LENGTH: 606
<212> TYPE: PRT
<213> ORGANISM: Leptospira interrogans

<400> SEQUENCE: 1

```
Ser Ser Lys Ile Glu Tyr Ser Val Ile Gln Lys Pro Thr Asp Pro Pro
1               5                   10                  15

Lys Asp Lys Pro Ile Lys Val Ile Val Ser Asp Gly Gly Lys Phe Cys
            20                  25                  30

Tyr Gly Pro Asn Phe Ser Gly Gly Glu Ser Tyr Ile Ile Ile Glu Gln
        35                  40                  45

Cys Trp Gln Met His Val Met Asn Ala Arg Tyr Asp Val Phe Gln Arg
    50                  55                  60

Ile Ser Tyr Asn Ile Asn Asn Thr Trp Leu Cys Ile Thr Ala Pro Glu
65                  70                  75                  80

Lys Val Ile Lys Ala Glu Glu Thr Trp Asp Tyr Val His Leu Arg Pro
                85                  90                  95

Cys Thr Ile Asn Asp Pro Leu Gln Arg Trp Ile Ile Lys Asn Asn Ser
            100                 105                 110

Phe Trp Thr Ala Asn Gly Phe Tyr Arg Leu Lys Asp Tyr Asn Trp Tyr
        115                 120                 125

Gly Tyr Ile Ser Arg Asn Ser Gly Asp Arg Tyr Asn His Thr Leu Asp
    130                 135                 140

Pro Ser Met Asn Asp Trp Val Asn Thr Ile Ala Thr Pro Gly Asn Ile
145                 150                 155                 160

Ser Ile Gln Thr Ser Ile Ala Trp Asn Leu Gln Thr Thr Glu Gly Gln
                165                 170                 175

Glu Arg Tyr Phe Ile Arg Trp Gly Ser Ser Asn Lys Asn Thr Thr Pro
```

```
                  180                185                190
Leu Tyr Tyr Asn Pro Glu Asn Gly His Leu Ala Gln Tyr Asp Pro Ile
            195                200                205
Ser Gly Ser Leu Tyr Cys Met Tyr Ser Gln Val Asp Asn Tyr Gln Trp
       210                215                220
Asn Trp Val Lys Trp Lys Trp Cys Ser Asp Ser Leu Glu Ser Lys Ser
225                230                235                240
Lys Gly Asn Pro Thr Phe Trp Asn Val Phe Phe Glu Thr Asp Gln Gly
            245                250                255
Gly Met Ile Thr Asp Tyr Lys Gly Asn Ala Leu Arg Val Thr Arg Tyr
            260                265                270
Gly Ser Asn Trp Gly Val Ala Tyr Thr Ala Lys Pro Asp Phe Val Lys
       275                280                285
Thr Asp Thr Lys Asn Ser Pro Thr Ser Leu Phe Val Val Asp Lys Ser
       290                295                300
Leu Leu Asp Trp Thr Arg Tyr Thr Ser Ser Asn Leu Gly Lys Thr Glu
305                310                315                320
Gln Tyr Cys Pro Ala Gly Asn Lys Glu Ser Val Val His Lys Lys Ala
            325                330                335
Lys Arg Thr Leu Pro Pro Asp Phe Gln Leu Thr Glu Ala Trp Ile Arg
            340                345                350
Arg Leu Tyr Glu Ile Ala Arg Thr Asp Pro Ser Ser Arg Thr Ser Arg
            355                360                365
Gly Val Cys Gly Val Cys Met Leu Gln Ala Leu Gln Met Ile Ala Glu
       370                375                380
Leu Gln Glu Tyr His Ser Gln Gly Pro Leu Gln Ser Gly Gly Tyr Phe
385                390                395                400
Phe Asn Thr Ala Pro Asn Thr Asn Pro Phe Ile Ser Phe Gly Gln Arg
            405                410                415
Tyr Pro His Leu Asp Arg Leu Leu Val Asp Ile Tyr Arg Val Phe Asp
            420                425                430
His Phe Phe Asp Thr Ser His Thr Leu Gly Tyr Leu Ser Ala Met Asn
            435                440                445
Leu Leu Pro Gln Tyr Glu Trp Gly Arg Thr Arg Glu Phe Ser Thr Met
       450                455                460
Ser Glu Ile Arg Ser His Ile Arg Ser Leu Ile Thr Ser Pro Pro Gly
465                470                475                480
Asn Ile Trp Leu Val Leu Met Thr Met Ile Tyr Pro Asp Gly Thr Arg
            485                490                495
Gly Gly His Ala Val Pro Ile Leu Arg Thr Pro Gln Gly Leu Val Val
            500                505                510
Ile Glu Thr Thr Met Ala Thr Ala Thr Phe Glu Glu Tyr Arg Ala Ala
            515                520                525
Leu Arg Pro Thr Thr Asp Phe Glu Gln Ile Ile Arg Asn Leu Arg Gly
       530                535                540
Pro Asn Asn Ile Leu Ile Gly Leu Ser Thr Leu Gln Leu Gly Arg Phe
545                550                555                560
Tyr His Asn Pro Leu Asp Ser Met Ile Ser Asn Arg Asn Cys Thr Gly
            565                570                575
Glu Gly Ser Asp Arg Arg Gly Thr Gly Gly Tyr Pro Ala Ser Thr Ser
            580                585                590
Val Asn Gln Cys Ser Ser Lys Ser Ser Arg Cys Ser Leu Gln
            595                600                605
```

```
<210> SEQ ID NO 2
<211> LENGTH: 621
<212> TYPE: PRT
<213> ORGANISM: Leptospira interrogans

<400> SEQUENCE: 2

Phe Glu Tyr Gly Val Asn His Thr His Ile His Ala Leu Ser Lys Ile
1               5                   10                  15

Glu Tyr Ser Val Ile Gln Lys Pro Thr Asp Pro Pro Lys Asp Lys Pro
                20                  25                  30

Ile Lys Val Ile Val Ser Asp Gly Gly Lys Phe Cys Tyr Gly Pro Asn
            35                  40                  45

Phe Ser Gly Gly Glu Ser Tyr Ile Ile Ile Glu Gln Cys Trp Gln Met
        50                  55                  60

His Val Met Asn Ala Arg Tyr Asp Val Phe Gln Arg Ile Ser Tyr Asn
65                  70                  75                  80

Ile Asn Asn Thr Trp Leu Cys Ile Thr Ala Pro Glu Lys Val Ile Lys
                85                  90                  95

Ala Glu Lys Asn Trp Asp Tyr Val His Leu Arg Pro Cys Thr Ile Asn
                100                 105                 110

Asp Pro Leu Gln Arg Trp Ile Ile Lys Asn Asn Ser Phe Trp Thr Ala
            115                 120                 125

Asn Gly Phe Tyr Arg Leu Lys Asp Tyr Asn Trp Tyr Gly Tyr Ile Ser
        130                 135                 140

Arg Asn Ser Gly Asp Arg Tyr Asn His Thr Leu Asp Ser Ser Met Asn
145                 150                 155                 160

Asp Trp Val Asn Thr Ile Ala Thr Pro Gly Asn Ile Ser Ile Gln Thr
                165                 170                 175

Ser Ile Ala Trp Asn Leu Gln Thr Thr Glu Gly Gln Glu Arg Tyr Phe
                180                 185                 190

Ile Arg Trp Gly Gly Ser Asp Lys Asn Thr Thr Pro Leu Tyr Tyr Asn
            195                 200                 205

Pro Glu Asn Gly His Leu Ala Gln Tyr Asp Pro Ile Ser Gly Ser Leu
        210                 215                 220

Tyr Cys Met Tyr Ser Gln Val Asp Asn Tyr Gln Trp Asn Trp Val Lys
225                 230                 235                 240

Trp Lys Trp Cys Ser Asp Leu Leu Glu Ser Lys Ser Lys Gly Asn Pro
                245                 250                 255

Thr Phe Trp Asn Val Phe Phe Glu Thr Asp Gln Gly Gly Met Ile Thr
                260                 265                 270

Asp Tyr Lys Gly Asn Ala Leu Arg Val Thr Arg Tyr Gly Ser Asn Trp
            275                 280                 285

Gly Ser Ala Tyr Thr Ala Lys Pro Ser Tyr Leu Glu Lys Asp Thr Thr
        290                 295                 300

Asn Ser Pro Thr Ser Leu Phe Val Val Asn Lys Asp Leu Leu Asp Trp
305                 310                 315                 320

Thr Arg Tyr Thr Ala Ser Asn Leu Gly Lys Thr Gly Gln Tyr Cys Pro
                325                 330                 335

Ala Gly Lys Arg Glu Asn Ile Val His Arg Arg Val Lys Arg Glu Leu
            340                 345                 350

Pro Pro Asp Phe Gln Leu Thr Glu Ala Trp Ile Arg Arg Leu Tyr Glu
        355                 360                 365

Ile Ala Thr Ser Val Ser Ala Glu Ser Glu Thr Arg Val Ser Gly Ile
```

-continued

```
              370                 375                 380

Cys Gly Pro Cys Ala Leu His Ser Phe Gln Met Leu Ala Glu Leu Leu
385                 390                 395                 400

Glu Tyr His Ser Arg Glu Pro Leu Gln Ser Gly Gly Tyr Phe Phe Asp
                405                 410                 415

Thr Ala Pro Asn Thr Asp Pro Phe Ile Ser Phe Gly Gln Arg Tyr Pro
                420                 425                 430

His Leu Glu Arg Leu Leu Glu Asp Ile Pro Lys Lys Tyr Ala Pro Tyr
                435                 440                 445

Pro His Tyr Ser Thr Gln Ser Phe Leu Ser Phe Ala Ser Ile Asp Ser
                450                 455                 460

Met Leu Pro Gln Tyr Phe Trp Ser Ala Ser Thr Glu Phe Thr Asn Arg
465                 470                 475                 480

Asp Glu Ile Leu Ser His Ile Ser Ser Leu Ile Asn Ser Pro Ala Gly
                485                 490                 495

Ser Ile Trp Leu Gly Val Met Glu Gln Gln His Pro Asp Gly Thr Ile
                500                 505                 510

Thr Gly His Ala Ala Pro Ile Leu Arg Ile Ser Gln Gly Leu Val Val
                515                 520                 525

Ile Pro Thr Asn Val His Leu Trp Thr Leu Glu Glu Phe Arg Arg Phe
                530                 535                 540

Leu Ile Pro Thr Thr Glu Leu Ser Gln Ile Val Ala Asn Leu Glu Gly
545                 550                 555                 560

Ser Asn Thr Leu Ile Arg Phe Thr Thr Ile Gln Ser Leu Gly Met Leu
                565                 570                 575

Thr Thr Asn Met Phe Asp Ser Met Val Ser Asn Arg Asn Cys Thr Gly
                580                 585                 590

Glu Gly Glu Asp Arg Arg Gly Ser Gly Glu Tyr Pro Thr Ser Thr Ser
                595                 600                 605

Val Asn Gln Cys Pro Ser Gly Arg Cys Ala Leu Pro Phe
                610                 615                 620
```

```
<210> SEQ ID NO 3
<211> LENGTH: 90
<212> TYPE: PRT
<213> ORGANISM: Artificial Sequence
<220> FEATURE:
<223> OTHER INFORMATION: Chemically synthesized, predicted Ricin B-like
      domain

<400> SEQUENCE: 3

Glu Ser Tyr Ile Ile Ile Glu Gln Cys Trp Gln Met His Val Met Asn
1               5                   10                  15

Ala Arg Tyr Asp Val Phe Gln Arg Ile Ser Tyr Asn Ile Asn Asn Thr
                20                  25                  30

Trp Leu Cys Ile Thr Ala Pro Glu Lys Val Ile Lys Ala Glu Glu Thr
                35                  40                  45

Trp Asp Tyr Val His Leu Arg Pro Cys Thr Ile Asn Asp Pro Leu Gln
                50                  55                  60

Arg Trp Ile Ile Lys Asn Asn Ser Phe Trp Thr Ala Asn Gly Phe Tyr
65                  70                  75                  80

Arg Leu Lys Asp Tyr Asn Trp Tyr Gly Tyr
                85                  90

<210> SEQ ID NO 4
<211> LENGTH: 90
```

-continued

```
<212> TYPE: PRT
<213> ORGANISM: Artificial Sequence
<220> FEATURE:
<223> OTHER INFORMATION: Chemically synthesized, predicted Ricin B-like
      domain

<400> SEQUENCE: 4

Glu Ser Tyr Ile Ile Ile Glu Gln Cys Trp Gln Met His Val Met Asn
1               5                   10                  15

Ala Arg Tyr Asp Val Phe Gln Arg Ile Ser Tyr Asn Ile Asn Asn Thr
            20                  25                  30

Trp Leu Cys Ile Thr Ala Pro Glu Lys Val Ile Lys Ala Glu Lys Asn
        35                  40                  45

Trp Asp Tyr Val His Leu Arg Pro Cys Thr Ile Asn Asp Pro Leu Gln
    50                  55                  60

Arg Trp Ile Ile Lys Asn Asn Ser Phe Trp Thr Ala Asn Gly Phe Tyr
65                  70                  75                  80

Arg Leu Lys Asp Tyr Asn Trp Tyr Gly Tyr
                85                  90

<210> SEQ ID NO 5
<211> LENGTH: 5
<212> TYPE: PRT
<213> ORGANISM: Artificial Sequence
<220> FEATURE:
<223> OTHER INFORMATION: Chemically synthesized, enterokinase cleavage
      site

<400> SEQUENCE: 5

Asp Asp Asp Asp Lys
1               5

<210> SEQ ID NO 6
<211> LENGTH: 862
<212> TYPE: PRT
<213> ORGANISM: Artificial Sequence
<220> FEATURE:
<223> OTHER INFORMATION: Chemically synthesized, LA_0620 (full)-mCherry
      Fusion protein including Gly4Ser linkers and an enterokinase
      cleavage site

<400> SEQUENCE: 6

Ser Ser Lys Ile Glu Tyr Ser Val Ile Gln Lys Pro Thr Asp Pro Pro
1               5                   10                  15

Lys Asp Lys Pro Ile Lys Val Ile Val Ser Asp Gly Gly Lys Phe Cys
            20                  25                  30

Tyr Gly Pro Asn Phe Ser Gly Gly Glu Ser Tyr Ile Ile Ile Glu Gln
        35                  40                  45

Cys Trp Gln Met His Val Met Asn Ala Arg Tyr Asp Val Phe Gln Arg
    50                  55                  60

Ile Ser Tyr Asn Ile Asn Asn Thr Trp Leu Cys Ile Thr Ala Pro Glu
65                  70                  75                  80

Lys Val Ile Lys Ala Glu Glu Thr Trp Asp Tyr Val His Leu Arg Pro
                85                  90                  95

Cys Thr Ile Asn Asp Pro Leu Gln Arg Trp Ile Ile Lys Asn Asn Ser
            100                 105                 110

Phe Trp Thr Ala Asn Gly Phe Tyr Arg Leu Lys Asp Tyr Asn Trp Tyr
        115                 120                 125

Gly Tyr Ile Ser Arg Asn Ser Gly Asp Arg Tyr Asn His Thr Leu Asp
    130                 135                 140
```

-continued

```
Pro Ser Met Asn Asp Trp Val Asn Thr Ile Ala Thr Pro Gly Asn Ile
145                 150                 155                 160

Ser Ile Gln Thr Ser Ile Ala Trp Asn Leu Gln Thr Thr Glu Gly Gln
                165                 170                 175

Glu Arg Tyr Phe Ile Arg Trp Gly Ser Ser Asn Lys Asn Thr Thr Pro
            180                 185                 190

Leu Tyr Tyr Asn Pro Glu Asn Gly His Leu Ala Gln Tyr Asp Pro Ile
        195                 200                 205

Ser Gly Ser Leu Tyr Cys Met Tyr Ser Gln Val Asp Asn Tyr Gln Trp
    210                 215                 220

Asn Trp Val Lys Trp Lys Trp Cys Ser Asp Ser Leu Glu Ser Lys Ser
225                 230                 235                 240

Lys Gly Asn Pro Thr Phe Trp Asn Val Phe Phe Glu Thr Asp Gln Gly
            245                 250                 255

Gly Met Ile Thr Asp Tyr Lys Gly Asn Ala Leu Arg Val Thr Arg Tyr
            260                 265                 270

Gly Ser Asn Trp Gly Val Ala Tyr Thr Ala Lys Pro Asp Phe Val Lys
        275                 280                 285

Thr Asp Thr Lys Asn Ser Pro Thr Ser Leu Phe Val Val Asp Lys Ser
    290                 295                 300

Leu Leu Asp Trp Thr Arg Tyr Thr Ser Ser Asn Leu Gly Lys Thr Glu
305                 310                 315                 320

Gln Tyr Cys Pro Ala Gly Asn Lys Glu Ser Val Val His Lys Lys Ala
            325                 330                 335

Lys Arg Thr Leu Pro Pro Asp Phe Gln Leu Thr Glu Ala Trp Ile Arg
            340                 345                 350

Arg Leu Tyr Glu Ile Ala Arg Thr Asp Pro Ser Ser Arg Thr Ser Arg
        355                 360                 365

Gly Val Cys Gly Val Cys Met Leu Gln Ala Leu Gln Met Ile Ala Glu
    370                 375                 380

Leu Gln Glu Tyr His Ser Gln Gly Pro Leu Gln Ser Gly Gly Tyr Phe
385                 390                 395                 400

Phe Asn Thr Ala Pro Asn Thr Asn Pro Phe Ile Ser Phe Gly Gln Arg
            405                 410                 415

Tyr Pro His Leu Asp Arg Leu Leu Val Asp Ile Tyr Arg Val Phe Asp
            420                 425                 430

His Phe Phe Asp Thr Ser His Thr Leu Gly Tyr Leu Ser Ala Met Asn
        435                 440                 445

Leu Leu Pro Gln Tyr Glu Trp Gly Arg Thr Arg Glu Phe Ser Thr Met
    450                 455                 460

Ser Glu Ile Arg Ser His Ile Arg Ser Leu Ile Thr Ser Pro Pro Gly
465                 470                 475                 480

Asn Ile Trp Leu Val Leu Met Thr Met Ile Tyr Pro Asp Gly Thr Arg
            485                 490                 495

Gly Gly His Ala Val Pro Ile Leu Arg Thr Pro Gln Gly Leu Val Val
        500                 505                 510

Ile Glu Thr Thr Met Ala Thr Ala Thr Phe Glu Glu Tyr Arg Ala Ala
        515                 520                 525

Leu Arg Pro Thr Thr Asp Phe Glu Gln Ile Ile Arg Asn Leu Arg Gly
    530                 535                 540

Pro Asn Asn Ile Leu Ile Gly Leu Ser Thr Leu Gln Leu Gly Arg Phe
545                 550                 555                 560

Tyr His Asn Pro Leu Asp Ser Met Ile Ser Asn Arg Asn Cys Thr Gly
```

-continued

```
                  565                 570                 575
Glu Gly Ser Asp Arg Arg Gly Thr Gly Gly Tyr Pro Ala Ser Thr Ser
            580                 585                 590

Val Asn Gln Cys Ser Ser Lys Ser Ser Arg Cys Ser Leu Gln Gly Gly
        595                 600                 605

Gly Gly Ser Gly Gly Gly Gly Ser Gly Gly Gly Gly Ser Asp Asp Asp
    610                 615                 620

Asp Lys Met Val Ser Lys Gly Glu Glu Asp Asn Met Ala Ile Ile Lys
625                 630                 635                 640

Glu Phe Met Arg Phe Lys Val His Met Glu Gly Ser Val Asn Gly His
            645                 650                 655

Glu Phe Glu Ile Glu Gly Glu Gly Glu Gly Arg Pro Tyr Glu Gly Thr
                660                 665                 670

Gln Thr Ala Lys Leu Lys Val Thr Lys Gly Gly Pro Leu Pro Phe Ala
            675                 680                 685

Trp Asp Ile Leu Ser Pro Gln Phe Met Tyr Gly Ser Lys Ala Tyr Val
    690                 695                 700

Lys His Pro Ala Asp Ile Pro Asp Tyr Leu Lys Leu Ser Phe Pro Glu
705                 710                 715                 720

Gly Phe Lys Trp Glu Arg Val Met Asn Phe Glu Asp Gly Gly Val Val
                725                 730                 735

Thr Val Thr Gln Asp Ser Ser Leu Gln Asp Gly Glu Phe Ile Tyr Lys
            740                 745                 750

Val Lys Leu Arg Gly Thr Asn Phe Pro Ser Asp Gly Pro Val Met Gln
            755                 760                 765

Lys Lys Thr Met Gly Trp Glu Ala Ser Ser Glu Arg Met Tyr Pro Glu
    770                 775                 780

Asp Gly Ala Leu Lys Gly Glu Ile Lys Gln Arg Leu Lys Leu Lys Asp
785                 790                 795                 800

Gly Gly His Tyr Asp Ala Glu Val Lys Thr Thr Tyr Lys Ala Lys Lys
                805                 810                 815

Pro Val Gln Leu Pro Gly Ala Tyr Asn Val Asn Ile Lys Leu Asp Ile
            820                 825                 830

Thr Ser His Asn Glu Asp Tyr Thr Ile Val Glu Gln Tyr Glu Arg Ala
            835                 840                 845

Glu Gly Arg His Ser Thr Gly Gly Met Asp Glu Leu Tyr Lys
    850                 855                 860
```

<210> SEQ ID NO 7
<211> LENGTH: 877
<212> TYPE: PRT
<213> ORGANISM: Artificial Sequence
<220> FEATURE:
<223> OTHER INFORMATION: Chemically Synthesized, LA_3490 (full)-mCherry
      Fusion protein including Gly4Ser linkers and an enterokinase
      cleavage site

<400> SEQUENCE: 7

```
Phe Glu Tyr Gly Val Asn His Thr His Ile His Ala Leu Ser Lys Ile
1               5                   10                  15

Glu Tyr Ser Val Ile Gln Lys Pro Thr Asp Pro Pro Lys Asp Lys Pro
            20                  25                  30

Ile Lys Val Ile Val Ser Asp Gly Gly Lys Phe Cys Tyr Gly Pro Asn
        35                  40                  45

Phe Ser Gly Gly Glu Ser Tyr Ile Ile Ile Glu Gln Cys Trp Gln Met
    50                  55                  60
```

-continued

```
His Val Met Asn Ala Arg Tyr Asp Val Phe Gln Arg Ile Ser Tyr Asn
65              70                  75                  80

Ile Asn Asn Thr Trp Leu Cys Ile Thr Ala Pro Glu Lys Val Ile Lys
                85                  90                  95

Ala Glu Lys Asn Trp Asp Tyr Val His Leu Arg Pro Cys Thr Ile Asn
            100                 105                 110

Asp Pro Leu Gln Arg Trp Ile Ile Lys Asn Asn Ser Phe Trp Thr Ala
            115                 120                 125

Asn Gly Phe Tyr Arg Leu Lys Asp Tyr Asn Trp Tyr Gly Tyr Ile Ser
        130                 135                 140

Arg Asn Ser Gly Asp Arg Tyr Asn His Thr Leu Asp Ser Ser Met Asn
145                 150                 155                 160

Asp Trp Val Asn Thr Ile Ala Thr Pro Gly Asn Ile Ser Ile Gln Thr
                165                 170                 175

Ser Ile Ala Trp Asn Leu Gln Thr Thr Glu Gly Gln Glu Arg Tyr Phe
            180                 185                 190

Ile Arg Trp Gly Gly Ser Asp Lys Asn Thr Thr Pro Leu Tyr Tyr Asn
            195                 200                 205

Pro Glu Asn Gly His Leu Ala Gln Tyr Asp Pro Ile Ser Gly Ser Leu
        210                 215                 220

Tyr Cys Met Tyr Ser Gln Val Asp Asn Tyr Gln Trp Asn Trp Val Lys
225                 230                 235                 240

Trp Lys Trp Cys Ser Asp Leu Leu Glu Ser Lys Ser Lys Gly Asn Pro
                245                 250                 255

Thr Phe Trp Asn Val Phe Phe Glu Thr Asp Gln Gly Gly Met Ile Thr
            260                 265                 270

Asp Tyr Lys Gly Asn Ala Leu Arg Val Thr Arg Tyr Gly Ser Asn Trp
            275                 280                 285

Gly Ser Ala Tyr Thr Ala Lys Pro Ser Tyr Leu Glu Lys Asp Thr Thr
        290                 295                 300

Asn Ser Pro Thr Ser Leu Phe Val Val Asn Lys Asp Leu Leu Asp Trp
305                 310                 315                 320

Thr Arg Tyr Thr Ala Ser Asn Leu Gly Lys Thr Gly Gln Tyr Cys Pro
                325                 330                 335

Ala Gly Lys Arg Glu Asn Ile Val His Arg Arg Val Lys Arg Glu Leu
            340                 345                 350

Pro Pro Asp Phe Gln Leu Thr Glu Ala Trp Ile Arg Arg Leu Tyr Glu
            355                 360                 365

Ile Ala Thr Ser Val Ser Ala Glu Ser Glu Thr Arg Val Ser Gly Ile
            370                 375                 380

Cys Gly Pro Cys Ala Leu His Ser Phe Gln Met Leu Ala Glu Leu Leu
385                 390                 395                 400

Glu Tyr His Ser Arg Glu Pro Leu Gln Ser Gly Gly Tyr Phe Phe Asp
                405                 410                 415

Thr Ala Pro Asn Thr Asp Pro Phe Ile Ser Phe Gly Gln Arg Tyr Pro
            420                 425                 430

His Leu Glu Arg Leu Leu Glu Asp Ile Pro Lys Lys Tyr Ala Pro Tyr
            435                 440                 445

Pro His Tyr Ser Thr Gln Ser Phe Leu Ser Phe Ala Ser Ile Asp Ser
        450                 455                 460

Met Leu Pro Gln Tyr Phe Trp Ser Ala Ser Thr Glu Phe Thr Asn Arg
465                 470                 475                 480
```

-continued

```
Asp Glu Ile Leu Ser His Ile Ser Ser Leu Ile Asn Ser Pro Ala Gly
            485                 490                 495

Ser Ile Trp Leu Gly Val Met Glu Gln Gln His Pro Asp Gly Thr Ile
            500                 505                 510

Thr Gly His Ala Ala Pro Ile Leu Arg Ile Ser Gln Gly Leu Val Val
            515                 520                 525

Ile Pro Thr Asn Val His Leu Trp Thr Leu Glu Glu Phe Arg Arg Phe
    530                 535                 540

Leu Ile Pro Thr Thr Glu Leu Ser Gln Ile Val Ala Asn Leu Glu Gly
545                 550                 555                 560

Ser Asn Thr Leu Ile Arg Phe Thr Thr Ile Gln Ser Leu Gly Met Leu
            565                 570                 575

Thr Thr Asn Met Phe Asp Ser Met Val Ser Asn Arg Asn Cys Thr Gly
            580                 585                 590

Glu Gly Glu Asp Arg Arg Gly Ser Gly Glu Tyr Pro Thr Ser Thr Ser
            595                 600                 605

Val Asn Gln Cys Pro Ser Gly Arg Cys Ala Leu Pro Phe Gly Gly Gly
    610                 615                 620

Gly Ser Gly Gly Gly Gly Ser Gly Gly Gly Ser Asp Asp Asp Asp
625                 630                 635                 640

Lys Met Val Ser Lys Gly Glu Glu Asp Asn Met Ala Ile Ile Lys Glu
            645                 650                 655

Phe Met Arg Phe Lys Val His Met Glu Gly Ser Val Asn Gly His Glu
            660                 665                 670

Phe Glu Ile Glu Gly Glu Gly Glu Gly Arg Pro Tyr Glu Gly Thr Gln
            675                 680                 685

Thr Ala Lys Leu Lys Val Thr Lys Gly Gly Pro Leu Pro Phe Ala Trp
    690                 695                 700

Asp Ile Leu Ser Pro Gln Phe Met Tyr Gly Ser Lys Ala Tyr Val Lys
705                 710                 715                 720

His Pro Ala Asp Ile Pro Asp Tyr Leu Lys Leu Ser Phe Pro Glu Gly
            725                 730                 735

Phe Lys Trp Glu Arg Val Met Asn Phe Glu Asp Gly Gly Val Val Thr
            740                 745                 750

Val Thr Gln Asp Ser Ser Leu Gln Asp Gly Glu Phe Ile Tyr Lys Val
            755                 760                 765

Lys Leu Arg Gly Thr Asn Phe Pro Ser Asp Gly Pro Val Met Gln Lys
    770                 775                 780

Lys Thr Met Gly Trp Glu Ala Ser Ser Glu Arg Met Tyr Pro Glu Asp
785                 790                 795                 800

Gly Ala Leu Lys Gly Glu Ile Lys Gln Arg Leu Lys Leu Lys Asp Gly
            805                 810                 815

Gly His Tyr Asp Ala Glu Val Lys Thr Thr Tyr Lys Ala Lys Lys Pro
            820                 825                 830

Val Gln Leu Pro Gly Ala Tyr Asn Val Asn Ile Lys Leu Asp Ile Thr
            835                 840                 845

Ser His Asn Glu Asp Tyr Thr Ile Val Glu Gln Tyr Glu Arg Ala Glu
    850                 855                 860

Gly Arg His Ser Thr Gly Gly Met Asp Glu Leu Tyr Lys
865                 870                 875
```

<210> SEQ ID NO 8
<211> LENGTH: 1821
<212> TYPE: DNA

<213> ORGANISM: Leptospira interrogans

<400> SEQUENCE: 8

```
tcatcaaaaa ttgaatactc ggttattcaa aaacctaccg atccaccaaa agacaaacca        60
atcaaagtaa ttgtaagcga tggaggaaag ttttgttacg gtcctaattt tagcggaggt       120
gaaagttaca ttataattga acagtgttgg caaatgcacg ttatgaatgc aagatacgac       180
gtgtttcaaa gaatttcgta taacatcaat aatacgtggt tatgtattac tgctccggag       240
aaagtaatta aagcagaaga aacctgggac tatgttcatc tcagaccttg tacgatcaat       300
gatcctctgc agagatggat tataaaaaac aattcttttt ggactgcaaa tgggttttac       360
cgattgaagg attataattg gtacggctat atctctagaa attctggtga tagatacaat       420
catactttag atccttccat gaacgattgg gtgaatacaa tagccactcc cggaaatatc       480
agcattcaaa cttctatagc ctggaatttg caaactactg agggacagga acgttatttt       540
attcgctggg gaagttcgaa taaaaataca actcctctct actacaatcc tgaaaatgga       600
catctcgctc agtatgatcc aatcagtggt tctctctact gtatgtattc tcaagtagac       660
aactatcaat ggaattgggt gaaatggaaa tggtgtagtg attcacttga aagtaaaagc       720
aagggaaatc caacttttg gaatgtcttt tttgaaactg atcaaggagg aatgattaca       780
gattataagg gaaatgcgct gagagttact agatatggaa gcaattgggg tgttgcttat       840
acggctaagc ctgattttgt caaaacggat actaagaata gtcccacttc tttatttgta       900
gttgataaaa gcttactgga ttggacacgt tatacgtctt ctaatcttgg aaagacagag       960
cagtattgtc cagctggtaa taaagaaagt gttgtacata aaaaagccaa aagaaccttt      1020
ccgcccgact ttcaattaac tgaggcttgg attagaagac tttatgaaat agcaaggacg      1080
gatccaagtt cgcgtacgtc acgtggagta tgtggtgttt gtatgcttca agctcttcag      1140
atgatagcag aactccagga gtatcattct caaggacctc ttcagagtgg aggttacttc      1200
ttcaatacgg ctcctaatac aaaccctttt atctcgttcg acaacgttta ccgcacttg      1260 gacaggttgc tagtagatat ttacagagtg tttgaccatt tctttgacac aagccatacg      1320
ttaggatact tatctgctat gaatctctta cctcagtacg aatgggggcg cactcgtgaa      1380
ttctccacta tgtctgaaat acgatcccac attagatcac tcataacttc cccacccgga      1440
aatatttggc tagtgttaat gacaatgatt tatccagatg gaacgagagg agggcatgcg      1500
gttccaattc ttagaacccc tcaaggatta gttgtaattg aaacaaccat ggcaaccgca      1560
acatttgaag aatacagagc agcgttaaga cccactacag attttgaaca gataattaga      1620
aatctgagag gacccaataa tattctaata ggactttcaa ctttacaatt aggaagatt      1680 taccacaatc cgttggactc tatgatatct aacagaaatt gcaccgggga aggaagtgat      1740
agaagaggca caggaggata tccagctagc acatcggtaa accaatgctc aagtaaaagc      1800
agccggtgct ccctgcagta a                                               1821
```

<210> SEQ ID NO 9
<211> LENGTH: 1864
<212> TYPE: DNA
<213> ORGANISM: Leptospira interrogans

<400> SEQUENCE: 9

```
cgagtatgga gtaaatcata cacatatcca cgctttatca aaaattgaat actcggttat        60
tcaaaaacct accgatccac caaaagacaa accaatcaaa gtaattgtaa gcgatggagg       120
aaagttttgt tacggtccta attttagcgg aggtgaaagt tatattataa ttgaacagtg       180
```

-continued

```
ttggcaaatg cacgttatga atgcaagata cgacgtgttt caaagaattt cgtataacat          240
caataatacg tggttatgta ttactgctcc ggagaaagta attaaagcag agaaaaactg          300
ggactatgtt catctcagac cttgtacgat caatgatcct ctgcaaagat ggattataaa          360
aaacaattct ttttggactg caaatgggtt ttaccgattg aaggattata attggtacgg          420
ttatatctct agaaattctg gtgatagata caatcatact ttagattctt ccatgaacga          480
ttgggtgaat acaatagcta ctcccggaaa tattagcatt caaacttcta tagcctggaa          540
tttgcaaact actgagggac aggaacgtta ttttattcgc tggggtggtt cagataaaaa          600
tacaactcct ctctactaca atcctgaaaa tggacatctc gctcagtatg atccaatcag          660
tggttctctc tattgtatgt attctcaggt agacaactat caatggaatt gggtgaaatg          720
gaaatggtgt agtgatttac ttgaaagtaa aagcaaggga aatccaactt tttggaatgt          780 ctttttttgaa actgatcaag gaggaatgat tacagattat aagggaaatg cgctgagagt          840
tactagatat ggatccaatt ggggctctgc ctatacagcc aaaccttctt atttagaaaa          900
ggacactacc aatagcccaa cttctctgtt tgttgttaat aaagatttat tggattggac          960
acgttataca gcaagtaacc ttggtaaaac aggacaatat tgtccggctg gcaaaagaga         1020
aaatattgta catagaagag tcaaaagaga attaccaccc gactttcaat taactgaggc         1080
ttggatccga agactttatg aaatagcaac ttcagtttcc gctgaatccg agactcgagt         1140
cagtggaatc tgtggccctt gtgctcttca tagctttcag atgttggcag agcttctgga         1200
gtatcattct cgagaacctc ttcagagtgg aggttacttt tttgatacag ctccaaatac         1260
agatcctttt atatcgtttg gtcaacgtta tccgcatttg gaaagactgt tagaagatat         1320
acctaaaaag tatgctcctt atcctcacta ttctacacaa agtttcttat catttgcatc         1380
tattgattct atgctgcccc aatatttttg gtctgcttct actgaattta cgaatcggga         1440
tgagattctt tctcacatta gctcacttat taattcccct gctggaagca tttggttagg         1500
agtcatggag caacaacatc ctgatggaac cataacagga cacgcagctc caattcttag         1560
aatctctcag ggattagtag taattccaac taacgtgcat ttgtggacat tagaagaatt         1620
cagaagattt ttaatacccca ccacagagct gtctcaaata gttgcgaatt tggaaggatc         1680
aaatacactg ataaggttta caactataca atcattggga atgctcacaa caaatatgtt         1740
tgattccatg gtctctaaca gaaattgtac gggagaggga gaagacagaa gaggttctgg         1800
agaatatcca acaagtacat ccgtaaatca atgtccaagc ggcagatgtg cattaccatt         1860
ttaa                                                                      1864
```

```
<210> SEQ ID NO 10
<211> LENGTH: 270
<212> TYPE: DNA
<213> ORGANISM: Artificial Sequence
<220> FEATURE:
<223> OTHER INFORMATION: Chemically synthesized, predicted Ricin B
      domain LA_0620, short

<400> SEQUENCE: 10
gaaagttaca ttataattga acagtgttgg caaatgcacg ttatgaatgc aagatacgac           60
gtgtttcaaa gaatttcgta taacatcaat aatacgtggt tatgtattac tgctccggag          120
aaagtaatta aagcagaaga aacctgggac tatgttcatc tcagaccttg tacgatcaat          180
gatcctctgc agagatggat tataaaaaac aattcttttt ggactgcaaa tgggttttac          240
cgattgaagg attataattg gtacggctat                                           270
```

-continued

```
<210> SEQ ID NO 11
<211> LENGTH: 270
<212> TYPE: DNA
<213> ORGANISM: Artificial Sequence
<220> FEATURE:
<223> OTHER INFORMATION: Chemically Synthesized, predicted Ricin B
      domain LA_3490, short

<400> SEQUENCE: 11
gaaagttata ttataattga acagtgttgg caaatgcacg ttatgaatgc aagatacgac        60
gtgtttcaaa gaatttcgta taacatcaat aatacgtggt tatgtattac tgctccggag       120
aaagtaatta aagcagagaa aaactgggac tatgttcatc tcagaccttg tacgatcaat       180
gatcctctgc aaagatggat tataaaaaac aattcttttt ggactgcaaa tgggttttac       240
cgattgaagg attataattg gtacggttat                                         270
```